US005750717A

United States Patent [19]

Murai et al.

[11] Patent Number: 5,750,717
[45] Date of Patent: May 12, 1998

[54] 2-ISOXAZOLINE DERIVATIVE AND PROCESS FOR PRODUCING THE SAME, AND PROCESS FOR PRODUCING RELATED DERIVATIVES FROM THE SAME

[75] Inventors: Yoshiyuki Murai, Tsukuba; Masahiro Nishikawa; Yoichiro Ueda, both of Tsuba; Osamu Onomura, Tsukuba; Ichiro Takase, Arai, all of Japan

[73] Assignee: Daicel Chemical Industries, Ltd., Osaka, Japan

[21] Appl. No.: 702,582

[22] PCT Filed: Mar. 2, 1995

[86] PCT No.: PCT/JP95/00331

§ 371 Date: Sep. 3, 1996

§ 102(e) Date: Sep. 3, 1996

[87] PCT Pub. No.: WO95/23793

PCT Pub. Date: Sep. 8, 1995

[30] Foreign Application Priority Data

Mar. 2, 1994 [JP] Japan ..................................... 6-056639
Jul. 13, 1994 [JP] Japan ..................................... 6-183973

[51] Int. Cl.[6] ............................................ C07D 261/04
[52] U.S. Cl. ................................................... 548/240
[58] Field of Search .......................................... 548/240

[56] References Cited

U.S. PATENT DOCUMENTS 5,354,866  10/1994  Kempf et al. .................... 546/265

FOREIGN PATENT DOCUMENTS

WO94/14436  7/1994  WIPO .

*Primary Examiner*—Joseph McKane
*Attorney, Agent, or Firm*—Sherman and Shalloway

[57] ABSTRACT

The present invention provides useful intermediates for the synthesis of 2,5-diamino-1,6-diphenyl-3-hydroxyhexane derivatives which serve as intermediates in the synthesis of medicines such as retrovirus protease inhibitors including human immunodeficiency virus (HIV) protease inhibitors, and a method for preparing these intermediates using the former intermediates.

More particularly, the invention provides methods for preparing a 2-isoxazoline derivative represented by formula [1] and a 2,5-diamino-1,6-diphenyl-3-hydroxyhexane derivative obtainable by reducing the 2-isoxazoline derivative and represented by formula [6]:

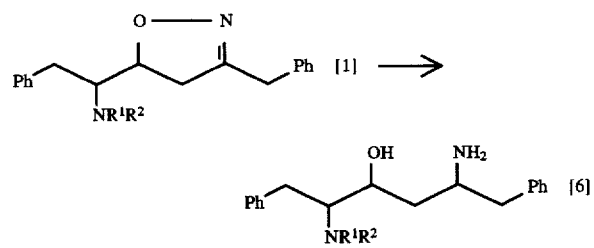

(wherein Ph is phenyl; and each of $R^1$ and $R^2$ independently represents hydrogen, acyl, alkyloxycarbonyl, arylalkyloxycarbonyl, aryloxycarbonyl, alkylaminocarbonyl, arylalkylaminocarbonyl, arylaminocarbonyl, alkyl, arylalkyl, aryl, alkylsulfonyl, arylalkylsulfonyl, or arylsulfonyl, or $R^1$ and $R^2$ are linked to each other to represent divalent acyl).

31 Claims, No Drawings

2-ISOXAZOLINE DERIVATIVE AND PROCESS FOR PRODUCING THE SAME, AND PROCESS FOR PRODUCING RELATED DERIVATIVES FROM THE SAME

This application is a 371 of PCT/JP95/00331 filed Mar. 2, 1995.

TECHNICAL FIELD

The present invention relates to novel 2-isoxazoline derivatives and acid addition salts thereof, and a method for preparing the derivatives and salts. The invention also relates to a method for preparing related derivatives by reducing the 2-isoxazoline derivatives.

More particularly, the present invention relates to novel 2-isoxazoline derivatives and acid addition salts thereof, which are useful intermediates for synthesizing 2,5-diamino-1,6-diphenyl-3-hydroxyhexane derivatives which in turn serve as intermediates in the synthesis of medicines such as retrovirus protease inhibitors including human immunodeficiency virus (HIV) protease inhibitors, and to a method for preparing the derivatives and salts. The invention also relates to a method for preparing 2,5-diamino-1,6-diphenyl-3-hydroxyhexane derivatives using the novel 2-isoxazoline derivatives.

BACKGROUND ART (2S,3S,5S)-2,5-Diamino-1,6-diphenyl-3-hydroxyhexane derivatives are known to be useful as intermediates for retrovirus protease inhibitors (JP-A-4-308574, International Publication No. WO94/14436, etc.). Methods for synthesizing the derivatives are known, including a method in which (2S,3R,4S,5S)-3-acetoxy-2,5-bis-(N-benzyloxycarbonylamino)-4-bromo-1,6-diphenylhexane derived from N-benzyloxycarbonyl-L-phenylalaninal is reacted with tri-n-butyltin hydride and 2,2'-azobis(2-methylpropionitrile) to give (2S,3S,5S)-3-acetoxy-2,5-bis (N-benzyloxycarbonylamino)-1,6-diphenylhexane (JP-A-4-308574 and International Publication No. WO94/14436, referred to as synthesizing method A), a method in which (2S,4S,5S)-5-tert-butoxycarbonylamino-4-tert-butyldimethylsilyloxy-6-phenyl-2-(phenylmethyl)hexanoic acid is reacted, in the presence of triethylamine, with diphenyl phosphorazidate [(PhO)$_2$P(O)N$_3$] and further with benzyl alcohol to give (2S,3S,5S)-2-tert-butoxycarbonylamino-3-tert-butyldimethylsilyloxy-5-benzyloxycarbonylamino-1,6-diphenylhexane (J. Org. Chem., 1993, 58, 1025, referred to as synthesizing method B), a method in which (2S,4S,5S)-5-tert-butoxycarbonylamino-4-tert-butyldimethylsilyloxy-6-phenyl-2-(phenylmethyl)hexanoic acid is reacted, in the presence of triethylamine, with diphenyl phosphorazidate [(PhO)$_2$P(O)N$_3$] and further with 3-pyridylcarbinol to give (2S,3S,5S)-2-tert-butoxycarbonylamino-3-tert-butyldimethylsilyloxy-5-(3-pyridylmethoxycarbonylamino)-1,6-diphenylhexane (J. Org. Chem., 1993, 58, 1025 and Tetrahedron, 1993, 49, 8739, referred to as synthesizing method C), a method in which (5S)-2-amino-5-(N,N-dibenzylamino)-4-oxo-1,6-diphenylhexa-2-ene is first reacted with sodium borohydride which has been treated with methanesulfonic acid and further reacted with sodium borohydride which has been treated with trifluoroacetic acid to give (2S,3S,5S)-5-amino-2-N,N-dibenzylamino-3-hydroxy-1,6-diphenylhexane (International Publication No. WO94/14436 and J. Org. Chem., 1994, 59, 4040, referred to as synthesizing method D), and a method in which (5S)-2-(tert-butoxycarbonylamino)-5-(N,N-dibenzylamino)-1,6-diphenyl-4-oxo-2-hexene is first reacted with diborane tetrahydrofuran complex and further reacted with lithium aluminum hydride or potassium borohydride to give (2S,3S,5S)-2-N,N-dibenzylamino-5-(tert-butoxycarbonylamino)-3-hydroxy-1,6-diphenylhexane (International Publication No. WO94/14436, referred to as synthesizing method E).

However, synthesizing method A (JP-A-4-308574) has drawbacks that it uses heavy metal reagents such as vanadium, zinc, and tin in the synthesis route including the synthesis of starting materials and that the reaction must be carried out at an extremely low temperature.

Synthesizing method B (J. Org. Chem., 1993, 58, 1025) and synthesizing method C (J. Org. Chem., 1993, 58, 1025 and Tetrahedron, 1993, 49, 8739) have drawbacks that they use a special reagent, diphenyl phosphorazidate [(PhO)$_2$P(O)N$_3$] in the synthesis route including the synthesis of starting materials, and that the reaction must be carried out at an extremely low temperature.

Synthesizing method D (International Publication No. WO94/14436 and J. Org. Chem., 1994, 59, 4040) and synthesizing method E (International Publication No. WO94/14436) have the drawback that the reaction must be carried out at an extremely low temperature in the synthesis route including the synthesis of starting materials.

Under the above circumstances, it has been desired to develop a practical method for synthesizing 2,5-diamino-1,6-diphenyl-3-hydroxyhexane derivatives which eliminates the necessity of heavy metal reagents, special reagents, and extremely low temperatures for reaction.

The present inventors carried out extensive studies, and found novel 2-isoxazoline derivatives and acid addition salts thereof, which are very useful intermediates for 2,5-diamino-1,6-diphenyl-3-hydroxyhexane derivatives which in turn serve as intermediates in the synthesis of medicines such as retrovirus protease inhibitors, a method for preparing the derivatives and salts, and a method for preparing 2,5-diamino-1,6-diphenyl-3-hydroxyhexane derivatives using the novel 2-isoxazoline derivatives.

DISCLOSURE OF THE INVENTION

Accordingly, the present invention provides a 2-isoxazoline derivative represented by the following formula [1], an acid addition salt thereof, and a method for preparing the derivative and salt:

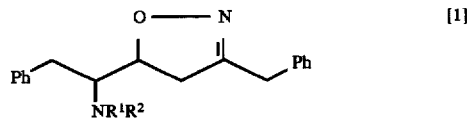

[1]

(wherein Ph represents phenyl; and each of $R^1$ and $R^2$ independently represents hydrogen, acyl, alkyloxycarbonyl, arylalkyloxycarbonyl, aryloxycarbonyl, alkylaminocarbonyl, arylalkylaminocarbonyl, arylaminocarbonyl, alkyl, arylalkyl, aryl, alkylsulfonyl, arylalkylsulfonyl, or arylsulfonyl, or $R^1$ and $R^2$ are linked to each other to represent divalent acyl).

The present invention also provides a mixture of 2-isoxazoline derivatives represented by the following formulas [2] and [3], a mixture of acid addition salts thereof, that is, an acid addition salt of the mixture, and a method for preparing the mixture and the mixture of the salts:

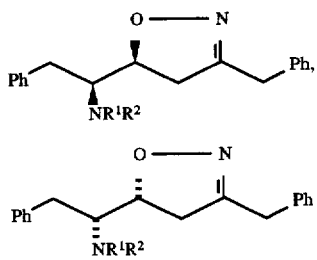

(wherein Ph represents phenyl; and each of $R^1$ and $R^2$ independently represents hydrogen, acyl, alkyloxycarbonyl, arylalkyloxycarbonyl, aryloxycarbonyl, alkylaminocarbonyl, arylalkylaminocarbonyl, arylaminocarbonyl, alkyl, arylalkyl, aryl, alkylsulfonyl, arylalkylsulfonyl, or arylsulfonyl, or $R^1$ and $R^2$ are linked to each other to represent divalent acyl).

The present invention also provides a 2-isoxazoline derivative represented by the following formula [2], an acid addition salt thereof, and a method for preparing the derivative and salt:

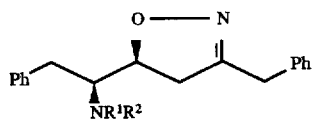

(wherein Ph represents phenyl; and each of $R^1$ and $R^2$ independently represents hydrogen, acyl, alkyloxycarbonyl, arylalkyloxycarbonyl, aryloxycarbonyl, alkylaminocarbonyl, arylalkylaminocarbonyl, arylaminocarbonyl, alkyl, arylalkyl, aryl, alkylsulfonyl, arylalkylsulfonyl, or arylsulfonyl, or $R^1$ and $R^2$ are linked to each other to represent divalent acyl).

The present invention also provides a method for preparing a 2,5-diamino-1,6-diphenyl-3-hydroxyhexane derivative represented by the following formula [6] characterized by reducing a 3-phenylmethyl-5-(1'-amino-2'-phenylethyl)-2-isoxazoline derivative represented by formula [1]:

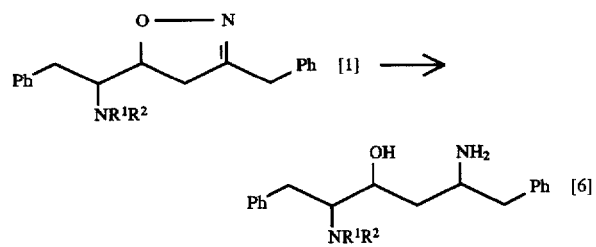

(wherein Ph represents phenyl; and each of $R^1$ and $R^2$ independently represents hydrogen, acyl, alkyloxycarbonyl, arylalkyloxycarbonyl, aryloxycarbonyl, alkylaminocarbonyl, arylalkylaminocarbonyl, arylaminocarbonyl, alkyl, arylalkyl, aryl, alkylsulfonyl, arylalkylsulfonyl, or arylsulfonyl, or $R^1$ and $R^2$ are linked to each other to represent divalent acyl).

The present invention also provides a method for preparing a (2S,3S,5S)-2,5-diamino-1,6-diphenyl-3-hydroxyhexane derivative represented by the following formula [7] and/or a (2S,3S,5R)-2,5-diamino-1,6-diphenyl-3-hydroxyhexane derivative represented by the following formula [8] characterized by reducing a (5S,1'S)-3-phenylmethyl- 5-(1'-amino-2'-phenylethyl)-2-isoxazoline derivative represented by formula [2]:

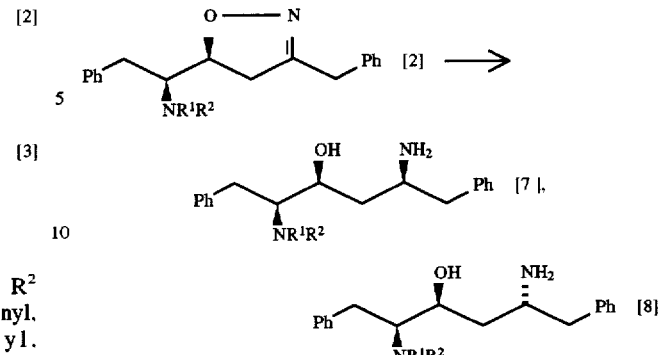

(wherein Ph represents phenyl; and each of $R^1$ and $R^2$ independently represents hydrogen, acyl, alkyloxycarbonyl, arylalkyloxycarbonyl, aryloxycarbonyl, alkylaminocarbonyl, arylalkylaminocarbonyl, arylaminocarbonyl, alkyl, arylalkyl, aryl, alkylsulfonyl, arylalkylsulfonyl, or arylsulfonyl, or $R^1$ and $R^2$ are linked to each other to represent divalent acyl).

DESCRIPTION OF PREFERRED EMBODIMENTS

Since the 2-isoxazoline derivatives of the present invention have an asymmetric carbon atom at the 5- position of a 2-isoxazoline ring, and have an asymmetric carbon atom at the 1'-position of the substituent, 1'-amino-2'-phenyl ethyl (or a group having a substituent on the N atom), which is the substituent at the 5- position of the 2-isoxazoline ring, they assume the following four stereoisomers: (5R,1'R), (5S,1'S), (5R,1'S), and (5S,1'R). Accordingly, the 2-isoxazoline derivatives of the present invention may be present as stereoisomers corresponding to the above situations, and may also be present as mixtures of the stereoisomers in arbitrary ratios. In this specification, it must be understood that each derivative encompasses four stereoisomers and a mixture of them in an arbitrary ratio.

In the above formulas [1], [2], and [3], $R^1$ and $R^2$ are arbitrarily and independently selected from the group consisting of hydrogen, acyl, alkyloxycarbonyl, arylalkyloxycarbonyl, aryloxycarbonyl, alkylaminocarbonyl, arylalkylaminocarbonyl, arylaminocarbonyl, alkyl, arylalkyl, aryl, alkylsulfonyl, arylalkylsulfonyl, and arylsulfonyl. Alternatively, like a phthaloyl group, $R^1$ and $R^2$ may be linked to each other to form a divalent acyl group for cyclizing the group. In the novel 2-isoxazoline derivatives represented by formulas [1], [2], or [3], it is particularly preferred that at least one of $R^1$ and $R^2$ be hydrogen or that $R^1$ and $R^2$ are both arylalkyl.

When $R^1$ or $R^2$ is acyl or when $R^1$ and $R^2$ are linked to each other to form divalent acyl, specific examples of $R^1$ or $R^2$ include formyl, acetyl, propionyl, 2-methylpropionyl, 2,2-dimethylpropionyl, benzoyl, p-methylbenzoyl, p-methoxybenzoyl, p-nitrobenzoyl, phenylacetyl, 2-pyridylmethoxycarbonylvalyl, 3-pyridylmethoxylcarbonylvalyl, 4-pyridylmethoxycarbonylvalyl, 2-pyridylmethylaminocarbonylvalyl, 6-methyl-2-pyridylmethylaminocarbonylvalyl, 2-pyridylmethylaminocarbonylisoleucyl, phthaloyl, succinyl, and maleoyl.

When $R^1$ or $R^2$ is acyl or when $R^1$ and $R^2$ are linked to each other to form divalent acyl, specific examples of resulting compounds include 3-phenylmethyl-5-(1'-formylamino-2'-phenylethyl)-2-isoxazoline, 3-phenylmethyl-5-(1'-acetylamino-2'-phenylethyl)-2-isoxazoline, 3-phenylmethyl-5-(1'-propionylamino-2'-phenylethyl)-2-isoxazoline, 3-phenylmethyl-5-(1'-(2"-methylpropionyl)amino-2'-phenylethyl)-2-isoxazoline, 3-phenylmethyl-5-(1'-(2",2"-dimethylpropionyl)amino-2'-phenylethyl)-2-isoxazoline, 3-phenylmethyl-5-(1'-benzoylamino-2'-phenylethyl)-2-isoxazoline, 3-phenylmethyl-5-(1'-p-methylbenzoylamino-2'-phenylethyl)-2-isoxazoline, 3-phenylmethyl-5-(1'-p-methoxybenzoylamino-2'-phenylethyl)-2-isoxazoline, 3-phenylmethyl-5-(1'-p-nitrobenzoylamino-2'-phenylethyl)-2-isoxazoline, 3-phenylmethyl-5-(1'-phenylacetylamino-2'-phenylethyl)-2-isoxazoline, 3-phenylmethyl-5-(1'-(2"-pyridylmethoxycarbonyl)valylamino-2'-phenylethyl)-2-isoxazoline, 3-phenylmethyl-5-(1'-(3"-pyridylmethoxycarbonyl)valylamino-2'-phenylethyl)-2-isoxazoline, 3-phenylmethyl-5-(1'-(4"-pyridylmethoxycarbonyl)valylamino-2'-phenylethyl)-2-isoxazoline, 3-phenylmethyl-5-(1'-(N-methyl-N-(2"-pyridyl)methyl)aminocarbonylvalylamino-2'-phenylethyl)-2-isoxazoline, 3-phenylmethyl-5-(1'-(N-methyl-N-(6"-methyl-2"-pyridyl)methyl)aminocarbonylvalylamino-2'-phenylethyl)-2-isoxazoline, 3-phenylmethyl-5-(1'-(N-methyl-N-(2"-pyridyl)methyl)aminocarbonylisoleucylamino-2'-phenylethyl)-2-isoxazoline, 3-phenylmethyl-5-(1'-phthalimido-2'-phenylethyl)-2-isoxazoline, 3-phenylmethyl-5-(1'-succinimido-2'-phenylethyl)-2-isoxazoline, and 3-phenylmethyl-5-(1'-maleimido-2'-phenylethyl)-2-isoxazoline.

When $R^1$ or $R^2$ is alkyloxycarbonyl, specific examples of $R^1$ or $R^2$ include methoxycarbonyl, ethoxycarbonyl, propoxycarbonyl, isopropoxycarbonyl, sec-butoxycarbonyl, isobutoxycarbonyl, and tert-butoxycarbonyl.

When $R^1$ or $R^2$ is alkyloxycarbonyl, specific examples of resulting compounds include 3-phenylmethyl-5-(1'-methoxycarbonylamino-2'-phenylethyl)-2-isoxazoline, 3-phenylmethyl-5-(1'-ethoxycarbonylamino-2'-phenylethyl)-2-isoxazoline, 3-phenylmethyl-5-(1'-propoxycarbonylamino-2'-phenylethyl)-2-isoxazoline, 3-phenylmethyl-5-(1'-isopropoxycarbonylamino-2'-phenylethyl)-2-isoxazoline, 3-phenylmethyl-5-(1'-sec-butoxycarbonylamino-2'-phenylethyl)-2-isoxazoline, 3-phenylmethyl-5-(1'-isobutoxycarbonylamino-2'-phenylethyl)-2-isoxazoline, and 3-phenylmethyl-5-(1'-tert-butoxycarbonylamino-2'-phenylethyl)-2-isoxazoline.

When $R^1$ or $R^2$ is arylalkyloxycarbonyl, specific examples of $R^1$ or $R^2$ include benzyloxycarbonyl, p-methylphenylmethoxycarbonyl, p-methoxyphenylmethoxycarbonyl, 2-pyridylmethoxycarbonyl, 3-pyridylmethoxycarbonyl, 4-pyridylmethoxycarbonyl, 1-(3'-pyridyl)ethoxycarbonyl, 2-thiazolylmethoxycarbonyl, 4-thiazolylmethoxycarbonyl, 5-thiazolylmethoxycarbonyl, pyrazinylmethoxycarbonyl, 2-furanylmethoxycarbonyl, and 3-furanylmethoxycarbonyl.

When $R^1$ or $R^2$ is arylalkyloxycarbonyl, specific examples of resulting compounds include 3-phenylmethyl-5-(1'-benzyloxycarbonylamino-2'-phenylethyl)-2-isoxazoline, 3-phenylmethyl-5-(1'-p-methylphenylmethoxycarbonylamino-2'-phenylethyl)-2-isoxazoline, 3-phenylmethyl-5-(1'-p-methoxyphenylmethoxycarbonylamino-2'-phenylethyl)-2-isoxazoline, 3-phenylmethyl-5-(1'-(2"-pyridyl)methoxycarbonylamino-2'-phenylethyl)-2-isoxazoline, 3-phenylmethyl-5-(1'-(3"-pyridyl)methoxycarbonylamino-2'-phenylethyl)-2-isoxazoline, 3-phenylmethyl-5-(1'-(4"-pyridyl)methoxycarbonylamino-2'-phenylethyl)-2-isoxazoline, 3-phenylmethyl-5-(1'-(1"-(3'"-pyridyl) ethoxy)carbonylamino-2'-phenylethyl)-2-isoxazoline, 3-phenylmethyl-5-(1'-(2"-thiazolyl)methoxycarbonylamino-2'-phenylethyl)-2-isoxazoline, 3-phenylmethyl-5-(1'-(4"-thiazolyl)methoxycarbonylamino-2'-phenylethyl)-2-isoxazoline, 3-phenylmethyl-5-(1'-(5"-thiazolyl)methoxycarbonylamino-2'-phenylethyl)-2-isoxazoline, 3-phenylmethyl-5-(1'-pyrazinylmethoxycarbonylamino-2'-phenylethyl)-2-isoxazoline, 3-phenylmethyl-5-(1'-(2"-furanyl)methoxycarbonylamino-2'-phenylethyl)-2-isoxazoline, and 3-phenylmethyl-5-(1'-(3"-furanyl)methoxycarbonylamino-2'-phenylethyl)-2-isoxazoline.

When $R^1$ or $R^2$ is aryloxycarbonyl, specific examples of $R^1$ or $R^2$ include phenoxycarbonyl, p-methylphenoxycarbonyl, p-methoxyphenoxycarbonyl, p-nitrophenoxycarbonyl, 1-naphthyloxycarbonyl, and 2-naphthyloxycarbonyl.

When $R^1$ or $R^2$ is aryloxycarbonyl, specific examples of resulting compounds include 3-phenylmethyl-5-(1'-phenoxycarbonylamino-2'-phenylethyl)-2-isoxazoline, 3-phenylmethyl-5-(1'-p-methylphenoxycarbonylamino-2'-phenylethyl)-2-isoxazoline, 3-phenylmethyl-5-(1'-p-methoxyphenoxycarbonylamino-2'-phenylethyl)-2-isoxazoline, 3-phenylmethyl-5-(1'-p-nitrophenoxycarbonylamino-2'-phenylethyl)-2-isoxazoline, 3-phenylmethyl-5-(1'-(1"-naphthyl)oxycarbonylamino-2'-phenylethyl)-2-isoxazoline, and 3-phenylmethyl-5-(1'-(2"-naphthyl)oxycarbonylamino-2'-phenylethyl)-2-isoxazoline.

When $R^1$ or $R^2$ is alkylaminocarbonyl, specific examples of $R^1$ or $R^2$ include methylaminocarbonyl, ethylaminocarbonyl, propylaminocarbonyl, and isopropylaminocarbonyl.

When $R^1$ or $R^2$ is alkylaminocarbonyl, specific examples of resulting compounds include 3-phenylmethyl-5-(1'-methylaminocarbonylamino-2'-phenylethyl)-2-isoxazoline, 3-phenylmethyl-5-(1'-ethylaminocarbonylamino-2'-phenylethyl)-2-isoxazoline, 3-phenylmethyl-5-(1'-propylaminocarbonylamino-2'-phenylethyl)-2-isoxazoline, 3-phenylmethyl-5-(1'-isopropylaminocarbonylamino-2'-phenylethyl)-2-isoxazoline.

When $R^1$ or $R^2$ is arylalkylaminocarbonyl, specific examples of $R^1$ or $R^2$ include benzylaminocarbonyl, 2-pyridylmethylaminocarbonyl, 3-pyridylmethylaminocarbonyl, and 4-pyridylmethylaminocarbonyl.

When $R^1$ or $R^2$ is arylalkylaminocarbonyl, specific examples of resulting compounds include 3-phenylmethyl-5-(1'-benzylaminocarbonylamino-2'-phenylethyl)-2-isoxazoline, 3-phenylmethyl-5-(1'-(2"-pyridyl)methylaminocarbonylamino-2'-phenylethyl)-2-isoxazoline, 3-phenylmethyl-5-(1'-(3"-pyridyl)methylaminocarbonylamino-2'-phenylethyl)-2-isoxazoline, 3-phenylmethyl-5-(1'-(4"-pyridyl)methylaminocarbonylamino-2'-phenylethyl)-2-isoxazoline, 3-phenylmethyl-5-(1'-(N-methyl-N-(2"-pyridylmethyl))aminocarbonylamino-2'-phenylethyl)-2-isoxazoline, 3-phenylmethyl-5-(1'-(N-methyl-N-(3"-pyridylmethyl))aminocarbonylamino-2'-phenylethyl)-2-isoxazoline, and 3-phenylmethyl-5-(1'-(N-methyl-N-(4"-pyridylmethyl))aminocarbonylamino-2'-phenylethyl)-2-isoxazoline.

When $R^1$ or $R^2$ is arylaminocarbonyl, specific examples of $R^1$ or $R^2$ include phenylaminocarbonyl and p-methoxyphenylaminocarbonyl.

When $R^1$ or $R^2$ is arylaminocarbonyl, specific examples of resulting compounds include 3-phenylmethyl-5-(1'-phenylaminocarbonylamino-2'-phenylethyl)-2-isoxazoline and 3-phenylmethyl-5-(1'-p-methoxyphenylaminocarbonylamino-2'-phenylethyl)-2-isoxazoline.

When $R^1$ or $R^2$ is alkyl, specific examples of $R^1$ or $R^2$ include methyl, ethyl, propyl, and isopropyl.

When $R^1$ or $R^2$ is alkyl, specific examples of resulting compounds include 3-phenylmethyl-5-(1'-methylamino-2'-phenylethyl)-2-isoxazoline, 3-phenylmethyl-5-(1'-ethylamino-2'-phenylethyl)-2-isoxazoline, 3-phenylmethyl-5-(1'-propylamino-2'-phenylethyl)-2-isoxazoline, 3-phenylmethyl-5-(1'-isopropylamino-2'-phenylethyl)-2-isoxazoline, as well as those listed hereinabove for cases in which $R^1$ or $R^2$ is acyl including 3-phenylmethyl-5-(1'-(N-methyl-N-(2"-pyridyl) methyl) aminocarbonylvalylamino-2'-phenylethyl)-2-isoxazoline, 3-phenylmethyl-5-(1'-(N-methyl-N-(6"-methyl)-2"-pyridyl)methyl) aminocarbonylvalylamino-2'-phenylethyl)-2- isoxazoline, 3-phenylmethyl-5-(1'-(N-methyl-N-(2"-pyridyl)methyl) aminocarbonylisoleucylamino-2'-phenylethyl)-2-isoxazoline, and in addition, those listed hereinabove for cases in which $R^1$ or $R^2$ is arylalkylaminocarbonyl including 3-phenylmethyl-5-(1'-(N-methyl-N-(2"-pyridylmethyl)) aminocarbonylamino-2'-phenylethyl)-2-isoxazoline, 3-phenylmethyl-5-(1'-(N-methyl-N-(3"-pyridylmethyl)) aminocarbonylamino-2'-phenylethyl)-2-isoxazoline, and 3-phenylmethyl-5-(1'-(N-methyl-N-(4"-pyridylmethyl)) aminocarbonylamino-2'-phenylethyl)-2-isoxazoline.

When $R^1$ or $R^2$ is arylalkyl, specific examples of $R^1$ or $R^2$ include benzyl, p-methylphenylmethyl, p-methoxyphenylmethyl, and p-nitrophenylmethyl.

When $R^1$ or $R^2$ is arylalkyl, specific examples of resulting compounds include 3-phenylmethyl-5-(1'-benzylamino-2'-phenylethyl)-2-isoxazoline, 3-phenylmethyl-5-(1'-p-methylphenylmethylamino-2'-phenylethyl)-2-isoxazoline, 3-phenylmethyl-5-(1'-p-methoxyphenylmethylamino-2'-phenylethyl)-2-isoxazoline, 3-phenylmethyl-5-(1'-p-nitrophenylmethylamino-2'-phenylethyl)-2-isoxazoline, 3-phenylmethyl-5-(1'-N,N-dibenzylamino-2'-phenylethyl)-2-isoxazoline, 3-phenylmethyl-5-(1'-N,N-bis(p-methylphenylmethyl)amino-2'-phenylethyl)-2-isoxazoline, 3-phenylmethyl-5-(1'-N,N-bis(p-methoxyphenylmethyl) amino-2'-phenylethyl)-2-isoxazoline, and 3-phenylmethyl-5-(1'-N,N-bis(p-nitrophenylmethyl) amino-2'-phenylethyl)-2-isoxazoline.

When $R^1$ or $R^2$ is aryl, specific examples of $R^1$ or $R^2$ include phenyl, p-methylphenyl, p-methoxyphenyl, and p-nitrophenyl.

When $R^1$ or $R^2$ is aryl, specific examples of resulting compounds include 3-phenylmethyl-5-(1'-phenylamino-2'-phenylethyl)-2-isoxazoline, 3-phenylmethyl-5-(1'-p-methylphenylamino-2'-phenylethyl)-2-isoxazoline, 3-phenylmethyl-5-(1'-p-methoxyphenylamino-2'-phenylethyl)-2-isoxazoline, and 3-phenylmethyl-5-(1'-p-nitrophenylamino-2'-phenylethyl)-2-isoxazoline.

When $R^1$ or $R^2$ is alkylsulfonyl, specific examples of $R^1$ or $R^2$ include methylsulfonyl, ethylsulfonyl, propylsulfonyl, and isopropylsulfonyl.

When $R^1$ or $R^2$ is alkylsulfonyl, specific examples of resulting compounds include 3-phenylmethyl-5-(1'-methylsulfonylamino-2'-phenylethyl)-2-isoxazoline, 3-phenylmethyl-5-(1'-ethylsulfonylamino-2'-phenylethyl)-2-isoxazoline, 3-phenylmethyl-5-(1'-propylsulfonylamino-2'-phenylethyl)-2-isoxazoline, and 3-phenylmethyl-5-(1'-isopropylsulfonylamino-2'-phenylethyl)-2-isoxazoline.

When $R^1$ or $R^2$ is arylalkylsulfonyl, specific examples of $R^1$ or $R^2$ include benzylsulfonyl, p-methylphenylmethylsulfonyl, p-methoxyphenylmethylsulfonyl, and p-nitrophenylmethylsulfonyl.

When $R^1$ or $R^2$ is arylalkylsulfonyl, specific examples of resulting compounds include 3-phenylmethyl-5-(1'-benzylsulfonylamino-2'-phenylethyl)-2-isoxazoline, 3-phenylmethyl-5-(1'-p-methylphenylmethylsulfonylamino-2'-phenylethyl)-2-isoxazoline, 3-phenylmethyl-5-(1'-p-methoxyphenylmethylsulfonylamino-2'-phenylethyl)-2-isoxazoline, and 3-phenylmethyl-5-(1'-p-nitrophenylmethylsulfonylamino-2'-phenylethyl)-2-isoxazoline.

When $R^1$ or $R^2$ is arylsulfonyl, specific examples of $R^1$ or $R^2$ include phenylsulfonyl, p-methylphenylsulfonyl, p-methoxyphenylsulfonyl, and p-nitrophenylsulfonyl.

When $R^1$ or $R^2$ is arylsulfonyl, specific examples of resulting compounds include 3-phenylmethyl-5-(1'-phenylsulfonylamino-2'-phenylethyl)-2-isoxazoline, 3-phenylmethyl-5-(1'-p-methylphenylsulfonylamino-2'-phenylethyl)-2-isoxazoline, 3-phenylmethyl-5-(1'-p-methoxyphenylsulfonylamino-2'-phenylethyl)-2-isoxazoline, and 3-phenylmethyl-5-(1'-p-nitrophenylsulfonylamino-2'-phenylethyl)-2-isoxazoline.

Acid addition salts of the 2-isoxazoline derivatives of the present invention may be arbitrarily selected from the salts derived from reactions with inorganic acids or organic acids. Acid addition salts may also be adducts with an organic solvent or water at an arbitrary molar ratio. The molar ratio of a novel 2-isoxazoline derivative represented by formula [1], [2], or [3] to an acid may be determined so that an acid addition salt is obtained from the reaction of the derivative and acid.

Examples of acid addition salts derived from inorganic acids include hydrochlorides, hydrobromides, hydroiodides, sulfates, hydrogensulfates, phosphates, monohydrogenphosphates, dihydrogenphosphates, nitrates, and thiocyanates.

Examples of acid addition salts derived from organic acids include carboxylate, sulfonate, and phosphonates. Examples of acid addition salts derived from carboxylic acid include formates, acetates, propionates, butyrates, isobutyrates, cinnamates, benzoates, p-methylbenzoates, p-methoxybenzoates, p-nitrobenzoates, phenylacetates, lactates, oxalates, malonates, succinates, glutarates, adipates, maleates, fumarates, phthalates, terephthalates, citrates, malates, tartarates, salicylates, nicotinates, mandelates and salts from amino acids (such as glycine, alanine, aspartic acid, and glutamic acid). Examples of acid addition salts derived from sulfonic acid include methanesulfonates, ethanesulfonates, benzenesulfonates, p-toluenesulfonates, p-chlorobenzenesulfonates, p-bromobenzenesulfonates, 2-naphthalenesulfonates, and camphorsulfonates. Examples of acid addition salts derived from phosphonic acid include methylphosphonates and phenylphosphonates.

Preferred examples of the novel 2-isoxazoline derivatives of the present invention represented by formulas [1], [2], or [3] include the following:

(5RS,1'RS)-3-phenylmethyl-5-(1'-amino-2'-phenylethyl)-2-isoxazoline; (5RS,1'RS)-3-phenylmethyl-5-(1'-formylamino-2'-phenylethyl)-2-isoxazoline; (5RS,1'RS)-3-phenylmethyl-5-(1'-acetylamino-2'-phenylethyl)-2-isoxazoline; (5RS,1'RS)-3-phenylmethyl-5-(1'-benzoylamino-2'-phenylethyl)-2- isoxazoline; (5RS,1'RS)-3-phenylmethyl-5-(1'-tert-butoxycarbonylamino-2'-phenylethyl)-2-isoxazoline; (5RS,1'RS)-3-phenylmethyl-5-(1'-benzyloxycarbonylamino-2'-phenylethyl)-2-isoxazoline; (5RS,1'RS)-3-phenylmethyl-5-(1'-methoxycarbonylamino-2'-phenylethyl)-2-isoxazoline; (5RS,1'RS)-3-phenylmethyl-5-(1'-phthalimido-2'-phenylethyl)-2-isoxazoline; (5RS,1'RS)-3-phenylmethyl-5-(1'-N,N-dibenzylamino-2'-phenylethyl)-2-isoxazoline; (5RS,1'RS)-3-phenylmethyl-5-(1'-amino-2'-phenylethyl)-2-isoxazoline hydrochloride; (5RS,1'RS)-3-phenylmethyl-5-(1'-amino-2'-phenylethyl)-2-isoxazoline p-toluenesulfonate; (5RS,1'RS)-3-phenylmethyl-5-(1'-amino-2'-phenylethyl)-2-isoxazoline benzenesulfonate; (5RS,1'RS)-3-phenylmethyl-5-(1'-amino-2-phenylethyl)-2-isoxazoline methanesulfonate; (5RS,1'RS)-3-phenylmethyl-5-(1'-amino-2'-phenylethyl)-2-isoxazoline oxalate; (5RS,1'RS)-3-phenylmethyl-5-(1'-amino-2'-phenylethyl)-2-isoxazoline benzoate; (5S,1'S)-3-phenylmethyl-5-(1'-amino-2'-phenylethyl)-2-isoxazoline; (5S,1'S)-3-phenylmethyl-5-(1'-formylamino-2'-phenylethyl)-2-isoxazoline; (5S,1'S)-3-phenylmethyl-5-(1'-acetylamino-2'-phenylethyl)-2-isoxazoline; (5S,1'S)-3-phenylmethyl-5-(1'-benzoylamino-2'-phenylethyl)-2-isoxazoline; (5S,1'S)-3-phenylmethyl-5-(1'-tert-butoxycarbonylamino-2'-phenylethyl)-2-isoxazoline; (5S,1'S)-3-phenylmethyl-5-(1'-benzyloxycarbonylamino-2'-phenylethyl)-2-isoxazoline; (5S,1'S)-3-phenylmethyl-5-(1'-methoxycarbonylamino-2'-phenylethyl)-2-isoxazoline; (5S,1'S)-3-phenylmethyl-5-(1'-phthalimido-2'-phenylethyl)-2-isoxazoline; (5S,1'S)-3-phenylmethyl-5-(1'-N,N-dibenzylamino-2'-phenylethyl)-2-isoxazoline;

(5S,1'S)-3-phenylmethyl-5-(1'-amino-2'-phenylethyl)-2-isoxazoline hydrochloride; (5S,1'S)-3-phenylmethyl-5-(1'-amino-2'-phenylethyl)-2-isoxazoline p-toluenesulfonate; (5S,1'S)-3-phenylmethyl-5-(1'-amino-2'-phenylethyl)-2-isoxazoline benzenesulfonate; (5S,1'S)-3-phenylmethyl-5-(1'-amino-2'-phenylethyl)-2-isoxazoline methanesulfonate; (5S,1'S)-3-phenylmethyl-5-(1'-amino-2'-phenylethyl)-2-isoxazoline oxalate; (5S,1'S)-3-phenylmethyl-5-(1'-amino-2'-phenylethyl)-2-isoxazoline benzoate; (5S,1'S)-3-phenylmethyl-5-(1'-amino-2'-phenylethyl)-2-isoxazoline (S)-mandelate; and (5R,1'R)-3-phenylmethyl-5-(1'-amino-2'-phenylethyl)-2-isoxazoline (R)-mandelate.

2-Isoxazoline derivatives represented by formula [1], [2], or [3], or their acid addition salts may be synthesized from other 2-isoxazoline derivatives or their acid addition salts by substitution of $R^1$ and/or $R^2$, neutralization, acid-addition or by combination of these procedures.

For example, when a 2-isoxazoline derivative represented by formula [1], [2], or [3] in which at least one of $R^1$ and $R^2$ is hydrogen, or an acid addition salt of such a derivative is treated with a reagent capable of introducing a group other than hydrogen, it is possible to obtain a 2-isoxazoline derivative represented by formula [1], [2], or [3] or an acid addition salt thereof in which at least one of $R^1$ and $R^2$ has been converted into a group other than hydrogen, which falls within the scope of the present invention.

Alternatively, when a 2-isoxazoline derivative represented by formula [1], [2], or [3] in which at least one of $R^1$ and $R^2$ is a group other than hydrogen, or an acid addition salt of such a derivative is treated under conditions that permit removal of the group other than hydrogen, for example, by treatment with an acid or a base, oxidation or reduction, it is possible to obtain a 2-isoxazoline derivative represented by formula [1], [2], or [3] or an acid addition salt thereof in which at least the group other than hydrogen has been converted into hydrogen, which falls within the scope of the present invention.

When 2-isoxazoline derivative represented by formula [1], [2], or [3] is processed with an acid, a corresponding acid addition salt can be obtained.

Also, when an acid addition salt of 2-isoxazoline derivative represented by formula [1], [2], or [3] is processed with an inorganic base (such as NaOH, KOH, etc.) or an organic base (such as triethylamine, diisopropylamine, etc., that is, when the acid added to the salt is neutralized, a corresponding 2-isoxazoline derivative is obtained.

The above-mentioned treatments may be combined with one another. Illustrative examples of treatments will next be described below.

By reacting 3-phenylmethyl-5-(1'-amino-2'-phenylethyl)-2-isoxazoline with a formylating agent (e.g., formic acid, ethyl formate, etc.), an acetylating agent (e.g., acetic anhydride, acetyl chloride, etc.), a benzoylating agent (e.g., benzoyl chloride, etc.), a phthaloylating agent (e.g., N-carbethoxylphthalimido, phthalic anhydride, etc.), a methoxycarbonylating agent (e.g., methyl chloroformate, dimethyl dicarbonate, etc.), tert-butoxycarbonylating agent (e.g., di-tert-butyl dicarbonate, etc.), a benzyloxycarbonylating agent (e.g., benzyl chloroformate, etc.), or with a benzylating agent (e.g., benzyl chloride, benzyl bromide, etc.), it is possible to obtain corresponding 3-phenylmethyl-5-(1'-formylamino-2'-phenylethyl)-2-isoxazoline, 3-phenylmethyl-5-(1'-acetylamino-2'-phenylethyl)-2-isoxazoline, 3-phenylmethyl-5-(1'-benzoylamino-2'-phenylethyl)-2-isoxazoline, 3-phenylmethyl-5-(1'-phthalimido-2'-phenylethyl)-2-isoxazoline, 3-phenylmethyl-5-(1'-methoxycarbonylamino-2'-phenylethyl)-2-isoxazoline, 3-phenylmethyl-5-(1'-tert-butoxycarbonylamino-2'-phenylethyl)-2-isoxazoline, 3-phenylmethyl-5-(1'-benzyloxycarbonylamino-2'-phenylethyl)-2-isoxazoline, and 3-phenylmethyl-5-(1'-N,N-dibenzylamino-2'-phenylethyl)-2-isoxazoline.

Also, by treating 3-phenylmethyl-5-(1'-formylamino-2'-phenylethyl)-2-isoxazoline, 3-phenylmethyl-5-(1'-tert-butoxycarbonylamino-2'-phenylethyl)-2-isoxazoline, or 3-phenylmethyl-5-(1'-benzyloxycarbonylamino-2'-phenylethyl)-2-isoxazoline, with an acid such as hydrochloric acid, trifluoroacetic acid, or p-toluenesulfonic acid, and then with a base, 3-phenylmethyl-5-(1'-amino-2'-phenylethyl)-2-isoxazoline can be obtained.

By treating 3-phenylmethyl-5-(1'-phthalimido-2'-phenylethyl)-2-isoxazoline with hydrazine, methylamine, etc., 3-phenylmethyl-5-(1'-amino-2'-phenylethyl)-2-isoxazoline can be obtained.

By treating 3-phenylmethyl-5-(1'-amino-2'-phenylethyl)-2-isoxazoline with hydrochloric acid, p-toluenesulfonic acid, benzenesulfonic acid, methanesulfonic acid, oxalic acid, benzoic acid, (S)-mandelic acid, or (R)-mandelic acid, it is possible to obtain corresponding 3-phenylmethyl-5-(1'-amino-2'-phenylethyl)-2-isoxazoline hydrochloride, 3-phenylmethyl-5-(1'-amino-2'-phenylethyl)-2-isoxazoline p-toluenesulfonate, 3-phenylmethyl-5-(1'-amino-2'-phenylethyl)-2-isoxazoline benzenesulfonate, 3-phenylmethyl-5-(1'-amino-2'-phenylethyl)-2-isoxazoline methanesulfonate, 3-phenylmethyl-5-(1'-amino-2'-phenylethyl)-2-isoxazoline oxalate, 3-phenylmethyl-5-(1'- amino-2'-phenylethyl)-2-isoxazoline benzoate, 3-phenylmethyl-5-(1'-amino-2'-phenylethyl)-2-isoxazoline (S)-mandelate, or 3-phenylmethyl-5-(1'-amino-2'-phenylethyl)-2-isoxazoline (R)-mandelate. When these acid addition salts are treated with an inorganic base such as NaOH or an organic base such as triethylamine, 3-phenylmethyl-5-(1'-amino-2'-phenylethyl)-2-isoxazoline can be obtained.

By treating 3-phenylmethyl-5-(1'-formylamino-2'-phenylethyl)-2-isoxazoline or 3-phenylmethyl-5-(1'-tert-butoxycarbonylamino-2'-phenylethyl)-2-isoxazoline with hydrochloric acid or p-toluenesulfonic acid, 3-phenylmethyl-5-(1'-amino-2'-phenylethyl)-2-isoxazoline hydrochloride or 3-phenylmethyl-5-(1'-amino-2'-phenylethyl)-2-isoxazoline p-toluenesulfonate can be obtained.

The novel 2-isoxazoline derivatives represented by formula [1], [2], or [3] can be synthesized by reacting a compound of formula [4] or [5] with phenylacetonitrile oxide:

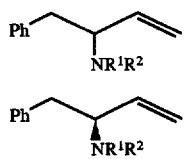

(wherein Ph represents phenyl; and each of $R^1$ and $R^2$ independently represents hydrogen, acyl, alkyloxycarbonyl, arylalkyloxycarbonyl, aryloxycarbonyl, alkylaminocarbonyl, arylalkylaminocarbonyl, arylaminocarbonyl, alkyl, arylalkyl, aryl, alkylsulfonyl, arylalkylsulfonyl, or arylsulfonyl, or $R^1$ and $R^2$ are linked to each other to represent divalent acyl).

The compounds of [4] or [5] can be synthesized using known methods. For example, it is known that (S)-3-tert-butoxycarbonylamino-4-phenyl-1-butene can be obtained from the reaction of (S)-tert-butoxycarbonylphenylalaninal and methylidene triphenylphosphorane which is obtainable from a reaction using methyltriphenylphosphonium bromide and a base such as butyl lithium (see, for example, JP-A-61-33152, J. Org. Chem., 1987, 52, 1487, and JP-A-2-191243). Also, it is known that (S)-3-amino-4-phenyl-1-butene can be obtained by reacting (2RS,3S)-2-hydroxy-3-tert-butoxycarbonylamino-4-phenyl-1-trimethylsilylbutane with an ether complex of boron trifluoride (see, for example, JP-A-4-257520 and J. Med. Chem., 1992, 35, 1685). It is also known that 3-trichloroacetylamino-4-phenyl-1-butene can be obtained by heating, in xylene, trichloroacetoimidato obtained from the reaction of 4-phenyl-2-butene-1-ol and trichloroacetonitrile (see, for example, JP-A-61-22055 and J. Chem. Soc. Chem. Commun., 1984, 770). Moreover, it is known that 3-benzylamino-4-phenyl-1-butene can be obtained by reacting 3-benzylamino-4-phenyl-1-butyne with hydrogen in the presence of a Lindlar catalyst (J. Chem. Soc. Perkin Trans. 1, 1983, 387). Furthermore, it is known that (S)-3-tert-butoxycarbonylamino-4-phenyl-1-butene can be obtained by reacting (S)-3-tert-butoxycarbonylamino-4-phenylbutylo-nitrophenylselenide with aqueous hydrogen peroxide (Heterocycles, 1989, 29, 1835).

On the other hand, phenylacetonitrile oxide can be synthesized by a conventional method for synthesizing nitrile oxide, e.g., by a method described in Kurt B. G. Torssell, "Nitrile Oxides, Nitrones, and Nitronates in Organic Synthesis" (VCH Publishers, Inc., New York, 1988).

It is known that phenylacetonitrile oxide can be obtained by reacting phenylacetohydroximoyl chloride with triethylamine (see, for example, Gazz. Chim. Ital., 1980, 110, 341 and J. Org. Chem., 1988, 53, 2426). It is also known that phenylacetonitrile oxide can be obtained by reacting 2-phenylnitroethane with phenylisocyanate in the presence of triethylamine (J. Chem. Soc. Chem. Commun., 1982, 291). It is also known that phenylacetonitrile oxide can be obtained by reacting phenylacetoaldehyde oxime with dimethyidioxirane (Journal of the Chemical Society of Japan, Chemistry and Industrial Chemistry, 1992, 420).

Although it is possible to perform the reaction of a compound [4] or [5] and phenylacetonitrile oxide after phenylacetonitrile oxide is isolated, phenylacetonitrile oxide generated in situ may be reacted with a compound [4] or [5], because phenylacetonitrile oxide is unstable as are the case with nitrile oxides in general. In view of the yield of reaction and operability, it is advantageous to react phenylacetonitrile oxide generated in situ.

Suitable methods for generating phenylacetonitrile oxide include a method in which a precursor of phenylacetonitrile oxide (for example, phenylacetohydroximoyl chloride, 2-phenylnitroethane, and phenylacetaldehyde oxime) or the other reagents (for example, triethylamine, phenylisocyanate, and dimethyidioxirane) are added to the reaction system at a suitable rate.

The compounds [4] or [5] which are reacted with phenylacetonitrile oxide are not particularly limited so long as side reactions are negligible in practice. In order to avoid side reactions between —$NR^1R^2$ at the 3-position of compound [4] or [5] and phenylacetonitrile oxide, it is preferred that at least one of $R^1$ and $R^2$ be an electron attractive group, or that $R^1$ and $R^2$ are both groups other than hydrogen. Examples of $R^1$ and $R^2$ of compounds [4] and [5] coincide with those listed for compounds [1]. In cases where at least one of $R^1$ or $R^2$ is an electron attractive group, examples of preferred species of $R^1$ and $R^2$ include acyl, alkyloxycarbonyl, arylalkyloxycarbonyl, aryloxycarbonyl, alkylaminocarbonyl, arylalkylaminocarbonyl, arylaminocarbonyl, alkylsulfonyl, arylalkylsulfonyl, and arylsulfonyl, and those pairs of $R^1$ and $R^2$ which link to each other to form a divalent acyl group. In view of readiness of post-treatment of reaction, preferred $R^1$ and $R^2$ are acyl, alkyloxycarbonyl, arylalkyloxycarbonyl, aryloxycarbonyl, and a pair of $R^1$ and $R^2$ which link to each other to form a divalent acyl group.

If $R^1$ and $R^2$ are both groups other than hydrogen, no particular limitation is imposed on $R^1$ and $R^2$. However, in view of readiness of post-treatment of reaction, it is preferred that $R^1$ and $R^2$ be both arylalkyl.

Specific examples of the above-mentioned acyl or divalent acyl groups each formed of $R^1$ and $R^2$ linked to each other are formyl, acetyl, propionyl, 2-methylpropionyl, 2,2-dimethylpropionyl, benzoyl, p-methylbenzoyl, p-methoxybenzoyl, p-nitrobenzoyl, phenylacetyl, 2-pyridylmethoxycarbonylvalyl, 3-pyridylmethoxycarbonylvalyl, 4-pyridylmethoxycarbonylvalyl, 2-pyridylmethylaminocarbonylvalyl, 6-methyl-2-pyridylmethylaminocarbonylvalyl, 2-pyridylmethylaminocarbonylisoleucyl, phthaloyl, succinyl, maleoyl, etc. For convenience of processing after reaction and in view of prices of reagents, the following groups are preferred: formyl, acetyl, propionyl, 2-methylpropionyl, 2,2-dimethylpropionyl, benzoyl, p-methylbenzoyl, p-methoxybenzoyl, p-nitrobenzoyl, phenylacetyl, phthaloyl, succinyl, and maleoyl. Illustrative examples of compounds providing these groups include 4-phenyl-3-formylamino-1-butene, 4-phenyl-3-acetylamino-1-butene, 4-phenyl-3-propionylamino-1- butene, 4-phenyl-3-(2'-methylpropionyl)amino-1-butene, 4-phenyl-3-(2',2'-dimethylpropionyl)amino-1-butene, 4-phenyl-3-benzoylamino-1-butene, 4-phenyl-3-(p-methylbenzoyl)amino-1-butene, 4-phenyl-3-(p-methoxybenzoyl)amino-1-butene, 4-phenyl-3-(p-nitrobenzoyl)amino-1-butene, 4-phenyl-3-phenylacetylamino-1-butene, 4-phenyl-3-phthalimido-1-butene, 4-phenyl-3-succinimido-1-butene, and 4-phenyl-3-maleimido-1-butene.

Specific examples of the alkyloxycarbonyl group are methoxycarbonyl, ethoxycarbonyl, propoxycarbonyl, isopropoxycarbonyl, sec-butoxycarbonyl, isobutoxycarbonyl, and tert-butoxycarbonyl. For convenience of processing after reaction and in view of prices of reagents, the following groups are preferred: methoxycarbonyl, ethoxycarbonyl, isopropoxycarbonyl, isobutoxycarbonyl, and tert-butoxycarbonyl. Illustrative examples of compounds providing these groups include 4-phenyl-3-methoxycarbonylamino-1-butene, 4-phenyl-3-ethoxycarbonylamino-1-butene, 4-phenyl-3-isopropoxycarbonylamino-1-butene, 4-phenyl-3-isobutoxycarbonylamino-1-butene, and 4-phenyl-3-tert-butoxycarbonylamino-1-butene.

Specific examples of the above-mentioned arylalkyloxycarbonyl group include benzyloxycarbonyl, p-methylphenylmethoxycarbonyl, p-methoxyphenylmethoxycarbonyl, 2-pyridylmethoxycarbonyl, 3-pyridylmethoxycarbonyl, 4-pyridylmethoxycarbonyl, 1-(3'-pyridyl)ethoxycarbonyl, 2-thiazolylmethoxycarbonyl, 4-thiazolylmethoxycarbonyl, 5-thiazolylmethoxycarbonyl, pyrazinylmethoxycarbonyl, 2-furanylmethoxycarbonyl, and 3-furanylmethoxycarbonyl. For convenience of processing after reaction and in view of prices of reagents, the following groups are preferred: benzyloxycarbonyl, p-methylphenylmethoxycarbonyl, and p-methoxyphenylmethoxycarbonyl. Illustrative examples of compounds providing these groups include 4-phenyl-3-benzyloxycarbonylamino-1-butene, 4-phenyl-3-(p-methylphenylmethoxycarbonyl)amino-1-butene, and 4-phenyl-3-(p-methoxyphenylmethoxycarbonyl)amino-1-butene.

Specific examples of the above-mentioned aryloxycarbonyl group are phenoxycarbonyl, p-methylphenoxycarbonyl, p-methoxyphenoxycarbonyl, p-nitrophenoxycarbonyl, 1-naphthyloxycarbonyl, and 2-naphthyloxycarbonyl. For convenience of processing after reaction and in view of prices of reagents, the following groups are preferred: phenoxycarbonyl, p-methylphenoxycarbonyl, p-methoxyphenoxycarbonyl, and p-nitrophenoxycarbonyl. Illustrative compounds providing these groups include 4-phenyl-3-phenoxycarbonylamino-1-butane, 4-phenyl-3-(p-methylphenoxycarbonyl)amino-1-butene, 4-phenyl-3-(p-methoxyphenoxycarbonyl)amino-1-butene, and 4-phenyl-3-(p-nitrophenoxycarbonyl)amino-1-butene.

When $R^1$ and $R^2$ are both arylalkyl, examples of such arylalkyl groups include benzyl, p-methylphenylmethyl, p-methoxyphenylmethyl, and p-nitrophenylmethyl. In view of readiness of post-treatment of reaction and costs of reagents, benzyl and p-methoxyphenylmethyl are preferred. Specifically, 4-phenyl-3-N,N-dibenzylamino-1-butene and 4-phenyl-3-N,N-bis(p-methoxyphenylmethyl)amino-1-butene are mentioned.

The amount of phenylacetonitrile oxide or its precursors are generally 0.2–50 times, preferably 1–20 times, and particularly preferably 1–5 times, by mol, that of compound [4] or [5].

The reaction is performed in the temperature range of −50° C. to as high as the boiling point of the solvent used in the reaction at the reaction pressure (up to approximately 200° C.), preferably between −20° and 120° C., and more preferably between −10° and 80° C. If the reaction temperature is excessively low, reaction rate tends to retard, whereas if it is excessively high, selectivity of reaction tends to become poor. The reaction time is not particularly limited. It is generally between 0.5 and 100 hours. The reaction pressure is not particularly limited, either. It is generally 0.1–50 atm, and preferably 1–50 atm.

No particular limitation is imposed on reaction solvents so far as they do not affect the reaction. Examples of solvents used in the present invention include water, alcohols (e.g., methanol, ethanol, propanol, isopropyl alcohol, butanol, and tert-butyl alcohol), ethers (e.g., diethyl ether, diisopropyl ether, dibutyl ether, tetrahydrofuran, dioxane, and 1,2-dimethoxyethane), nitriles (e.g., acetonitrile), esters (e.g., methyl acetate and ethyl acetate), hydrocarbons (e.g., hexane, heptane, benzene, toluene, and xylene), halogenated hydrocarbons (e.g., methylene chloride, chloroform, 1,2-dichloroethane, and chlorobenzene), ketones (e.g., acetone and methyl ethyl ketone), carboxylic acids (e.g., formic acid, acetic acid, and propionic acid), nitromethane, pyridine, dimethylsulfoxide, N,N-dimethylformamide, and N,N-dimethylacetamide. These solvents are used singly or as a mixture. For convenience of processing after reaction and in view of costs, it is preferred that ethers, hydrocarbons, or mixtures of one of ethers or hydrocarbons and water be used. Particularly, hydrocarbons and mixtures of a hydrocarbon and water are preferred.

Purification methods after reaction may be ordinary ones (such as recrystallization, chromatography, and distillation). Recrystallization is particularly preferred in view that the operation is simple and that the production scale can be easily expanded. Among a number of recrystallization methods, a method which performs crystallization of acid addition salts of 2-isoxazoline derivatives represented by formula [1], [2], or [3] is effective, as it provides high purification efficiency by permitting a reaction byproduct diphenylfuroxane to be removed with ease. Moreover, high crystallization efficiency can be attained if acid addition salts of the derivatives in which $R^1$ and $R^2$ of formula [1], [2], or [3] are both hydrogen atoms are recrystallized. Acid addition salts to be submitted to a purification step may be arbitrarily selected from salts derived from inorganic acids or organic acids. They may be adducts resulting from addition of organic solvents or water.

Examples of acid addition salts derived from inorganic salts include hydrochlorides, hydrobromides, hydroiodides, sulfates, hydrogensulfates, phosphates, monohydrogenphosphates, dihydrogenphosphates, nitrates, and thiocyanates.

Examples of acid addition salts derived from organic acids include carboxylic acids, sulfonic acids, and phosphonic acids. Examples of acid addition salts derived from carboxylic acid include formates, acetates, propionates, butyrates, isobutyrates, cinnamates, benzoates, p-methylbenzoates, p-methoxybenzoates, p-nitrobenzoates, phenylacetates, lactates, oxalates, malonates, succinates, glutarates, adipates, maleates, fumarates, phthalates, terephthalates, citrates, malates, tartarates, salicylates, nicotinates, mandelates, and salts from amino acids (such as glycine, alanine, aspartic acid, and glutamic acid). Examples of acid addition salts derived from sulfonic acid include methanesulfonates, ethanesulfonates, benzenesulfonates, p-toluenesulfonates, p-chlorobenzenesulfonates, p-bromobenzenesulfonates, 2-naphthalenesulfonates, and camphorsulfonates. Examples of acid addition salts derived from phosphonic acid include methylphosphonates and phenylphosphonates.

The amount of acids used is usually 0.2–10 times, preferably 0.3–5 times, and more preferably 0.4–2 times, by mol, that of 2-isoxazoline represented by formula [1], [2], or [3].

When acid addition salts of (5RS,1'RS)-3-phenylmethyl-5-(1'-amino-2'-phenylethyl)-2-isoxazoline are obtained from acid addition salts of a mixture of (5RS,1'RS)-and (5RS,1'SR)-isomers or when acid addition salts of (5S,1'S)-3-phenylmethyl-5-(1'-amino-2'-phenylethyl)-2-isoxazoline are obtained from acid addition salts of a mixture of (5S,1'S)-and (5R,1'S)-isomers, use of hydrochlorides or p-toluenesulfonates is preferred from the viewpoints of purification effects and costs.

Solvents for use in purification are not particularly limited so long as they do not react with 2-isoxazoline derivatives represented by formula [1], [2], or [3], and acid addition salts of 2-isoxazoline derivatives represented by formula [1], [2], or [3] precipitate therefrom. Examples of such solvents include water, alcohols (e.g., methanol, ethanol, propanol, isopropyl alcohol, butanol, and tert-butyl alcohol), ethers (e.g., diethyl ether, diisopropyl ether, dibutyl ether, tetrahydrofuran, dioxane, and 1,2-dimethoxyethane), nitriles (e.g., acetonitrile), esters (e.g., methyl acetate and ethyl acetate), hydrocarbons (e.g., hexane, heptane, benzene, toluene, and xylene), halogenated hydrocarbons (e.g., methylene chloride, chloroform, 1,2-dichloroethane, and chlorobenzene), ketones (e.g., acetone and methyl ethyl ketone), carboxylic acids (e.g., formic acid, acetic acid, and propionic acid), nitromethane, pyridine, dimethylsulfoxide, N,N-dimethylformamide, and N,N-dimethylacetamide. These solvents are used singly or as a mixture. For convenience of processing after reaction and in view of costs, it is preferred that water, alcohols, ethers, nitriles, esters, hydrocarbons, or mixtures of them be used. Acid addition salts which precipitated are subjected to filtration and dried, if necessary, to obtain the desired acid addition salts.

From the novel 2-isoxazoline derivatives of the present invention represented by formula [1], [2], or [3] or from acid addition salts of the derivatives, 2,5-diamino- 1,6-diphenyl-3-hydroxyhexane derivatives can be derived. The latter derivatives can be used as intermediates in the synthesis of medicines such as retrovirus protease inhibitors. In the process of preparing a (2S,3S,5S)-2,5-diamino-1,6-diphenyl-3-hydroxyhexane derivative, which is a significant compound among a number of 2,5-diamino-1,6-diphenyl-3-hydroxyhexane derivatives, optically active 2-isoxazoline derivatives represented by formula [2] and their acid addition salts are particularly important.

Several methods are feasible for preparing optically active 2-isoxazoline derivatives represented by formula [2] or their acid addition salts, including a method in which an optically active compound represented by formula [5] is used as a starting material and a method in which the mixture of (5RS,1'RS)-and (5RS,1'SR)-isomers of 2-isoxazoline derivatives or their acid addition salts, or (5RS,1'RS)-2-isoxazoline derivatives or their acid addition salts are subjected to a procedure such as a optical resolution procedure for obtaining optically active compounds. In a similar way, it is possible to obtain optically active 2-isoxazoline derivatives represented by formula [3] or their acid addition salts.

Among methods for obtaining optically active compounds by optical resolution operation, there is a method described below in which an optically active acid is used.

Although optically active acids are not particularly limited which may be used in the reaction of a mixture of 2-isoxazoline derivatives of formulas [2] and [3] or a mixture of acid addition salts thereof and an optically active acid for obtaining optically active acid addition salts of 2-isoxazoline derivatives represented by formula [2], optically active carboxylic acid and optically active sulfonic acid are advantageously used. Specific examples of optically active carboxylic acids include lactic acid, tartaric acid, malic acid, mandelic acid, amino acids (such as alanine, valine, aspartic acid, and glutamic acid), and their derivatives. Examples of optically active sulfonic acids include camphorsulfonic acid. From the viewpoints of purification efficiency and costs, in order to obtain an acid addition salt of (5S,1'S)-3-phenylmethyl-5-(1'-amino-2'-phenylethyl)-2-isoxazoline, it is preferred that (S)-mandelic acid be used as the optically active acid. On the other hand, in order for an acid addition salt of (5R,1'R)-3-phenylmethyl-5-(1'-amino-2'-phenylethyl)-2-isoxazoline to be obtained, it is preferred that (R)-mandelic acid be used as the optically active acid.

The amount of acids used is usually 0.2–10 times, preferably 0.3–5 times, and more preferably 0.4–2 times, by mol, that of the 2-isoxazoline derivative represented by formula [2] or [3].

Solvents used on this occasion are not particularly limited so long as acid addition salts of 2-isoxazoline derivatives represented by formula [2] or [3] precipitate therefrom. Examples of such solvents include water, alcohols (e.g., methanol, ethanol, propanol, isopropyl alcohol, butanol, and tert-butyl alcohol), ethers (e.g., diethyl ether, diisopropyl ether, dibutyl ether, tetrahydrofuran, dioxane, and 1,2-dimethoxyethane), nitriles (e.g., acetonitrile), esters (e.g., methyl acetate and ethyl acetate), hydrocarbons (e.g., hexane, heptane, benzene, toluene, and xylene), halogenated hydrocarbons (e.g., methylene chloride, chloroform, 1,2-dichloroethane, and chlorobenzene), ketones (e.g., acetone and methyl ethyl ketone), nitromethane, pyridine, dimethylsulfoxide, N,N-dimethylformamide, and N,N-dimethylacetamide. These solvents are used singly or as a mixture. For convenience of processing after reaction and in view of costs, it is preferred that water, alcohols, ethers, nitriles, esters, hydrocarbons, or mixtures of them be used. Particularly, water, alcohols, hydrocarbons, and mixtures of them are preferred.

When optically active acid addition salts which precipitated are subjected to filtration and dried, if necessary, the desired optically active acid addition salts can be obtained. By processing the thus-obtained optically active acid addition salts with an inorganic base (such as NaOH and KOH) or an organic base (such as triethylamine and diisopropylethylamine), in other words, by neutralizing the acid which has been added, corresponding optically active 2-isoxazoline derivatives can be obtained.

The novel 2-isoxazoline derivatives represented by formula [1], [2], or [3] or acid addition salts of the derivatives can be converted to 2,5-diamino-1,6-diphenyl-3-hydroxyhexane derivatives which are intermediates in the synthesis of medicines such as retrovirus protease inhibitors by using a conventional method such as a method described by Kurt B. G. Torssell ("Nitrile Oxides, Nitrones, and Nitronates in Organic Synthesis" (VCH Publishers, Inc., New York, 1988)).

However, by reducing the novel 2-isoxazoline derivatives of formula [1] or [2] in accordance with the present invention, 2,5-diamino-1,6-diphenyl-3-hydroxyhexane derivatives represented by formula [6], or (2S,3S,5S)-2,5-diamino-1,6-diphenyl-3-hydroxyhexane derivatives represented by formula [7] and/or (2S,3S,5R)-2,5-diamino-1,6-diphenyl-3-hydroxyhexane derivatives represented by formula [8], can be synthesized advantageously in an industrial scale.

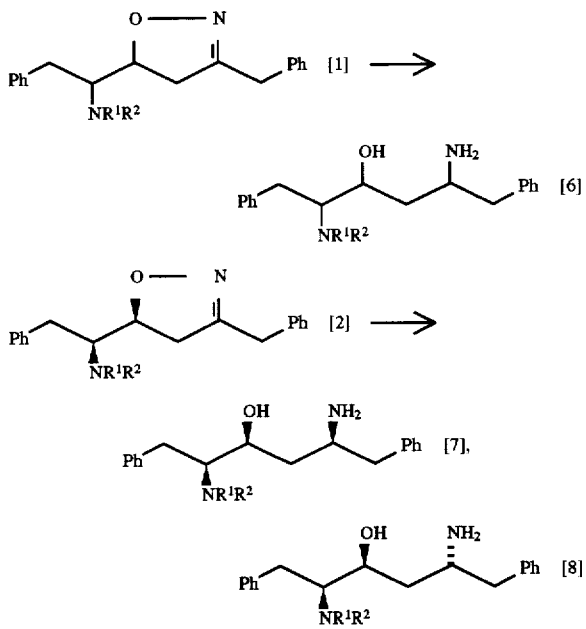

(wherein Ph represents phenyl; and each of $R^1$ and $R^2$ independently represents hydrogen, acyl, alkyloxycarbonyl, arylalkyloxycarbonyl, aryloxycarbonyl, alkylaminocarbonyl, arylalkylaminocarbonyl, arylaminocarbonyl, alkyl, arylalkyl, aryl, alkylsulfonyl, arylalkylsulfonyl, or arylsulfonyl, or $R^1$ and $R^2$ are linked to each other to represent divalent acyl).

As described hereinabove, since the 2-isoxazoline derivative represented by formula [1] has two asymmetric carbons, one at the 5-position and the other at the 1'-position, the derivative has 4 types in total of stereoisomers. Similarly, since a 2,5-diamino-1,6-diphenyl-3-hydroxyhexane derivative represented by formula [6] has three asymmetric carbons, one at each of the 2-, 3-, and 5-positions, the derivative has 8 types in total of stereoisomers. Unless otherwise indicated, it must be understood that each derivative encompasses these four or eight stereoisomers and a mixture of them in an arbitrary ratio. In connection to this, if, for example, a (5S,1'S)-3-phenylmethyl-5-(1'-amino-2'-phenylethyl)-2-isoxazoline derivative represented by formula [2] is used as a starting material, either one or both of a (2S,3S,5S)-2,5-diamino-1,6-diphenyl-3-hydroxyhexane derivative and a (2S,3S,5R)-2,5-diamino-1,6-diphenyl-3-hydroxyhexane derivative represented by formulas [7] and [8], respectively, can be obtained in an arbitrary ratio, because the 5- and 1'-positions of the compound of formula [1] correspond to 3- and 2-positions of a 2,5-diamino-1,6-diphenyl-3-hydroxyhexane derivative, respectively, and their stereochemical characters are normally kept unchanged during the conversion of a 2-isoxazoline derivative of formula [1] to a compound of formula [6].

Reducing methods for the 2-isoxazoline derivatives are not particularly limited. For example, there are a method in which hydrogen or compounds serving as hydrogen sources (for example, formic acid, etc.) are used to perform catalytic hydrogenation in the presence of a metallic catalyst and a method which uses, as reducing agents, metals (for example, sodium, zinc, etc.), metal hydrides (for example, lithium aluminum hydride, sodium borohydride, sodium aluminum bis(methoxyethoxy) hydride, aluminum diisobutyl hydride, etc.). In view of selectivity of reaction, operability, safety, etc., reduction using catalytic hydrogenation and reduction using metal hydrides as reducing agents are preferred. Particularly, reduction using catalytic hydrogenation is more preferred.

2-Isoxazoline derivatives represented by formula [1] or [2] which are used for reduction are not particularly limited so long as side reactions in reducing methods to be used are practically negligible.

In catalytic hydrogenation reduction using hydrogen, it is preferred that at least one of $R^1$ and $R^2$ of formula [1] or [2] be an electron attractive group, or that $R^1$ and $R^2$ are both groups other than hydrogen. In cases where at least one of $R^1$ or $R^2$ is an electron attractive group, preferable electron attractive groups $R^1$ and $R^2$ are, for example, acyl, alkyloxycarbonyl, arylalkyloxycarbonyl, aryloxycarbonyl, alkylaminocarbonyl, arylalkylaminocarbonyl, arylaminocarbonyl, alkylsulfonyl, arylalkylsulfonyl, or arylsulfonyl, or those which link to each other to form a divalent acyl group. For convenience of selectivity of reaction and processing after reaction, preferable groups are acyl, alkyloxycarbonyl, arylalkyloxycarbonyl, aryloxycarbonyl, alkylaminocarbonyl, arylalkylaminocarbonyl, arylaminocarbonyl, and divalent acyl formed of $R^1$ and $R^2$ linked to each other. Of these, acyl, alkyloxycarbonyl, aryloxycarbonyl, and a divalent acyl formed of $R^1$ and $R^2$ linked to each other are more preferred, and alkyloxycarbonyl is particularly preferred.

If both $R^1$ and $R^2$ are the other groups than hydrogen, no particular limitation is imposed on $R^1$ and $R^2$. However, in view of readiness of post-treatment of reaction, it is preferred that $R^1$ and $R^2$ be both arylalkyl.

Specific examples of the above-mentioned acyl or divalent acyl group formed of $R^1$ and $R^2$ linked to each other are formyl, acetyl, propionyl, 2-methylpropionyl, 2,2-dimethylpropionyl, benzoyl, p-methylbenzoyl, p-methoxybenzoyl, p-nitrobenzoyl, phenylacetyl, 2-pyridylmethoxycarbonylvalyl, 3-pyridylmethoxycarbonylvalyl, 4-pyridylmethoxycarbonylvalyl, 2-pyridylmethylaminocarbonylvalyl, 6-methyl-2-pyridylmethylaminocarbonylvalyl, 2-pyridylmethylaminocarbonylisoleucyl, phthaloyl, succinyl, maleoyl, etc. For convenience of processing after reaction and in view of prices of reagents, the following groups are preferred: formyl, acetyl, propionyl, 2-methylpropionyl, 2,2-dimethylpropionyl, benzoyl, p-methylbenzoyl, p-methoxybenzoyl, p-nitrobenzoyl, phenylacetyl, phthaloyl, succinyl, and maleoyl.

Specific examples of the above-mentioned alkyloxycarbonyl group include methoxycarbonyl, ethoxycarbonyl, propoxycarbonyl, isopropoxycarbonyl, sec-butoxycarbonyl, isobutoxycarbonyl, and tert-butoxycarbonyl. For convenience of processing after reaction and in view of prices of reagents, the following groups are preferred: methoxycarbonyl, ethoxycarbonyl, isopropoxycarbonyl, isobutoxycarbonyl, and tert-butoxycarbonyl.

Specific examples of the above-mentioned aryloxycarbonyl group are phenoxycarbonyl, p-methylphenoxycarbonyl, p-methoxyphenoxycarbonyl, p-nitrophenoxycarbonyl, 1-naphthyloxycarbonyl, and 2-naphthyloxycarbonyl. For convenience of processing after reaction and in view of prices of reagents, the following groups are preferred: phenoxycarbonyl, p-methylphenoxycarbonyl, p-methoxyphenoxycarbonyl, and p-nitrophenoxycarbonyl.

When $R^1$ and $R^2$ are both arylalkyl groups, examples of such arylalkyl groups include benzyl, p-methylphenylmethyl, p-methoxyphenylmethyl, and p-nitrophenylmethyl. In view of readiness of post-treatment of reaction and costs of reagents, benzyl is preferred.

In a reduction process using metal hydrides as reducing agents, it is preferred that each of $R^1$ and $R^2$ be independently hydrogen, alkyl, arylalkyl, aryl, acyl, alkyloxycarbonyl, arylalkyloxycarbonyl, or aryloxycarbonyl since a side reaction is negligible. For convenience of selectivity of reaction and processing after reaction, hydrogen, alkyl, arylalkyl, and aryl are more preferred. Specific examples of an alkyl group include methyl, ethyl, propyl, and isopropyl. Specific examples of an arylalkyl group include benzyl, p-methylphenylmethyl, p-methoxyphenylmethyl, and p-nitrophenylmethyl. Specific examples of an aryl group include phenyl, p-methylphenyl, p-methoxyphenyl, and p-nitrophenyl.

When catalytic hydrogenation reduction is performed, homogeneous or heterogeneous metallic catalysts which are conventionally used may be used. In view of operability, heterogeneous catalysts are preferred. Metals usable as catalysts are, for example, precious metal catalysts, such as palladium, platinum, ruthenium, and rhodium, and Raney nickel. In view of selectivity of reaction and prices of catalysts, palladium and platinum catalysts are preferred. These palladium and platinum catalysts, however, are not particularly limited and may be the metal elements or the metallic compounds, or may be supported on arbitrary carriers (for example, active carbon, $Al_2O_3$, $CaCO_3$, $BaCO_3$, $BaSO_4$, $MgCO_3$, $SiO_2$, and diatomaceous earth). The amount of a catalytic metal to be supported on a carrier is not particularly limited. It is usually 0.1–50%, preferably 0.5–25%, more preferably 1–10%. Also, mixtures of different catalysts may be used.

The amount of a catalyst is not particularly limited. The weight ratio of a catalyst to a reactive substrate is usually 0.01–100%, preferably 0.1–50%, and more preferably 0.1–25%.

In catalytic hydrogenation reduction, a side reaction may occur in which an amino group formed by the reduction reacts with an imine compound, which is present as a reaction intermediate, formed by the cleavage of a N—O bond of an isoxazoline ring, and, as the result, a secondary amine and a tertiary amine are formed. Under normal reaction conditions, the reaction rate may be slow in some case, so that a large amount (for example, 50–100% of a weight ratio to substrate) of metallic catalyst is required to complete the reaction. To suppress such a side reaction and/or to increase a reaction rate (or to reduce the amount of a metallic catalyst used), it is effective to add an ammonia source, acid or a base to a reaction system singly or in the form of a mixture (including salts formed of acid and base) thereof. Ammonia sources are, for example, ammonia gas and aqueous ammonia and ammonium salts such as ammonium acetate, ammonium chloride, ammonium carbonate, ammonium hydrogencarbonate, ammonium sulfate, ammonium hydrogensulfate, monoammonium dihydrogenphosphate, diammonium monohydrogenphosphate, and triammonium phosphate. Preferably, ammonium gas, aqueous ammonia, and ammonium acetate are used. Acids to be used include inorganic acids and carboxylic acid. Inorganic acids to be used are, for example, hydrogen chloride gas, hydrochloric acid, hydrobromic acid, hydriodic acid, sulfuric acid, phosphoric acid, nitric acid, thiocyanic acid, and boric acid. Preferably, hydrogen chloride gas, boric acid are used. Carboxylic acids are, for example, formic acid, acetic acid, propionic acid, butyric acid, isobutyric acid, cinnamic acid, benzoic acid, p-methylbenzoic acid, p-methoxybenzoic acid, p-nitrobenzoic acid, phenyl acetic acid, lactic acid, oxalic acid, malonic acid, succinic acid, glutaric acid, adipic acid, maleic acid, fumaric acid, phthalic acid, terephthalic acid, citric acid, malic acid, tartaric acid, salicylic acid, nicotinic acid, mandelic acid, amino acids (such as glycine, alanine, aspartic acid, and glutamic acid). Preferably, formic acid, acetic acid, propionic acid, benzoic acid, and oxalic acid are used. Bases are, for example, ammonia, triethylamine, N-methylmorpholine, sodium methoxide, sodium ethoxide, potassium t-butoxide, sodium hydroxide, potassium hydroxide, sodium carbonate, and potassium carbonate. Preferably, ammonia, sodium methoxide, sodium ethoxide, potassium t-butoxide, sodium hydroxide, and potassium hydroxide are used.

The amount of additives to be incorporated to these reacting systems is not particularly limited, and it is usually 0.01–100 times, and preferably 0.1–50 times, by mol, that of a reactive substrate.

In catalytic hydrogenation reduction, the amount of hydrogen used is usually 0.5–100 times, preferably 1–50 times, and more preferably 1–10 times by mol as much as that of 3-phenylmethyl-5-(1'-amino-2'-phenylethyl)-2-isoxazoline derivatives represented by formula [1] or [2].

In reduction using metal hydrides as reducing agents, the amount of metal hydrides, such as lithium aluminum hydride, sodium borohydride, sodium aluminum bis (methoxyethoxy) hydride, aluminum diisobutyl hydride, is usually 0.1–10 times, preferably 0.5–5 times, and more preferably 0.8–2 times, by mol, that of 3-phenylmethyl-5-(1'-amino-2'-phenylethyl)-2-isoxazoline derivatives represented by formula [1] or [2].

Solvents used for reaction are not particularly limited as long as they do not affect the reaction in any reduction method. Examples of such solvents include water, alcohols (e.g., methanol, ethanol, propanol, isopropyl alcohol, butanol, and tert-butyl alcohol), ethers (e.g., diethyl ether, diisopropyl ether, dibutyl ether, tetrahydrofuran, dioxane, and 1,2-dimethoxyethane), nitriles (e.g., acetonitrile), esters (e.g., methyl acetate and ethyl acetate), hydrocarbons (e.g., hexane, heptane, benzene, toluene, and xylene), halogenated hydrocarbons (e.g., methylene chloride, chloroform, 1,2-dichloroethane, and chlorobenzene), ketones (e.g., acetone and methyl ethyl ketone), carboxylic acids (e.g., formic acid, acetic acid, and propionic acid), nitromethane, pyridine, dimethylsulfoxide, N,N-dimethylformamide, and N,N-dimethylacetamide. These solvents are used singly or as a mixture. The amount of a solvent is not particularly limited. The amount of a solvent used is usually 0.1–1000 times, preferably 0.1–100 times that of a reactive substrate.

In catalytic hydrogenation reduction, it is preferred that water, alcohols, ethers, esters, hydrocarbons, and carboxylic acids are used singly or in the form of a mixture thereof in order to suppress side reactions. More preferably, alcohols and carboxylic acids are used singly or in the form of a mixture thereof. As described before, an ammonium source, acid, or base may be added to the solvents.

In a reduction process using metal hydrides as reducing agents, it is preferred that ethers and hydrocarbons be used singly or in the form of a mixture thereof in order to suppress side reactions. Ethers are particularly preferred.

In any manner of reduction, reaction is performed usually at a temperature ranging from –80° C. to near a boiling point (about 200° C.) of a solvent, preferably at –50° to 120° C. more preferably at –20° to 80° C. When a reaction temperature is too low, a reaction rate tends to decrease. When a reaction temperature is too high, selectivity of reaction tends to become poor. The reaction time is not particularly limited, and it is usually 0.5–100 hours.

The reaction pressure is not particularly limited in any reduction method. It is usually 0.01–150 atm, and is preferably 1–50 atm.

In order to obtain (2S,3S,5S)-2,5-diamino-1,6-diphenyl-3-hydroxyhexane derivatives, which are important intermediates in the synthesis of medicines such as retrovirus protease inhibitors, when (5S,1'S)-3-phenylmethyl-5-(1'-amino-2'-phenylethyl)-2-isoxazoline derivatives represented by formula [2] are used as substrates for reduction, a product of reaction is usually obtained as a mixture of (2S,3S,5S)-2,5-diamino-1,6-diphenyl- 3-hydroxyhexane derivatives, (2S,3S,5R)-2,5-diamino-1,6-diphenyl-3-hydroxyhexane derivatives, other byproducts, and materials not reacted. The ratio of production between (2S,3S,5S)-2,5-diamino-1,6-diphenyl-3-hydroxyhexane derivatives and (2S,3S,5R)-2,5-diamino-1,6-diphenyl-3-hydroxyhexane derivatives depends on the structure of $R^1$ and $R^2$ of (5S,1'S)-phenylmethyl-5-(1'-amino-2'-phenylethyl)-2-isoxazoline derivatives represented by formula [2], reducing methods, and conditions of reaction. For example, when catalytic hydrogenation is performed with $R^1$ being hydrogen and $R^2$ being a tert-butoxycarbonyl group, (2S,3S,5S)-5-amino-2-tert-butoxycarbonylamino-1,6-diphenyl-3-hydroxyhexane and (2S,3S,5R)-5-amino-2-tert-butoxycarbonylamino-1,6-diphenyl-3-hydroxyhexane are produced in a ratio of about 3:1 to 20:1.

After reaction, separation from byproducts and unreacted materials and/or separation of stereoisomers can be performed by ordinary purification methods, for example, recrystallization, chromatography, and distillation. Of these, purification by recrystallization is preferable because of simple operation and easy scaleup. Of recrystallizing methods, crystallization as acid addition salts is preferred because of highly effective separation of stereoisomers and removal of byproducts. Acid addition salts for use in purification are arbitrarily selectable from salts derived from inorganic or organic acids. These acid addition salts may be adducts of organic solvents and water.

Examples of acid addition salts derived from an organic acid include hydrochlorides, hydrobromides, hydroiodides, sulfates, hydrogensulfates, phosphates, monohydrogenphosphates, dihydrogenphosphates, nitrates, and thiocyanates.

Examples of acid addition salts derived from organic acids include carboxylic acids, sulfonic acids, and phosphonic acids. Examples of acid addition salts derived from carboxylic acid include formates, acetates, propionates, butyrates, isobutyrates, cinnamates, benzoates, p-methylbenzoates, p-methoxybenzoates, p-nitrobenzoates, phenylacetates, lactates, oxalates, malonates, succinates, glutarates, adipates, maleates, fumarates, phthalates, terephthalates, citrates, malates, tartarates, salicylates, nicotinates, mandelates, and salts from amino acids (such as glycine, alanine, aspartic acid, and glutamic acid). Examples of acid addition salts derived from sulfonic acid include, for example, methanesulfonates, ethanesulfonates, benzenesulfonates, p-toluenesulfonates, p-chlorobenzenesulfonates, p-bromobenzenesulfonates, 2-naphthalenesulfonates, and camphorsulfonates. Examples of acid addition salts derived from phosphonic acid include methylphosphonates and phenylphosphonates.

The amount of acids used is usually 0.2–10 times, preferably 0.3–5 times, and more preferably 0.4–2 times by mole as much as that of 2,5-diamino-1,6-diphenyl-3-hydroxyhexane derivative represented by formula [6], [7], or [8]. Solvents for use in purification are not particularly limited so long as they do not react with 2,5-diamino-1,6-diphenyl-3-hydroxyhexane derivatives represented by formula [6], [7], or [8] and their acid addition salts. Examples of such solvents include water, alcohols (e.g., methanol, ethanol, propanol, isopropyl alcohol, butanol, and tert-butyl alcohol), ethers (e.g., diethyl ether, diisopropyl ether, dibutyl ether, tetrahydrofuran, dioxane, and 1,2-dimethoxyethane), nitriles (e.g., acetonitrile), esters (e.g., methyl acetate and ethyl acetate), hydrocarbons (e.g., hexane, heptane, benzene, toluene, and xylene), halogenated hydrocarbons (e.g., methylene chloride, chloroform, 1,2-dichloroethane, and chlorobenzene), ketones (e.g., acetone and methyl ethyl ketone), carboxylic acids (e.g., formic acid, acetic acid, and propionic acid), nitromethane, pyridine, dimethylsulfoxide, N,N-dimethylformamide, and N,N-dimethylacetamide. These solvents are used singly or as a mixture. Of these, it is preferred that water, alcohols, ethers, esters, and hydrocarbons are used singly or as a mixture of them. The amount of solvent for recrystallization is not particularly limited. It is usually 0.1–1,000 times, preferably 0.5–200 times that of a reactive substrate.

When a 2,5-diamino-1,6-diphenyl-3-hydroxyhexane derivative represented by formula [7] and/or formula [8] is produced by reducing a (5S,1'S)-3-phenylmethyl-5-(1'-amino-2'-phenylethyl)-2-isoxazoline derivative represented by formula [2], it is usually obtained in the form of a mixture of stereoisomers at the 5-position. Accordingly, in order to obtain the respective isomers at high purities, purification must involve separation of the stereoisomers. Particularly, purification of (2S,3S,5S)-2,5-diamino-1,6-diphenyl-3-hydroxyhexane derivatives, which are particularly significant intermediates in the synthesis of medicines such as retrovirus protease inhibitors and represented by formula [7], or of their acid addition salts is important (the purification includes separation and purification of a (2S,3S,5S)-2,5-diamino-1,6-diphenyl-3-hydroxyhexane derivative represented by formula [7] from a mixture of this derivative and a (2S,3S,5R)-2,5-diamino-1,6-diphenyl-3-hydroxyhexane derivative represented by formula [8]).

When purification is performed for the above purposes, a mixture is advantageously purified by recrystallizing the mixture in the form of an acid addition salt. Among recrystallization protocols, an advantageous purification method is recrystallization of acid addition salts of 2,5-diamino-1,6-diphenyl-3-hydroxyhexane derivatives represented by formulas [7] and [8] in which at least one of $R^1$ or $R^2$ is acyl, alkyloxycarbonyl, arylalkyloxycarbonyl, aryloxycarbonyl, alkylaminocarbonyl, arylalkylaminocarbonyl, arylaminocarbonyl, alkylsulfonyl, arylalkylsulfonyl, or arylsulfonyl, or $R^1$ and $R^2$ are linked to each other to form divalent acyl, and the amino group at the 2-position is protected by an electron attractive group, in view of easy removal of byproducts and unreacted products and easy separation of stereoisomers. Specifically, it is particularly preferred that carboxylic acid adducts of (2S,3S,5S)-5-amino-2-tert-butoxycarbonylamino-1,6-diphenyl-3-hydroxyhexane derivatives be selectively taken by recrystallization from a mixture of acid addition salts formed of (2S,3S,5S)-5-amino-2-tert-butoxycarbonylamino-1,6-diphenyl-3-hydroxyhexane, (2S,3S,5R)-5-amino-2-tert-butoxycarbonylamino-1,6-diphenyl-3-hydroxyhexane, and a carboxylic acid. As regards the carboxylic acid, oxalic acid is particularly preferred. By this purification method, it is possible to obtain (2S,3S,5S)-5-amino-2-tert-butoxycarbonylamino-1,6-diphenyl-3-hydroxyhexane or its acid addition salts with a high purity.

When the thus-obtained 2,5-diamino-1,6-diphenyl-3-hydroxyhexane derivative has a substituent serving as a protective group for amino at the 2-position, the derivative can be converted to 2,5-diamino-1,6-diphenyl-3-hydroxyhexane by suitably eliminating the protection of amino group. Also, if the derivative has a substituent serving as a protective group for the 2-position amino group during reduction, the newly produced free amino group at the 5-position by the reduction and another amino group at the 2-position are already discriminated, and thus, such a derivative is very useful for modifying these two amino groups differently from each other in the synthesis of medicines.

The present invention will next be described in detail by way of examples, which should not be construed as limiting the invention.

[EXAMPLE 1]

(A) Phenylacetohydroximoyl chloride

Phenylacetaldehyde oxime (45.96 g, 340 mmol) was dissolved in N,N-dimethylformamide (100 ml). N-chlorosuccinimido (45.41 g, 340 mmol) was added to the solution in 10 parts (4.54 g, 34 mmol each) at intervals of 20 minutes. During the addition, the temperature of the reaction mixture was maintained within a temperature range between 11° and 18° C. in a water bath. After completion of addition, the mixture was stirred for further 3 hours while maintaining the temperature between 15° and 17° C. Ice-water (200 ml) and toluene (200 ml) were added to the reaction mixture for extraction. The aqueous layer was further extracted with toluene (100 ml). Organic layers were combined and washed with water (250 ml) three times, then dried over anhydrous magnesium sulfate. The desiccant was filtered off, and the filtrate was used in the next step without concentration.

(B) (5S,1'S)-3-Phenylmethyl-5-(1'-amino-2'-phenylethyl)-2-isoxazoline p-toluenesulfonate (S)-3-tert-Butoxycarbonylamino-4-phenyl-1-butene (42.05 g, 170 mmol) and triethylamine (41.29 g, 408 mmol) were dissolved in toluene (62 ml). To the resulting solution phenylacetohydroximoyl chloride (prepared from 340 mmol of phenylacetaldehyde oxime) prepared in Example 1 (A) in toluene was added dropwise at room temperature over 8 hours. The mixture was stirred overnight at room temperature. Water (500 ml) was then added to the mixture, followed by extraction with toluene. The extract was condensed under reduced pressure to give an orange liquid (86.62 g), containing (5S,1'S)-3-phenylmethyl-5-(1'-tert-butoxycarbonylamino-2'-phenylethyl)-2-isoxazoline and (5R,1'S)-3-phenylmethyl-5-(1'-tert-butoxycarbonylamino-2'-phenylethyl)-2-isoxazoline. Reversed phase HPLC revealed that the ratio of (5S,1'S)-3-phenylmethyl-5-(1'-tert-butoxycarbonylamino-2'-phenylethyl)-2-isoxazoline to (5R,1'S)-3-phenylmethyl-5-(1'-tert-butoxycarbonylamino-2'-phenylethyl)-2-isoxazoline was 7:3. The liquid was dissolved in ethanol (200 ml), p-toluenesulfonic acid monohydrate (38.81 g, 204 mmol) was added. The resulting solution was refluxed with heat for 1.5 hours, to give a brown solution containing (5S,1'S)-3-phenylmethyl-5-(1'-amino-2'-phenylethyl)-2-isoxazoline p-toluenesulfonate and (5R,1'S)-3-phenylmethyl-5-(1'-amino-2'-phenylethyl)-2-isoxazoline p-toluenesulfonate. Ethyl acetate (400 ml) was added to the solution, and the mixture was cooled. Precipitated crystals were separated by filtration under reduced pressure and washed with ethanol/ethyl acetate (1/10) and ethyl acetate. The obtained wet crystals were recrystallized twice from ethanol/ethyl acetate (1/2) to give the desired compound as colorless crystals. Yield: 40.43 g (52.5%).

m.p. 206.5°–208.5° C. (decomposed).

$^1$H NMR(500 MHz, CD$_3$OD) δ ppm 7.70(d, 2H, J=8.2 Hz), 7.33–7.18(m, 12H), 4.53(dt, 1H, J=7.6 Hz), 3.66(d, 1H, J=15.0 Hz), 3.64(d, 1H, J=15.0 Hz), 3.44(broad q, 1H, J=7.3 Hz), 2.94(dd, 1H, J=17.7, 10.5 Hz), 2.90(m, 2H), 2.62(dd, 1H, J=17.7, 7.5 Hz), 2.35(s, 3H).

IR(KBr, cm$^{-1}$)3028, 2938, 1621, 1531, 1493, 1209, 1177, 1011, 704, 568.

$[α]_D^{25}$+77° (c=1.1, CH$_3$OH).

Mass spectra (FD):m/z 281(M$^+$-TsO).

Anal. Calcd. for the adduct C$_{25}$H$_{28}$N$_2$O$_4$S.0.4CH$_3$COOC$_2$H$_5$: C, 65.49;H, 6.45;N, 5.74%. Found: C, 65.66; H, 6.31;N, 5.49%.

[EXAMPLE 2]

(A) (S)-3-Phthalimido-4-phenyl-1-butene (S)-3-Amino-4-phenyl-1-butene (3.0 g, 20.4 mmol) was dissolved in tetrahydrofuran (20 ml). To the solution, an aqueous solution (10 ml) of N-carboethoxyphthalimido (4.9 g, 22.4 mmol) and anhydrous sodium carbonate (2.38 g, 22.4 mmol) were added and stirred at room temperature for 1.5 hours. The reaction mixture was concentrated under reduced pressure to remove tetrahydrofuran, followed by extraction with diisopropyl ether. The organic layer was washed successively with 1M hydrochloric acid, saturated aqueous sodium bicarbonate, and saturated brine and dried over anhydrous magnesium sulfate. After the desiccant was filtered off, the filtrate was concentrated under reduced pressure to give the desired compound as pale yellow crystals. Yield: 5.56 g.

$^1$H NMR(500 MHz, CDCl$_3$) δ ppm 7.75(m, 2H),7.65(m, 2H), 7.19–7.11(m, 5H), 6.27(ddd, 1H, J=17.2, 10.3, 7.2 Hz), 5.22(d, 1H, J=17.2 Hz), 5.19(d, 1H, J=10.3 Hz), 5.05(ddd, 1H), 3.42(dd, 1H, J=13.8, 9.9 Hz), 3.21(d, 1H, J=13.8, 6.5 Hz).

(B) Phenylacetohydroximoyl chloride

Phenylacetaldehyde oxime (33.80 g, 250 mmol) was dissolved in N,N-dimethylformamide (90 ml) and cooled in ice bath. To the solution, N-chlorosuccinimido (33.39 g, 250 mmol) was added. After completion of addition, the reaction mixture was stirred for 4 hours while gradually raising the temperature to room temperature. Ice-water (150 ml) and diisopropyl ether (200 ml) were added to the reaction mixture for extraction. The aqueous layer was further extracted with diisopropyl ether (100 ml). Organic layers were combined and washed with water three times, followed by drying over anhydrous magnesium sulfate. The desiccant was filtered off, and the filtrate was concentrated under reduced pressure to give the desired compound as a khaki solid. The solid was used in the next step without purification. Yield: 40.2 g (98%)

(C) (5S,1'S)-3-Phenylmethyl-5-(1'-amino-2'-phenylethyl)-2-isoxazoline p-toluenesulfonate (S)-3-Phthalimido-4-phenyl-1-butene (3.0 g, 10.8 mmol) prepared in Example 2 (A) was dissolved in toluene (10 ml). To the solution, an aqueous solution (20 ml) of sodium carbonate (3.15 g, 30 mmol) was added.

Phenylacetohydroximoyl chloride (4.59 g, 27.0 mmol) prepared in Example 2 (B) and dissolved in toluene (60 ml) was added dropwise at room temperature over 5 hours. After stirring at room temperature for 15 hours, water was added to the solution for separation. The organic layer was washed with water and dried over anhydrous sodium sulfate. After the desiccant was filtered off, the filtrate was concentrated under reduced pressure to give an oil containing (5S,1'S)-3-phenylmethyl-5-(1'-phthalimido-2'-phenylethyl)-2-isoxazoline and (5R,1'S)-3-phenylmethyl-5-(1'-phthalimido-2'-phenylethyl)-2-isoxazoline. Reversed phase HPLC revealed that the ratio of (5S,1'S)-3-phenylmethyl-5-(1'-phthalimido-2'-phenylethyl)-2-isoxazoline to (5R,1'S)-3-phenylmethyl-5-(1'-phthalimido-2'-phenylethyl)-2-isoxazoline was 6:4. The oil was dissolved in methanol (10 ml). An aqueous methylamine solution (40%, 15 ml) was added and stirred at 60° C. for 4 hours. The reaction mixture was concentrated under reduced pressure, and the residue was added with water and toluene for liquid separation. The separated organic layer was washed with water and dried over anhydrous sodium sulfate. After the desiccant was filtered off, the filtrate was concentrated under reduced pressure, to give an oil containing (5S,1'S)-3-phenylmethyl-5-(1'-amino-2'-phenylethyl)-2-isoxazoline and (5R,1'S)-3-phenylmethyl-5-(1'-amino-2'-phenylethyl)-2-isoxazoline. The oil was dissolved in ethanol (20 ml). p-Toluenesulfonic acid monohydrate (2.06 g, 10.8 mmol) was added to the solution and refluxed with heat to give a brown solution containing (5S,1'S)-3-phenylmethyl-5-(1'-amino-2'-phenylethyl)-2-isoxazoline p-toluenesulfonate and (5R,1'S)-3-phenylmethyl-5-(1'-amino-2'-phenylethyl)-2-isoxazoline p-toluenesulfonate. To the solution, ethyl acetate (40 ml) was added, and the mixture was cooled to precipitate crystals. The crystals were collected by filtration and washed with ethanol/ethyl acetate (1/10) and then with ethyl acetate. Crude crystals were recrystallized from ethanol (20 ml) and ethyl acetate (40 ml) to give the desired compound as colorless crystals.

Yield: 1.76 g (36%).

The obtained compound agreed with the compound obtained in Example 1 (B).

[EXAMPLE 3]

(A) (S)-3-Formylamino-4-phenyl-1-butene (S)-3-Amino-4-phenyl-1-butene (5.2 g, 35.4 mmol) was dissolved in ethyl formate (100 ml) and the solution was refluxed with heat for 6 hours. After completion of reaction, the solution was concentrated under reduced pressure to give the desired compound as an orange oil.

Yield: 6.44 g.

$^1$H NMR(500 MHz, CDCl$_3$) δ ppm 8.16(broad s, 1H), 7.33–7.16(m, 5H),5.83(ddd, 1H, J=15.8, 10.3, 5.4 Hz), 5.47 (broad s, 1H), 5.15–5.12(m, 2H), 4.88(m, 1H), 2.90(m, 2H). In addition, a rotational isomer with respect to the amide bond of N-formyl group was observed as indicated below (proportion to the former: about 3/1), δ ppm 7.84(d, 1H, J=12 Hz), 7.33–7.16(m, 5H),5.91(ddd, 1H), 5.55(broad s, 1H), 5.20–5.15(m, 2H), 4.20(m, 1H), 2.97–2.74(m, 2H).

(B) (5S,1'S)-3-phenylmethyl-5-(1'-amino-2'-phenylethyl)-2-isoxazoline p-toluenesulfonate (S)-3-formylamino-4-phenyl-1-butene (3.0 g, 17.1 mmol) prepared in Example 3 (A) was dissolved in toluene (10 ml). To the solution, triethylamine (3.46 g, 34.2 mmol) was added. A toluene solution (60 ml) of phenylacetohydroximoyl chloride prepared in a manner similar to that described in Example 1 (A) from phenylacetaldehyde oxime (4.63 g, 34.2 mmol) was added dropwise at room temperature over 4 hours. After stirring the mixture at room temperature for 15 hours, water was added for liquid separation. The separated organic layer was washed with water and dried over anhydrous sodium sulfate. After the desiccant was filtered off, the filtrate was concentrated under reduced pressure to give an oil containing (5S, 1'S)-3-phenylmethyl-5-(1'-formylamino-2'-phenylethyl)-2-isoxazoline and (5R,1'S)-3-phenylmethyl-5-(1'-formylamino-2'-phenylethyl)-2-isoxazoline. Reversed phase HPLC revealed that the ratio of (5S,1'S)-3-phenylmethyl-5-(1'-formylamino-2'-phenylethyl)-2-isoxazoline to (5R,1'S)-3-phenylmethyl-5-(1'-formylamino-2'-phenylethyl)-2-isoxazoline was 6:4. The oil was dissolved in ethanol (25 ml). p-Toluenesulfonic acid monohydrate (4.48 g, 23.5 mmol) was added to the solution and refluxed with heat for 4 hours to give a brown solution containing (5S,1'S)-3-phenylmethyl-5-(1'-amino-2'-phenylethyl)-2-isoxazoline p-toluenesulfonate and (5R,1'S)-3-phenylmethyl-5-(1'-amino-2'-phenylethyl)-2-isoxazoline p-toluenesulfonate. Ethyl acetate (50 ml) was added to the solution and the mixture was cooled to precipitate crystals. The crystals were collected by filtration and washed with ethanol/ethyl acetate (1/10) and then with ethyl acetate. Crude crystals were recrystallized from ethanol (25 ml) and ethyl acetate (50 ml) to give the desired compound as colorless crystals.

Yield: 2.34 g (30%).

The obtained compound agreed with the compound obtained in Example 1 (B).

[EXAMPLE 4]

(A) (S)-3-N,N-Dibenzylamino-4-phenyl-1-butene and (S)-3-N,N-dibenzylamino-4-phenyl-1-butene hydrochloride Potassium carbonate (95.3 g, 690 mmol), water (143 g), and benzyl chloride (81.1 g, 641 mmol) were added to (S)-3-amino-4-phenyl-1-butene (34.3 g, 233 mmol). The mixture was stirred at 80° C. for 48 hours. Toluene (622 g) and water (143 g) were added to the reaction mixture, and the separated organic layer was washed with water (143 g). Reversed phase HPLC revealed that the toluene solution contained 52.2 g (160 mmol, yield 69%) of the desired compound. The solution was concentrated under reduced pressure to give the desired compound as a yellow oil.

$^1$H NMR(500 MHz,CDCl$_3$) δ ppm 7.23(m, 13H),7.04(m, 2H), 5.87(ddd, 1H, J=17.3, 10.3, 8.0 Hz), 5.24(d, 1H, J=10.3 Hz), 5.02(d, 1H, J=17.2 Hz), 3.82(d, 2H, J=13.9 Hz), 3.45(d, 2H, J=14.0 Hz), 3.38(q, 1H, J=7.7 Hz), 3.02(dd, 1H, J=13.8, 7.7 Hz), 2.78(dd, 1H, J=13.8, 7.5 Hz).

IR(neat,cm$^{-1}$)3161, 3025, 2800, 1494, 1454, 1119, 1073, 1028, 978, 923, 742, 697.

An oil (16.37 g) containing (S)-3-N,N-dibenzylamino-4-phenyl-1-butene obtained in a manner similar to that described above was dissolved in a solvent mixture of isopropyl alcohol (20 ml) and diisopropyl ether (50 ml), and was further combined with conc. hydrochloric acid (7.60 g). The resulting mixture was heated to 70° C. while stirring, and then cooled to room temperature, followed by cooling to 0° C. with ice. A colorless solid precipitated was collected by filtration and washed with a mixture of isopropyl alcohol (10 ml) and diisopropyl ether (25 ml) and then washed twice with diisopropyl ether (20 ml). The obtained wet crystals were dried under reduced pressure at room temperature to give colorless crystals.

Yield: 11.62 g.

m.p. 139.1°–141.1° C.

$^1$H NMR(500 MHz, CDCl$_3$) δ ppm 7.80(m, 4H), 7.40(m, 6H), 7.19(m, 3H), 7.12(m, 2H), 5.98(dt, 1H, J=17.0, 9.8 Hz), 5.51 (d, 1H, J=10.4 Hz), 4.99(d, 1H, J=17.2 Hz), 4.64(dd, 1H, J=13.3, 4.6 Hz), 4.19(m, 2H), 4.06(m, 2H), 3.98(broad t, 1H, J=10.3 Hz), 2.83(t, 1H, J=12.0 Hz).

IR(KBr, cm$^{-1}$)3466, 2488, 1459, 935, 749, 738, 699, 498.

(B) Phenylacetohydroximoyl chloride

Phenylacetaldehyde oxime (40.5 g, 300 mmol) was dissolved in acetonitrile (100 ml). To the solution, a 6.7% aqueous hydrochloric acid (145 g) and then an 8.5% aqueous sodium hypochlorite (262 g, 299 mmol) were added dropwise at −10° C. over 2.3 hours. The mixture was stirred at −5° C. for 30 minutes and then combined with toluene (200 ml) for extraction. The separated organic layer was washed twice with water (200 ml). Reversed phase HPLC revealed that the extract contained 40.3 g (238 mmol, yield 79%) of the desired compound. The solution was used in the next step without concentration.

(C) (5S,1'S)-3-Phenylmethyl-5-(1'-N,N-dibenzylamino-2'-phenylethyl)-2-isoxazoline A 10% aqueous sodium carbonate (124 g, 117 mmol) was added to an oil (34.3 g) containing (S)-3-N,N-dibenzylamino-4-phenyl-1-butene (21.88 g, 66.9 mmol) prepared in Example 4 (A). A toluene solution (159.7 g) containing phenylacetohydroximoyl chloride (24.95 g, 147 mmol) prepared in Example 4 (B) was added to the mixture dropwise at room temperature over 7.5 hours. After stirring the mixture at room temperature for 14.5 hours, water was added, separated, followed by washing the organic layer with water. The organic layer was concentrated under reduced pressure to give an oil (61.4 g) containing (5S,1'S)-3-phenylmethyl-5-(1'-N,N-dibenzylamino-2'-phenylethyl)-2-isoxazoline and (5R,1'S)-3-phenylmethyl-5-(1'-N,N-dibenzylamino-2'-phenylethyl)-2-isoxazoline. The oil (60.3 g) was dissolved in isopropyl alcohol (92.4 g) and combined with conc. hydrochloric acid (8.0 g) and water (30.8 g). The resulting mixture was stirred at room temperature for 1 hour and further while cooling with ice for 1 hour. The precipitated crystals were collected by filtration under reduced pressure and washed with isopropyl alcohol (23.1 9). The crystals were dried under reduced pressure to give the desired compound as colorless crystals. Yield: 3.39 g (25%).

The obtained compound agreed with the compound obtained in Example 21.

[EXAMPLE 5]

(5RS,1'RS)-3-Phenylmethyl-5-(1'-amino-2'-phenylethyl)-2-isoxazoline p-toluenesulfonate (RS)-3-tert-Butoxycarbonylamino-4-phenyl-1-butene (6.4 g, 25.9 mmol) was dissolved in toluene (10 ml), and was added triethylamine (5.50 g, 54.3 mmol). To the solution, a toluene solution (100 ml) of phenylacetohydroximoyl chloride prepared in a manner similar to that described in Example 1 (A) was added dropwise to the mixture at room temperature over 6 hours. After stirring at room temperature for 15 hours, water was added to the solution for liquid separation. The organic layer was washed and dried over anhydrous sodium sulfate. After the desiccant was filtered off, the filtrate was concentrated under reduced pressure to give an oil containing (5RS,1'RS)-3-phenylmethyl-5-(1'-tert-butoxycarbonylamino-2'-phenylethyl)-2-isoxazoline and (5RS,1'SR)-3-phenylmethyl-5-(1'-tert-butoxycarbonylamino- 2'-phenylethyl)-2-isoxazoline. Reversed phase HPLC revealed that the ratio of (5RS,1'RS)-3-phenylmethyl-5-(1'-tert-butoxycarbonylamino-2'-phenylethyl)-2-isoxazoline to (5RS,1'SR)-3-phenylmethyl-5-(1'-tert-butoxycarbonylamino-2'-phenylethyl)-2-isoxazoline was 7:3. The oil was dissolved in ethanol (55 ml), and p-toluenesulfonic acid monohydrate (5.5 g, 28.9 mmol) was added and the solution was refluxed with heat for 2 hours. The reaction mixture was concentrated under reduced pressure, dissolved in ethanol (30 ml) again, and then refluxed with heat to give a brown solution containing (5RS,1'RS)-3-phenylmethyl-5-(1'-amino-2'-phenylethyl)-2-isoxazoline p-toluenesulfonate and (5RS,1'SR)-3-phenylmethyl-5-(1'-amino-2'-phenylethyl)-2-isoxazoline p-toluenesulfonate. Ethyl acetate (150 ml) was added, and the mixture was cooled to precipitate crystals. The precipitated crystals were collected by filtration and washed with ethanol/ethyl acetate (1/10) and further with ethyl acetate. Crude crystals were recrystallized from ethanol (30 ml) and ethyl acetate (120 ml) to give the desired compound as colorless crystals. Yield: 4.13 g (35%).

m.p. 198.5°–200.7° C. (decomposed).

$^1$H NMR(500 MHz,$CD_3OD$) δ ppm 7.70(d, 2H, J=8.2 Hz), 7.33–7.18(m, 12H), 4.53(dt, 1H, J=7.6 Hz), 3.66(d, 1H, J=15.0 Hz), 3.64(d, 1H, J=15.0 Hz), 3.44(broad q, J=7.3 Hz), 2.94(dd, 1H, J=17.7, 10.5 Hz), 2.90(m, 2H), 2.62(dd, 1H, J=17.7, 7.5 Hz), 2.35(s, 3H).

IR(KBr, cm$^{-1}$)3028, 2940, 1620, 1531, 1494, 1209, 1177, 1034, 1011, 704, 682, 569.

Anal. Calcd. for the adduct $C_{25}H_{28}N_2O_4S.0.3CH_3COOC_2H_5$: C, 65.70;H,6.40;N, 5.85%. Found: C, 65.77;H, 6.37;N, 5.64%.

[EXAMPLE 6]

(5S,1'S)-3-Phenylmethyl-5-(1'-tert-butoxycarbonylamino-2'-phenylethyl)-2-isoxazoline Water (155 ml), toluene (100 ml), and anhydrous sodium carbonate (13.68 g, 129 mmol) were added to (5S,1'S)-3-phenylmethyl-5-(1'-amino-2'-phenylethyl)-2-isoxazoline p-toluenesulfonate (38.92 g, 86.0 mmol) prepared in Example 1 (B) and the mixture was stirred at room temperature. Di-tert-butyldicarbonate (19.72 g, 90.4 mmol) in toluene (50 ml) was added dropwise at room temperature over 20 minutes. The mixture was further stirred overnight at room temperature and then extracted with toluene, and the aqueous layer was extracted with toluene (100 ml). The toluene layers were combined together and washed with saturated aqueous sodium bicarbonate, followed by concentration under reduced pressure to give 32.8 g of residue. The residue (30.79 g) was recrystallized from hexane (200 ml) to give the desired compound as colorless crystals. Yield: 28.35 g (87%).

m.p. 94.0°–95.0° C.

$^1$H NMR(500 MHz, $CDCl_3$) δ ppm 7.31–7.18(m, 10H), 4.70(d, 1H, J=10.0 Hz), 4.49(broad t, 1H), 3.86(broad q, 1H), 3.64(d, 1H, J=14.7 Hz), 3.62(d, 1H, J=14.7 Hz), 2.91 (dd, 1H, J=13.4, 6.8 Hz), 2.86(dd, 1H, J=13.4, 9.0 Hz), 2.76(dd, 1H, J=17.5, 11.0 Hz), 2.67(dd, 1H, J=17.5, 8.6 Hz), 1.36(s, 9H).

IR(KBr, cm$^{-1}$)3389, 1698, 1504, 1245, 1170, 858, 700.

$[α]_D^{25}$+89° (c=1.2, $CH_3OH$). Mass spectrum (FD):m/z 380($M^+$).

Anal. Calcd. for $C_{23}H_{28}N_2O_3$: C, 72.61;H, 7.42;N, 7.36%. Found: C, 72.68;H, 7.42;N, 7.34%.

[EXAMPLE 7]

(5RS,1'RS)-3-Phenylmethyl-5-(1'-tert-butoxycarbonylamino-2'-phenylethyl)-2-isoxazoline (5RS,1'RS)-3-Phenylmethyl-5-(1'-amino-2'-phenylethyl)-2-isoxazoline p-toluenesulfonate (250 mg, 0.55 mmol) prepared in Example 5 were suspended in tetrahydrofuran (10 ml) and cooled with ice. To the resulting suspension, triethylamine (56 mg, 0.55 mmol) was added. Di-tert-butyldicarbonate (120 mg, 0.55 mmol) was added and the mixture was stirred at room temperature for 4 hours. The reaction mixture was concentrated under reduced pressure. To the residue, water and ethyl acetate were added for liquid separation. The organic layer was washed with saturated aqueous sodium bicarbonate and then with water, followed by drying over anhydrous magnesium sulfate. After the desiccant was filtered off, the filtrate was concentrated to give an oil, to which hexane was added for crystallization. Crude crystals were recrystallized from diisopropyl ether/hexane to give the desired compound as colorless crystals. Yield: 148 mg (71%)

m.p. 106.0°–107.3° C.

$^1$H NMR(500 MHz, $CDCl_3$) δ ppm 7.31–7.18(m, 10H), 4.70(d, 1H, J=10.0 Hz), 4.49(broad t, 1H), 3.86(broad q, 1H), 3.64(d, 1H, J=14.7 Hz), 3.62(d, 1H, J=14.7 Hz), 2.91 (dd, 1H, J=13.4, 6.8 Hz), 2.86(dd, 1H, J=13.4, 9.0 Hz), 2.76(dd, 1H, J=17.5, 11.0 Hz), 2.67(dd, 1H, J=17.5, 8.6 Hz), 1.36(s, 9H).

IR(KBr, cm$^{-1}$)3394, 1687, 1510, 1494, 1248, 1163, 861, 700

[EXAMPLE 8]

(5S,1'S)-3-Phenylmethyl-5-(1'-phthalimido-2'-phenylethyl)-2-isoxazoline (S)-3-Phthalimido-4-phenyl-1-butene (700 mg, 2.52 mmol) prepared in a manner similar to that described in Example 2 (A) and phenylacetohydroximoyl chloride (816 mg, 5.04 mmol) were dissolved in toluene (10 ml). To the resulting solution, anhydrous calcium carbonate (1.0 g, 10.0 mmol) and water (10 ml) were added and the mixture was stirred at room temperature. In the course of stirring, phenylacetohydroximoyl chloride (400 mg) in toluene (10 ml) were further added dropwise. After completion of reaction, the reaction mixture was filtered using Celite. The filtrate was washed with water and dried over anhydrous magnesium sulfate. After the desiccant was filtered off, the filtrate was concentrated under reduced pressure to obtain an oil (1.9 g) containing (5S,1'S)-3-phenylmethyl-5-(1'-phthalimido-2'-phenylethyl)-2-isoxazoline and (5R,1'S)-3-phenylmethyl-5-(1'-phthalimido-2'-phenylethyl)-2-isoxazoline. Reversed phase HPLC revealed that the ratio of (5S,1'S)-3-phenylmethyl-5-(1'-phthalimido-2'-phenylethyl)-2-isoxazoline to (5R,1'S)-3-phenylmethyl-5-(1'-phthalimido-2'-phenylethyl)-2-isoxazoline was 6:4. A half portion of the oil (1.9 g) was purified by silica gel column chromatography (solvent for elution, hexane:ethyl acetate=4:1) to give the desired compound as colorless crystals. Yield: 270 mg. The crude crystals were recrystallized from diisopropyl ether. Yield: 180 mg.

m.p. 114.0°–115.5° C.

$^1$H NMR(500 MHz, CDCl$_3$) δ ppm 7.74(m, 2H), 7.65(m, 2H), 7.36–7.04(m, 10H), 5.15(dt, 1H), 4.47(ddd, 1H, J=9.0 Hz), 3.71(d, 1H, J=14.8 Hz), 3.68(d, 1H, J=14.8 Hz), 3.34(dd, 1H, J=14.0, 11.2 Hz), 2.97(dd, 1H, J=17.2, 10.3 Hz), 2.91(dd, 1H, J=14.0, 4.8 Hz), 2.70(dd, 1H, J=17.2, 7.4 Hz).

IR(KBr, cm$^{-1}$)1708, 1388, 720, 707.

[α]$_D^{25}$+100° (c=1.3,CHCl$_3$).

Mass spectrum (FD):m/z 410(M$^+$).

Anal. Calcd. for C$_{26}$H$_{22}$N$_2$O$_3$: C,76.08;H, 5.40;N, 6.82%. Found: C,75.98;H, 5.33;N, 6.75%.

[EXAMPLE 9]

(A) (RS)-3-Phthalimido-4-phenyl-1-butene (RS)-3-Amino-4-phenyl-1-butene (1.2 g, 8.0 mmol) was dissolved in tetrahydrofuran (20 ml). To the solution, a solution of N-carbethoxyphthalimido (2.2 g, 10.0 mmol) in water (20 ml) and anhydrous sodium carbonate (1.06 g, 10.0 mmol) was added and stirred at room temperature for 1 hour. The reaction mixture was concentrated under reduced pressure to remove tetrahydrofuran, followed by extraction with ethyl acetate.

The organic layer was washed successively with 1M hydrochloric acid, saturated aqueous sodium bicarbonate, and saturated brine, and dried over anhydrous sodium sulfate. After the desiccant was filtered off, the filtrate was concentrated under reduced pressure. The obtained pale yellow crystals were separated and purified by silica gel column chromatography (solvent for elution, hexane:ethyl acetate=9:1) to give the desired compound as colorless crystals. Yield: 2.1 g (93%).

$^1$H NMR(500 MHz, CDCl$_3$) δ ppm 7.75(m, 2H), 7.65(m, 2H), 7.19–7.11 (m, 5H), 6.27(ddd, 1H, J=17.2, 10.3, 7.2 Hz), 5.22(d, 1H, J=17.2 Hz), 5.19(d, 1H, J=10.3 Hz), 5.05(ddd, 1H), 3.42(dd, 1H, J=13.8, 9.9 Hz), 3.21(d, 1H, J=13.8, 6.5 Hz).

(B) (5RS,1'RS)-3-Phenylmethyl-5-(1'-phthalimido-2'-phenylethyl)-2-isoxazoline (RS)-3-Phthalimido-4-phenyl-1-butene (558 mg, 2.01 mmol) obtained in Example 9 (A) and phenylacetohydroximoyl chloride (512 mg, 3.02 mmol) prepared in a manner similar to that described in Example 2 (B) were dissolved in diethyl ether (10 ml). To the solution, triethylamine (336 mg, 3.32 mmol) in diethyl ether (10 ml) was added dropwise at room temperature over 3 hours. The mixture was stirred at room temperature for 1 hour, and then water and diethyl ether were added for liquid separation. The separated organic layer was washed with saturated brine and dried over anhydrous sodium sulfate. After the desiccant was filtered off, the filtrate was concentrated under reduced pressure to give an oil (0.91 g) containing (5RS,1'RS)-3-phenylmethyl-5-(1'-phthalimido-2'-phenylethyl)-2-isoxazoline and (5RS,1'SR)-3-phenylmethyl-5-(1'-phthalimido-2'-phenylethyl)-2-isoxazoline. Reversed phase HPLC revealed that the ratio of (5RS,1'RS)-3-phenylmethyl-5-(1'-phthalimido-2'-phenylethyl)-2-isoxazoline to (5RS,1'SR)-3-phenylmethyl-5-(1'-phthalimido-2'-phenylethyl)-2-isoxazoline was 6:4. The oil (0.91 g) was separated by silica gel column chromatography (solvent for elution, hexane:ethyl acetate=4:1) to give the desired compound as colorless crystals. Yield: 340 mg (41%). For analysis, part of the compound was recrystallized from diisopropyl ether/hexane.

m.p. 134.0°–135.5° C.

$^1$H NMR(500 MHz, CDCl$_3$) δ ppm 7.74(m, 2H), 7.65(m, 2H), 7.36–7.04(m, 10 H), 5.15(dt, 1H), 4.47(ddd, 1H, J=9.0 Hz), 3.71 (d, 1H, J=14.8 Hz), 3.68(d, 1H, J=14.8 Hz), 3.34(dd, 1H, J=14.0, 11.2 Hz), 2.97(dd, 1H, J=117.2, 10.3 Hz), 2.91(dd, 1H, J=14.0, 4.8 Hz), 2.70(dd, 1H, J=17.2, 7.4 Hz).

IR(KBr, cm$^{-1}$ )1770, 1710, 1381, 726, 703.

[EXAMPLE 10]

(5S,1'S)-3-Phenylmethyl-5-(1'-benzyloxycarbonylamino-2'-phenylethyl)-2-isoxazoline (5S,1'S)-3-Phenylmethyl-5-(1'-amino-2'-phenylethyl)-2-isoxazoline p-toluenesulfonate (300 mg, 0.66 mmol) prepared in a manner similar to that described in Example 1 (B) was suspended in tetrahydrofuran and cooled with ice. To the suspension, triethylamine (142 mg, 1.4 mmol) and benzyl chloroformate (124 mg, 0.73 mmol) were added, then the mixture was stirred for 2 hours. The reaction mixture was concentrated under reduced pressure. To the residue, water and ethyl acetate were added for liquid separation. The organic layer was washed with saturated aqueous sodium bicarbonate and then with water, followed by drying over anhydrous magnesium sulfate. After the desiccant was filtered off, the filtrate was concentrated to give an oil. The oil was crystallized from diisopropyl ether/hexane to give the desired compound as colorless crystals. Yield: 145 mg (53%).

m.p. 80.5°–82.0° C.

$^1$H NMR(500 MHz, CDCl$_3$) δ ppm 7.37–7.14(m, 15H), 5.03(d, 1H, J=12.4 Hz), 4.97(d, 1H, J=12.4 Hz), 4.95(d, 1H, J=9.9 Hz), 4.51(broad t, 1H), 3.93(broad q, 1H), 3.59(d, 1H, J=14.9 Hz), 3.51(d, 1H, J=14.9 Hz), 2.93(dd, 1H, J=13.6, 7.1 Hz), 2.88(dd, 1H, J=13.6, 8.9 Hz), 2.77(dd, 1H, J=17.8, 11.5 Hz), 2.65(dd, 1H, J=17.8, 8.1 Hz).

IR(KBr, cm$^{-1}$)3370, 1702, 1521, 1494, 1453, 1252, 1237, 1046, 750, 700.

[α]$_D^{25}$+84° (c=1.1, CH$_3$OH). Mass spectrum (FD):m/z 414(M$^+$).

Anal. Calcd. for C$_{26}$H$_{26}$N$_2$O$_3$: C, 75.34;H, 6.32;N, 6.76%. Found: C, 75.47;H, 6.42;N, 6.90%.

[EXAMPLE 11]

(5RS,1'RS)-3-Phenylmethyl-5-(1'-benzyloxycarbonyl amino-2'-phenylethyl)-2-isoxazoline (5RS,1'RS)-3-Phenylmethyl-5-(1'-amino-2'-phenylethyl)-2-isoxazoline p-toluenesulfonate (250 mg, 0.55 mmol) prepared in Example 5 was suspended in tetrahydrofuran (10 ml) and cooled with ice. To the suspension, triethylamine (111 mg, 1.10 mmol) and chloroformate (94 mg, 0.55 mmol) were added and stirred at room temperature for 4 hours. The reaction mixture was concentrated under reduced pressure. To the residue, water and ethyl acetate were added for liquid separation. The organic layer was washed with saturated aqueous sodium bicarbonate and then with water, and dried over anhydrous magnesium sulfate. After the desiccant was filtered off, the filtrate was concentrated to give an oil. Hexane was added to the oil for crystallization. Crude crystals were recrystallized from diisopropyl ether/hexane to give the desired compound as colorless crystals. Yield: 167 mg (61%).

m.p. 87.5°–89.5° C.

$^1$H NMR(500 MHz, CDCl$_3$) δ ppm 7.37–7.14(m, 15H), 5.03(d, 1H, J=12.4 Hz), 4.97(d, 1H, J=12.4 Hz), 4.95(d, 1H, J=9.9 Hz), 4.51(broad t, 1H), 3.93(broad q, 1H), 3.59(d, 1H, J=14.9 Hz), 3.51(d, 1H, J=14.9 Hz), 2.93(dd, 1H, J=13.6, 7.1 Hz), 2.88(dd, 1H, J=13.6, 8.9 Hz), 2.77(dd, 1H, J=17.8, 11.5 Hz), 2.65(dd, 1H, J=17.8, 8.1 Hz).

IR(KBr, cm$^{-1}$)3250, 1702, 1547, 1495, 1453, 1256, 730, 699.

[EXAMPLE 12]

(5RS,1'RS)-3-Phenylmethyl-5-(1'-benzyloxycarbonylamino-2'-phenylethyl)-2-isoxazoline Toluene (12 ml) solution phenylacetohydroximoyl chloride (0.264 g, 1.56 mmol) obtained in a manner similar to that described in Example 2 (B) was added dropwise to the toluene (4 ml) solution of (RS)-3-benzyloxycarbonylamino-4-phenyl-1-butene (0.288 g, 1.0 mmol) and triethylamine (0.190 g, 1.88 mmol) over 1.25 hours while cooling in an ice-water bath. After stirring for 1.65 hours in an ice-water bath and for 2 hours at room temperature, water was added, followed by extraction with diisopropyl ether. The organic layer was dried over anhydrous magnesium sulfate, and then After the desiccant was filtered off, the filtrate was concentrated under reduced pressure to give yellow liquid (0.53 g). The liquid was purified by silica gel column chromatography (solvent for elution, ethyl acetate/hexane=1/7 to 1/4) to give the desired compound (0.22 g, 52%) as yellow liquid. Part of the yellow liquid was recrystallized from diisopropyl ether/hexane to give the desired compound as colorless crystals.

The thus obtained compound agreed with the compound obtained in Example 11.

[EXAMPLE 13]

(5S,1'S)-3-Phenylmethyl-5-(1'-methoxycarbonylamino-2'-phenylethyl)-2-isoxazoline (5S,1'S)-3-Phenylmethyl-5-(1'-amino-2'-phenylethyl)-2-isoxazoline p-toluenesulfonate (300 mg, 0.66 mmol) prepared in a manner similar to that described in Example 1 (B) was suspended in tetrahydrofuran (5 ml) and cooled with ice, and triethylamine (142 mg, 1.4 mmol) was added. To the mixture, methyl chloroformate (70 mg, 0.73 mmol) was added and the mixture was stirred for 2 hours. The reaction mixture was concentrated under reduced pressure. To the residue, water and ethyl acetate were added for separation. The organic layer was washed with saturated aqueous sodium bicarbonate and then with water, followed by drying over anhydrous magnesium sulfate. After the desiccant was filtered off, the filtrate was concentrated to give an oil. The oil was crystallized from diisopropyl ether/hexane to give the desired compound as colorless crystals. Yield: 146 mg (65%).

m.p. 90.5°–93.0° C.

$^1$H NMR(500 MHz, CDCl$_3$) δ ppm 7.30–7.17(m, 10H), 4.83(d, 1H, J=10.0 Hz), 4.51(m, 1H), 3.89(broad q, 1H), 3.64(d, 1H, J=14.6 Hz), 3.61(d, 1H, J=14.6 Hz), 3.57(s, 3H), 2.91(dd, 1H, J=13.5, 6.7 Hz), 2.87(dd, 1H, J=13.5, 9.1 Hz), 2.78(dd, 1H, J=17.4, 11.0 Hz), 2.65(dd, 1H, J=17.4, 8.0 Hz).

IR(KBr, cm$^{-1}$)3382, 1702, 1522, 1245, 1059, 727, 701.

$[α]_D^{25}$+89° (c=1.0, CH$_3$OH). Mass spectrum (FD):m/z 338(M$^+$).

Anal. Calcd. for C$_{20}$H$_{22}$N$_2$O$_3$: C, 70.99;H, 6.55;N, 8.28%. Found: C, 71.16;H, 6.56;N, 8.19%.

[EXAMPLE 14]

(5RS,1'RS)-3-Phenylmethyl-5-(1'-methoxycarbonylamino-2'-phenylethyl)-2-isoxazoline (5RS,1'RS)-3-Phenylmethyl-5-(1'-amino-2'-phenylethyl)-2-isoxazoline p-toluenesulfonate (250 mg, 0.55 mmol) prepared in Example 5 was suspended in tetrahydrofuran (5 ml) and cooled with ice. To the suspension, triethylamine (122 mg, 1.21 mmol) and methyl chloroformate (62 mg, 0.66 mmol) were added and the mixture was stirred at room temperature for 3 hours. The reaction mixture was concentrated under reduced pressure. To the residue, water and ethyl acetate were added for liquid separation. The separated organic layer was washed with saturated aqueous sodium bicarbonate and then with water, followed by drying over anhydrous magnesium sulfate. After the desiccant was filtered off, the filtrate was concentrated to obtain an oil. The oil was crystallized from diisopropyl ether/hexane to give the desired compound as colorless crystals. Yield: 136 mg (73%).

m.p. 87.0° to 88.5° C.

$^1$H NMR(500 MHz, CDCl$_3$) δ ppm 7.30–7.17(m, 10H), 4.83(d, 1H, J=10.0 Hz), 4.51(m, 1H), 3.89(broad q, 1H), 3.64(d, 1H, J=14.6 Hz), 3.61(d, 1H, J=14.6 Hz), 3.57(s, 3H), 2.91(dd, 1H, J=13.5, 6.7 Hz), 2.87(dd, 1H, J=13.5, 9.1 Hz), 2.78(dd, 1H, J=17.4, 11.0 Hz), 2.65(dd, 1H, J=17.4, 8.0 Hz).

IR(KBr, cm$^{-1}$) 3277, 1707, 1702, 1534, 1252, 1047, 704.

[EXAMPLE 15]

(5S,1'S)-3-Phenylmethyl-5-(1'-formylamino-2'-phenylethyl)-2-isoxazoline (5S,1'S)-3-Phenylmethyl-5-(1'-amino-2'-phenylethyl)-2-isoxazoline p-toluenesulfonate (300 mg, 0.66 mmol) prepared in a manner similar to that described in Example 1 (B) was suspended in tetrahydrofuran (5 ml) and cooled with ice. To the suspension, triethylamine (67 mg, 0.66 mmol) and formic acid (37 mg, 0.8 mmol) were added, and then 1-ethyl-3-(3-dimethylaminopropyl) carbodiimide hydrochloride (127 mg, 0.66 mmol) was added. The resulting mixture was stirred for 2 hours on ice and then for 1 hour at room temperature, then concentrated under reduced pressure. A 10% aqueous citric acid and ethyl acetate were added to the residue for liquid separation. The organic layer separated was washed with saturated aqueous sodium bicarbonate and then with water, followed by drying over anhydrous magnesium sulfate. After the desiccant was filtered off, the filtrate was concentrated to give an oil. To the oil, hexane was added and crystals were obtained. Crude crystals were recrystallized from ethyl acetate/hexane to give the desired compound as colorless crystals. Yield: 146 mg (72%).

m.p. 94.5°–95.8° C.

$^1$H NMR(500 MHz, CDCl$_3$) δ ppm 7.93(s, 1H), 7.32–7.14 (m, 10H), 5.64(d, 1H, J=9.6 Hz), 4.54(dd, 1H), 4.34(broad q, 1H), 3.61(s, 2H), 2.91(d, 2H, J=8.0 Hz), 2.85(dd, 1H, J=17.5, 11.1 Hz), 2.63(dd, 1H, J=17.5, 7.6 Hz).

IR(KBr, cm$^{-1}$)3345, 1651, 1514, 1386, 1234, 718, 699.

$[\alpha]_D^{25}$+79° (c=1.1,CH$_3$OH). Mass spectrum (FD):m/z 308(M$^+$).

Anal. Calcd. for C$_{19}$H$_{20}$N$_2$O$_2$: C, 74.00;H, 6.54;N, 9.08%. Found: C, 73.80;H, 6.54;N, 8.91%.

[EXAMPLE 16]

(5RS,1'RS)-3-Phenylmethyl-5-(1'-formylamino-2'-phenylethyl)-2-isoxazoline (5RS,1'RS)-3-Phenylmethyl-5-(1'-amino-2'-phenylethyl)-2-isoxazoline p-toluenesulfonate (250 mg, 0.55 mmol) prepared in Example 5 was suspended in tetrahydrofuran (5 ml) and cooled with ice. To the suspension, triethylamine (56 mg, 0.55 mmol) and formic acid (30 mg, 0.65 mmol) were added, then 1-ethyl-3-(3-dimethylaminopropyl) carbodiimide hydrochloride (127 mg, 0.66 mmol) was added. The mixture was stirred at room temperature for 2 hours. The reaction mixture was concentrated under reduced pressure. To the residue, water and ethyl acetate were added for liquid separation. The organic layer separated was washed successively with a 10% aqueous citric acid, saturated aqueous sodium bicarbonate, and water, followed by drying over anhydrous magnesium sulfate. After the desiccant was filtered off, the filtrate was concentrated to give an oil. To the oil, hexane was added and crystals were obtained. Crude crystals were recrystallized from ethyl acetate/diisopropyl ether to give the desired compound as colorless crystals.

Yield: 115 mg (68%).

m.p. 112.0° to 113.0° C.

$^1$H NMR(500 MHz, CDCl$_3$) δ ppm 7.93(s, 1H), 7.32–7.14 (m, 10H), 5.64(d, 1H, J=9.6 Hz),4.54(dd, 1H),4.34(broad q, 1H), 3.61(s, 2H), 2.91(d, 2H, J=8.0 Hz), 2.85(dd, 1H, J=17.5, 11.1 Hz), 2.63(dd, 1H, J=17.5, 7.6 Hz).

IR(KBr, cm$^{-1}$)3209, 3027, 1658, 1545, 1385, 894, 702.

[EXAMPLE 17]

(5S,1'S)-3-Phenylmethyl-5-(1'-acetylamino-2'-phenylethyl)-2-isoxazoline (5S,1'S)-3-Phenylmethyl-5-(1'-amino-2'-phenylethyl)-2-isoxazoline p-toluenesulfonate (300 mg, 0.66 mmol) prepared in a manner similar to that described in Example 1 (B) was suspended in ethanol (5 ml). To the suspension, anhydrous sodium acetate (65 mg, 0.8 mmol) and acetic anhydride (65 mg, 0.8 mmol) were added. The mixture was stirred at room temperature for 15 minutes, then concentrated under reduced pressure. Water and ethyl acetate were added to the residue for liquid separation. The organic layer separated was washed with saturated aqueous sodium bicarbonate and then with water, followed by drying over anhydrous magnesium sulfate. After the desiccant was filtered off, the filtrate was concentrated to give crude crystals. The crude crystals were recrystallized from hexane/ethyl acetate to give the desired compound as colorless crystals. Yield: 170 mg (80%).

m.p. 124.4° to 125.2° C.

$^1$H NMR(500 MHz, CDCl$_3$) δ ppm 7.31–7.18(m, 10H), 5.54(d, 1H, J=9.5 Hz), 4.52(ddd, 1H, J=1.0 Hz), 4.26(broad q, 1H), 3.62(d, 1H, J=14.7 Hz), 3.59(d, 1H, J=14.7 Hz), 2.88(dd, 1H, J=13.7, 7.5 Hz), 2.87(dd, 1H, J=13.7, 8.7 Hz), 2.82(dd, 1H, J=17.6, 11.1 Hz), 2.64(dd, 1H, J=7.6, 7.9 Hz), 1.77(s, 3H).

IR(KBr, cm$^{-1}$)3367, 1651, 1526, 700.

$[\alpha]_D^{25}$+68° (c=1.2, CH$_3$OH). Mass spectrum (FD):m/z 322(M$^+$).

Anal. Calcd. for C$_{20}$H$_{22}$N$_2$O$_2$: C, 74.51;H, 6.88;N, 8.69%. Found: C, 74.41;H, 6.67;N, 8.64%.

[EXAMPLE 18]

(5RS,1'RS)-3-Phenylmethyl-5-(1'-acetylamino-2'-phenylethyl)-2-isoxazoline (5RS,1'RS)-3-Phenylmethyl-5-(1'-amino-2'-phenylethyl)-2-isoxazoline p-toluenesulfonate (250 mg, 0.55 mmol) prepared in Example 5 was suspended in ethanol (10 ml). To the suspension, anhydrous sodium acetate (45 mg, 0.55 mmol) and acetic anhydride (56 mg, 0.55 mmol) were added. The mixture was stirred at room temperature for 15 minutes, then concentrated under reduced pressure. Water and ethyl acetate were added to the residue for liquid separation. The organic layer was washed with saturated anhydrous sodium bicarbonate and then with water, followed by drying over anhydrous magnesium sulfate. The desiccant was filtered off. After the filtrate was concentrated to give crude crystals, the crude crystals were recrystallized from hexane/ethyl acetate to give the desired compound as colorless crystals. Yield: 147 mg (83%).

m.p. 97.8°–98.4° C.

$^1$H NMR(500 MHz, CDCl$_3$) δ ppm 7.31–7.18(m, 10H), 5.54(d, 1H, J=9.5 Hz), 4.52(ddd, 1H, J=1.0 Hz), 4.26(broad q, 1H), 3.62(d, 1H, J=14.7 Hz), 3.59(d, 1H, J=14.7 Hz), 2.88(dd, 1H, J=13.7, 7.5 Hz), 2.87(dd, 1H, J=13.7, 8.7 Hz), 2.82(dd, 1H, J=17.6, 11.1 Hz), 2.64(dd, 1H, J=17.6, 7.9 Hz), 1.77(s, 3H).

IR(KBr, cm$^{-1}$)3368, 1651, 1526, 700.

[EXAMPLE 19]

(5S,1'S)-3-Phenylmethyl-5-(1'-benzoylamino-2'-phenylethyl)-2-isoxazoline (5S,1'S)-3-Phenylmethyl-5-(1'-amino-2'-phenylethyl)-2-isoxazoline p-toluenesulfonate (300 mg, 0.66 mmol) prepared in a manner similar to that described in Example 1 (B) was suspended in tetrahydrofuran (5 ml) and cooled with ice. To the suspension, triethylamine (142 mg, 1.4 mmol) and benzoyl chloride (102 mg, 0.73 mmol) were added. The mixture was stirred at room temperature for 2 hours and the reaction mixture was concentrated under reduced pressure. Water and ethyl acetate were added to the residue for liquid separation. The organic layer separated was washed with saturated sodium bicarbonate water and then with water, followed by drying over anhydrous magnesium sulfate. After the desiccant was filtered off, the filtrate was concentrated to give crude crystals. The crude crystals were recrystallized from hexane/ethyl acetate to give the desired compound as colorless crystals. Yield: 224 mg (88%).

m.p. 147.0°–148.2° C.

$^1$H NMR(500 MHz, CDCl$_3$) δ ppm 7.63(d, 2H), 7.52(t, 1H), 7.43(t, 2H), 7.31–7.05(m, 10H), 6.26(d, 1H, J=9.8 Hz), 4.63(dd, 1H), 4.50(broad q, 1H), 3.58(d, 1H, J=14.9 Hz), 3.54(d, 1H, J=14.9 Hz), 3.03(dd, 1H, J=13.6, 6.9 Hz), 2.98(dd, 1H, J=13.6, 9.1 Hz), 2.85(dd, 1H, J=17.7, 11.1 Hz), 2.72(dd, 1H, J=17.7, 7.9 Hz).

IR(KBr, cm$^{-1}$)3373, 1643, 1518, 726, 695.

$[\alpha]_D^{25}$+109° (c=1.2, CHCl$_3$).

Mass spectrum (FD):m/z 384(M$^+$).

Anal. Calcd. for C$_{25}$H$_{24}$N$_2$O$_2$: C, 78.10;H, 6.29;N, 7.29%. Found: C, 78.03;H, 6.29;N, 7.16%.

[EXAMPLE 20]

(5RS,1'RS)-3-Phenylmethyl-5-(1'-benzoylamino-2'-phenylethyl)-2-isoxazoline (5RS,1'RS)-3-Phenylmethyl-5-(1'-amino-2'-phenylethyl)-2-isoxazoline p-toluenesulfonate (250 mg, 0.55 mmol) prepared in Example 5 was suspended in tetrahydrofuran (10 ml) and cooled with ice. To the suspension, triethylamine (111 mg, 1.1 mmol) and benzoyl chloride (77 mg, 0.55 mmol) were added. The mixture was stirred at room temperature for 4 hours, then concentrated under reduced pressure. Water and ethyl acetate were added to the residue for liquid separation. The organic layer separated was washed with saturated aqueous sodium bicarbonate and then with water, followed by drying over anhydrous magnesium sulfate. After the desiccant was filtered off, the filtrate was concentrated to give crude crystals. The crude crystals were recrystallized from hexane/ethyl acetate to give the desired compound as colorless crystals. Yield: 172 mg (81%).

m.p. 140.9°–141.7° C.

$^1$H NMR(500 MHz, CDCl$_3$) δ ppm 7.63(d, 2H), 7.52(t, 1H), 7.43(t, 2H), 7.31–7.05(m, 10H), 6.26(d, 1H, J=9.8 Hz), 4.63(dd, 1H),4.50(broad q, 1H), 3.58(d, 1H, J=14.9 Hz), 3.54(d, 1H, J=14.9 Hz), 3.03(dd, 1H, J=13.6, 6.9 Hz), 2.98(dd, 1H, J=13.6, 9.1 Hz), 2.85(dd, 1H, J=17.7, 11.1 Hz), 2.72(dd, 1H, J=17.7, 7.9 Hz).

IR(KBr, cm$^{-1}$)3333, 1638, 1540, 701, 694.

[EXAMPLE 21]

(5S,1'S)-3-Phenylmethyl-5-(1'-N,N-dibenzylamino-2'-phenylethyl)-2-isoxazoline

Potassium carbonate (31.9 g, 301 mmol), water (47.8 g), and benzyl chloride (35.3 g, 279 mmol) were added to (5S,1'S)-3-phenylmethyl-5-(1'-amino-2'-phenylethyl)-2-isoxazoline (28.5 g, 102 mmol) prepared from (5S,1'S)-3-phenylmethyl-5-(1'-amino-2'-phenylethyl)-2-isoxazoline p-toluenesulfonate prepared in a manner similar to that described in Example 1 (B). The resulting mixture was stirred at 80° C. for 63 hours. Toluene (516 g) was added to the reaction mixture, the mixture thus obtained was separated, and the organic layer separated was washed with water (285 g). The organic layer was concentrated under reduced pressure to give an oil (59 g). The oil (55 g) was crystallized from isopropyl alcohol (330 ml) to give the desired compound as colorless crystals. Yield: 37.68 g (87%).

m.p. 125.5°–126.4° C.

$^1$H NMR(500 MHz, CDCl$_3$) δ ppm 7.33–7.11(m, 20H), 4.46(dt, 1H, J=10.8, 4.0 Hz), 4.06(d, 2H, J=13.5 Hz), 3.66(s, 2H), 3.54(d, 2H, J=13.5 Hz), 3.07(dd, 1H, J=13.1, 5.0 Hz), 2.91(m, 2H), 2.41(dd, 2H, J=16.9, 10.8 Hz).

IR(KBr, cm$^{-1}$)3022, 2803, 1495, 1453, 857, 756, 701.

Mass spectrum (FD):m/z 461(M$^+$+H).

[EXAMPLE 22]

(5S,1'S)-3-Phenylmethyl-5-(1'-amino-2'-phenylethyl)-2-isoxazoline (5S,1'S)-3-Phenylmethyl-5-(1'-amino-2'-phenylethyl)-2-isoxazoline p-toluenesulfonate (200 mg, 0.44 mmol) prepared in a manner similar to that described in Example 1 (B) was suspended in methylene chloride (25 ml). To the suspension, a 10% aqueous sodium hydroxide (8 ml) was added to neutralize the sulfonate, followed by liquid separation. After the organic layer was washed and dried over anhydrous magnesium sulfate. After the desiccant was filtered off, the filtrate was concentrated under reduced pressure to give colorless crystals. Yield: 120 mg (97%).

m.p. 47.0° to 49.0° C.

$^1$H NMR(500 MHz, CDCl$_3$) δ ppm 7.34–7.15(m, 10H), 4.45(ddd, 1H), 3.68(s, 2H), 2.90(dt, 1H, J=4.8 Hz), 2.82(dd, 1H, J=17.1, 10.6 Hz), 2.78(dd, 1H, J=13.4, 4.5 Hz), 2.75(dd, 1H, J=17.1, 8.2 Hz), 2.55(dd, 1H, J=13.4, 8.9 Hz).

IR(KBr, cm$^{-1}$)3028, 2921, 1563, 1495, 1453, 872, 857, 826, 733, 707, 697.

[α]$_D^{25}$+152° (c=1.0, CH$_3$OH).

Mass spectrum (FD):m/z 281(M$^+$+H).

Anal. Calcd. for C$_{18}$H$_{20}$N$_2$O: C, 77.11;H, 7.19;N, 9.99%. Found: C, 77.29;H, 7.29;N, 9.93%.

[EXAMPLE 23]

(5RS,1'RS)-3-Phenylmethyl-5-(1'-amino-2'-phenylethyl)-2-isoxazoline (5RS,1'RS)-3-Phenylmethyl-5-(1'-amino-2'-phenylethyl)-2-isoxazoline p-toluenesulfonate (200 mg, 0.44 mmol) prepared in Example 5 was suspended in methylene chloride (25 ml). To the suspension, a 10% aqueous sodium hydroxide (8 ml) was added to neutralize the sulfonate, followed by liquid separation. After the organic layer was washed with water and dried over anhydrous magnesium sulfate. After the desiccant was filtered off, the filtrate was concentrated under reduced pressure to give an oil. Yield 130 mg.

$^1$H NMR(500 MHz, CDCl$_3$) δ ppm 7.34–7.15(m, 10H), 4.45(ddd, 1H), 3.68(s, 2H), 2.90(dt, 1H, J=4.8 Hz), 2.82(dd, 1H, J=17.1, 10.6 Hz), 2.78(dd, 1H, J=13.4, 4.5 Hz), 2.75(dd, 1H, J=17.1, 8.2 Hz), 2.55(dd, 1H, J=13.4, 8.9 Hz) IR(KBr, cm$^{-1}$)3026, 2917, 1602, 1583, 1494, 1454, 860, 745, 701

[EXAMPLE 24]

(5S,1'S)-3-Phenylmethyl-5-(1'-amino-2'-phenylethyl)-2-isoxazoline hydrochloride (5S,1'S)-3-Phenylmethyl-5-(1'-amino-2'-phenylethyl)-2-isoxazoline p-toluenesulfonate (250 mg, 0.55 mmol) prepared in a manner similar to that described in Example 1 (B) was suspended in ethyl acetate (25 ml). To the suspension, a 10% aqueous sodium hydroxide (8 m) was added to neutralize the sulfonate, followed by liquid separation. After the organic layer was washed with water and dried over anhydrous magnesium sulfate. After the desiccant was filtered off, the filtrate was concentrated under reduced pressure. The resulting oil containing (5S,1'S)-3-phenylmethyl-5-(1'-amino-2'-phenylethyl)-2-isoxazoline was dissolved in ethanol (5 ml), and conc. hydrochloric acid (0.1 ml) was added. The mixture was concentrated under reduced pressure. Ethanol and toluene were added to the residue, followed by concentration under reduced pressure. Crude crystals of the residue were recrystallized from ethanol/ethyl acetate to give the desired compound as colorless crystals. Yield; 105 mg (60%).

m.p. 188.0°–190.5° C. (decomposed).

$^1$H NMR(500 MHz, CD$_3$OD) δ ppm 7.34–7.18(m, 10H), 4.53(dt, 1H, J=7.7 Hz),3.67(d, 1H, J=14.9 Hz), 3.66(d, 1H, J=14.9 Hz), 3.44(q, 1H), 2.98(dd, 1H, J=17.7, 10.7 Hz), 2.93(dd, 1H, J=14.2, 6.7 Hz), 2.86(dd, 1H, J=14.2, 7.4 Hz), 2.62(dd, 1H, J=17.7, 7.4 Hz).

IR(KBr, cm$^{-1}$)3026, 2877, 1604, 1581, 1510, 1493, 1455, 862, 703

[α]$_D^{25}$+113 (c=1.0, CH$_3$OH).

Mass spectrum (FD):m/z 281(M$^+$-Cl).

Anal. Calcd. for the adduct C$_{18}$H$_{21}$N$_2$OCl 0.25H$_2$O: C, 67.28;H, 6.74;N, 8.72%. Found: C, 67.28;H, 6.64;N, 8.71%.

[EXAMPLE 25]

(A) (5S,1'S)-3-Phenylmethyl-5-(1'-tert-butoxycarbonylamino-2'-phenylethyl)-2-isoxazoline and (5R,1'S)-3-phenylmethyl-5-(1'-tert-butoxycarbonylamino-2'-phenylethyl)-2-isoxazoline (S)-3-tert-butoxycarbonylamino-4-phenyl-1-butene (1.236 g, 5 mmol) and phenylacetohydroximoyl chloride (1.701 g, 10 mmol) obtained in a manner similar to that described in Example 2 (B) were dissolved in toluene (6 ml). To the solution, triethylamine (1.219 g, 12 mmol) in toluene (12 ml) was added dropwise at room temperature over 2 hours. After the mixture was stirred at room temperature for 1.5 hour, water was added, followed by extraction with additional toluene. The organic phase was concentrated under reduced pressure to give a yellow liquid (2.90 g)

containing (5S,1'S)-3-phenylmethyl-5-(1'-tert-butoxycarbonylamino-2'-phenylethyl)-2-isoxazoline and (5R,1'S)-3-phenylmethyl-5-(1'-tert-butoxycarbonylamino-2'-phenylethyl)-2-isoxazoline. Reversed phase HPLC revealed that the ratio of (5S,1'S)-3-phenylmethyl-5-(1'-tert-butoxycarbonylamino-2'-phenylethyl)-2-isoxazoline to (5R,1'S)-3-phenylmethyl-5-(1'-tert-butoxycarbonylamino-2'-phenylethyl)-2-isoxazoline was 7:3. This yellow liquid was used in the next step without purification.

(B) (5S,1'S)-3-Phenylmethyl-5-(1'-amino-2'-phenylethyl)-2-isoxazoline and (5R,1'S)-3-phenylmethyl-5-(1'-amino-2'-phenylethyl)-2-isoxazoline A liquid (2.69 g) containing (5S,1'S)-3-phenylmethyl-5-(1'-tert-butoxycarbonylamino-2'-phenylethyl)-2-isoxazoline and (5R,1'S)-3-phenylmethyl-5-(1'-tert-butoxycarbonylamino-2'-phenylethyl)-2-isoxazoline obtained in Example 25 (A) was dissolved in methylene chloride (8 ml). To the solution, trifluoroacetic acid (4 ml) was added at room temperature. After the mixture was stirred at room temperature for 35 minutes, a 10% aqueous sodium hydroxide was added. After extraction with methylene chloride, the mixture was dried over anhydrous magnesium sulfate. After the desiccant was filtered off, the filtrate was concentrated under reduced pressure to give a yellow liquid (2.04 g) containing the desired compound. This yellow liquid was used in the next step without purification.

(C) (5S,1'S)-3-Phenylmethyl-5-(1'-amino-2'-phenylethyl)-2-isoxazoline hydrochloride A liquid (2.04 g) containing (5S,1'S)-3-phenylmethyl-5-(1'-amino-2'-phenylethyl)-2-isoxazoline and (5R,1'S)-3-phenylmethyl-5-(1'-amino-2'-phenylethyl)-2-isoxazoline obtained in Example 25 (B) was dissolved in isopropyl alcohol (20 ml). Hydrogen chloride gas was added into the solution at room temperature. The resulting solution was heated to dissolve, and then diisopropyl ether (10 ml) was added thereto, followed by cooling. Crystals precipitated were filtered under reduced pressure, and washed with isopropyl alcohol/diisopropyl ether (1/1). From a solid (0.700 g) obtained by drying under reduced pressure, a portion of 0.600 g was recrystallized from isopropyl alcohol to give the desired compound as light khaki crystals (0.325 g).

The obtained compound agreed with the compound obtained in Example 24.

[EXAMPLE 26]

(5RS,1'RS)-3-Phenylmethyl-5-(1'-amino-2'-phenylethyl)-2-isoxazoline hydrochloride (5RS,1'RS)-3-Phenylmethyl-5-(1'-amino-2'-phenylethyl)-2-isoxazoline p-toluenesulfonate (250 mg, 0.55 mmol) prepared in Example 5 was suspended in ethyl acetate (25 ml). To the suspension, a 10% aqueous sodium hydroxide (8 ml) was added to neutralize the sulfonate, followed by liquid separation. After the organic layer was washed with water and dried over anhydrous magnesium sulfate. After the desiccant was filtered off, the filtrate was concentrated under reduced pressure. The resulting oil containing (5RS,1'RS)-3-phenylmethyl-5-(1'-amino-2'-phenylethyl)-2-isoxazoline was dissolved in ethanol (5 ml), and conc. hydrochloric acid (0.1 ml) was added. After the mixture was concentrated under reduced pressure, ethanol and toluene were added to the residue, followed by concentration under reduced pressure. Residual crude crystals were recrystallized from ethanol/diisopropyl ether to give the desired compound as colorless crystals.

Yield: 146 mg (84%).
m.p. 196.0°–198.0° C. (decomposed).

$^1$H NMR(500 MHz, CD$_3$OD) δ ppm 7.34–7.18(m, 10H), 4.53(dt, 1H, J=7.7 Hz), 3.67(d, 1H, J=14.9 Hz), 3.66(d, 1H, J=14.9 Hz), 3.44(q, 1H), 2.98(dd, 1H, J=17.7, 10.7 Hz), 2.93(dd 1H, J=14.2, 6.7 Hz), 2.86(dd, 1H, J=14.2, 7.4 Hz), 2.62(dd, 1H, J=17.7, 7.4 Hz).

IR(KBr, cm$^{-1}$)3027, 2926, 1604, 1578, 1508, 1494, 1455, 859, 700

[EXAMPLE 27]

(5S,1'S)-3-Phenylmethyl-5-(1'-amino-2'-phenylethyl)-2-isoxazoline benzenesulfonate (5S,1'S)-3-Phenylmethyl-5-(1'-amino-2'-phenylethyl)-2-isoxazoline p-toluenesulfonate (250 mg, 0.55 mmol) prepared in a manner similar to that described in Example 1 (B) was suspended in ethyl acetate (25 ml). To the suspension, a 10% aqueous sodium hydroxide (8 ml) was added to neutralize the sulfonate, followed by liquid separation. After the organic layer was washed and dried over anhydrous magnesium sulfate. After the desiccant was filtered off, the filtrate was concentrated under reduced pressure. The resulting oil containing (5S,1'S)-3-phenylmethyl-5-(1'-amino-2'-phenylethyl)-2-isoxazoline was dissolved in a small amount of ethanol. Benzenesulfonic acid monohydrate (104 mg, 0.6 mmol) was added to the solution for crystallization. The crystals were recrystallized from ethanol/ethyl acetate to give the desired compound as colorless crystals. Yield: 165 mg (68%)

m.p. 218.0° to 219.0° C. (decomposed).

$^1$H NMR(500 MHz, CD$_3$OD) δ ppm 7.84–7.18(m, 15H), 4.53(dt, 1H), 3.67(d, 1H, J=14.9 Hz), 3.64(d, 1H, J=14.9 Hz), 3.45(q, 1H, J=7.6 Hz), 2.94(dd, 1H, J=17.7, 10.7 Hz), 2.90(dd, 1H, J=14.5, 7.2 Hz), 2.87(dd, 1H, J=14.5, 7.4 Hz), 2.62(dd, 1H, J=17.7, 7.6 Hz).

IR(KBr, cm$^{-1}$)3052, 2925, 1633, 1526, 1210, 1185, 1128, 1036, 1017, 729, 700, 690, 614, 569.

$[α]_D^{25}$+84° (c=1.1, CH$_3$OH).

Mass spectrum (FD):m/z 281(M$^+$-PhSO$_3$).

Anal. Calcd. for C$_{24}$H$_{26}$N$_2$O$_4$S: C, 65.73;H, 5.98;N, 6.39%. Found: C, 65.98;H, 5.93;N, 6.14%.

[EXAMPLE 28]

(5RS,1'RS)-3-Phenylmethyl-5-(1'-amino-2'-phenylethyl)-2-isoxazoline benzenesulfonate (5RS,1'RS)-3-Phenylmethyl-5-(1'-amino-2'-phenylethyl)-2-isoxazoline p-toluenesulfonate (250 mg, 0.55 mmol) prepared in Example 5 was suspended in ethyl acetate (25 ml). To the suspension, a 10% aqueous sodium hydroxide (8 ml) was added to neutralize the sulfonate, followed by liquid separation. After the organic layer was washed with water and dried over anhydrous magnesium sulfate. After the desiccant was filtered off, the filtrate was concentrated under reduced pressure. The resulting oil containing (5RS,1'RS)-3-phenylmethyl-5-(1'-amino-2'-phenylethyl)-2-isoxazoline was dissolved in a small amount of ethanol. Benzenesulfonic acid monohydrate (97 mg, 0.55 mol) was added to the solution for crystallization. The crystals were recrystallized from ethanol/ethyl acetate to give colorless crystals. Yield: 198 mg (82%).

m.p. 210.0°–212.0° C. (decomposed).

$^1$H NMR(500 MHz, CD$_3$OD) δ ppm 7.84–7.18(m, 15H), 4.53(dt, 1H), 3.67(d, 1H , J=14.9 Hz), 3.64(d, 1H, J=14.9 Hz), 3.45(q, 1H, J=7.6 Hz), 2.94(dd, 1H, J=17.7, 10.7 Hz), 2.90(dd, 1H, J=14.5, 7.2 Hz), 2.87(dd, 1H, J=14.5, 7.4 Hz), 2.62(dd, 1H, J=17.7, 7.6 Hz).

IR(KBr, cm$^{-1}$)3063, 2948, 1637, 1526, 1209, 1181, 1128, 1035, 1016, 729, 699, 690, 612.

[EXAMPLE 29]
(5S,1'S)-3-Phenylmethyl-5-(1'-amino-2'-phenylethyl)-2-isoxazoline methanesulfonate (5S,1'S)-3-phenylmethyl-5-(1'-amino-2'-phenylethyl)-2-isoxazoline p-toluenesulfonate (250 mg, 0.55 mmol) prepared in a manner similar to that described in Example 1 (B) was suspended in ethyl acetate (25 ml). To the suspension, a 10% aqueous sodium hydroxide (8 ml) was added to neutralize the sulfonate, followed by liquid separation. After the organic layer was washed with water and dried over anhydrous magnesium sulfate. After the desiccant was filtered off, the filtrate was concentrated under reduced pressure. The resulting oil containing (5S,1'S)-3-phenylmethyl-5-(1'-amino-2'-phenylethyl)-2-isoxazoline was dissolved in a small amount of ethanol. Methanesulfonic acid (57 mg, 0.6 mmol) and diisopropyl ether were added to the mixture for crystallization to give the desired compound. Crystals, thus obtained, was colorless. Yield: 116 mg (56%).

m.p. 121.0°–125.0° C. (decomposed).

$^1$H NMR(500 MHz, CD$_3$OD) δ ppm 7.34–718(m, 10H), 4.52(dt, 1H), 3.67(d, 1H, J=14.9 Hz), 3.66(d, 1H, J=14.9 Hz), 3.44(q, 1H, J=7.7 Hz), 2.98(dd, 1H, J=17.8, 10.5 Hz), 2.93(dd, 1H, J=13.6, 6.7 Hz), 2.87(dd, 1H, J=13.6, 7.3 Hz), 2.68(s, 3H), 2.61 (dd, 1H, J=17.8, 7.5 Hz).

IR(KBr, cm$^{-1}$)3025, 2918, 1626, 1600, 1493, 1451, 1344, 1209, 1195, 1042, 859, 772, 701.

$[\alpha]_D^{25}$+93° (c=1.1, CH$_3$OH).

Mass spectrum (FD):m/z 281(M$^+$-MsO).

Anal. Calcd. for the adduct C$_{19}$H$_{24}$N$_2$O$_4$S.0.5H$_2$O: C, 59.20;H, 6.54;N, 7.27% Found: C, 59.02;H, 6.43;N, 7.05%

[EXAMPLE 30]
(5RS,1'RS)-3-Phenylmethyl-5-(1'-amino-2'-phenylethyl)-2-isoxazoline methanesulfonate (5RS,1'RS)-3-Phenylmethyl-5-(1'-amino-2'-phenylethyl)-2-isoxazoline p-toluenesulfonate (250 mg, 0.55 mmol) prepared in Example 5 was suspended in ethyl acetate (25 ml). To the suspension, a 10% aqueous sodium hydroxide (8 ml) was added to neutralize the sulfonate, followed by liquid separation. The organic layer separated was washed with water and dried over anhydrous magnesium sulfate. After the desiccant was filtered off, the filtrate was concentrated under reduced pressure. The resulting oil containing (5RS,1'RS)-3-phenylmethyl-5-(1'-amino-2'-phenylethyl)-2-isoxazoline was dissolved in a small amount of ethanol. Methanesulfonic acid (53 mg, 0.55 mmol) was added to the solution. The mixture was recrystallized from ethanol/diisopropyl ether to give the desired compound as colorless crystals. Yield: 190 mg (92%).

m.p. 159.0°–161.0° C. (decomposed).

$^1$H NMR(500 MHz, CD$_3$OD) δ ppm 7.34–7.18(m, 10H), 4.52(dt, 1H), 3.67(d, 1H, J=14.9 Hz), 3.66(d, 1H, J=14.9 Hz), 3.44(q, 1H, J=7.7 Hz), 2.98(dd, 1H, J=17.8, 10.5 Hz), 2.93(dd, 1H, J=13.6, 6.7 Hz), 2.87(dd, 1 H, J=13.6, 7.3 Hz), 2.68(s, 3H), 2.61 (dd, 1H, J=17.8, 7.5 Hz).

IR(KBr, cm$^{-1}$)3027, 2934, 1617, 1547, 1494, 1244, 1194, 1142, 1033, 702, 558.

[EXAMPLE 31]
(5S,1'S)-3-Phenylmethyl-5-(1'-amino-2'-phenylethyl)-2-isoxazoline benzoate (5S,1'S)-3-Phenylmethyl-5-(1'-amino-2'-phenylethyl)-2-isoxazoline p-toluenesulfonate (250 mg, 0.55 mmol) prepared in a manner similar to that described in Example 1 (B) was suspended in ethyl acetate (25 ml). To the suspension, a 10% aqueous sodium hydroxide (8 ml) was added to neutralize the sulfonate, followed by liquid separation. The organic layer was washed with water and dried over anhydrous magnesium sulfate. After the desiccant was filtered off, the filtrate was concentrated under reduced pressure. The resulting oil containing (5S,1'S)-3-phenylmethyl-5-(1'-amino-2'-phenylethyl)-2-isoxazoline was dissolved in a small amount of ethanol. Benzoic acid (72 mg, 0.6 mmol) was added to the solution and crystals were precipitated. The resulting crude crystals were recrystallized from ethanol/diisopropyl ether to give the desired compound as colorless crystals.

Yield; 135 mg (61%).

m.p. 128.5°–129.5° C.

$^1$H NMR(500 MHz, CD$_3$OD) δ ppm 7.95(m, 2H), 7.44(m, 1H), 7.37(m, 2H), 7.32–7.16(m, 10H), 4.48(dt, 1H, J=7.4 Hz), 3.66(d, 1H, J=14.9 Hz), 3.65(d, 1H, J=14.9 Hz), 3.27(q, 1H), 2.92(dd, 1H, J=17.7, 10.7 Hz), 2.85(dd, 1H, J=13.9, 6.4 Hz), 2.77(dd, 1H, J=13.9, 7.7 Hz), 2.65(dd, 1H, J=17.7, 7.8 Hz).

IR(KBr, cm$^{-1}$)3058, 3027, 2917, 1629, 1592, 1565, 1506, 1455, 1444, 1426, 1396, 1383, 719, 708, 696.

$[\alpha]_D^{25}$+95° (c=1.2, CH$_3$OH).

Mass spectrum(FD):m/z 281(M$^+$-PhCOO).

Anal. Calcd. for C$_{25}$H$_{26}$N$_2$O$_3$: C, 74.60;H, 6.51;N, 6.96%. Found: C, 74.35;H, 6.57;N, 6.80%.

[EXAMPLE 32]
(5RS,1'RS)-3-Phenylmethyl-5-(1'-amino-2'-phenylethyl)-2-isoxazoline benzoate (5RS,1'RS)-3-Phenylmethyl-5-(1'-amino-2'-phenylethyl)-2-isoxazoline p-toluenesulfonate (250 mg, 0.55 mmol) prepared in Example 5 was suspended in ethyl acetate (25 ml). To the suspension, a 10% aqueous sodium hydroxide (8 ml) was added to neutralize the sulfonate, followed by liquid separation. The organic layer was washed with water and dried over anhydrous magnesium sulfate. After the desiccant was filtered off, the filtrate was concentrated under reduced pressure. The resulting oil containing (5RS,1'RS)-3-phenylmethyl-5-(1'-amino-2'-phenylethyl)-2-isoxazoline was dissolved in a small amount of ethanol. Benzoic acid (72 mg, 0.6 mmol) was added to the solution and crystals were separated. The resulting crude crystals were recrystallized from ethanol/diisopropyl ether to give the desired compound as colorless crystals. Yield: 131 mg (59%).

m.p. 119.0°–120.5° C.

$^1$H NMR(500 MHz, CD$_3$OD) δ ppm 7.95(m, 2H), 7.44(m, 1H), 7.37(m, 2H), 7.32–7.16(m, 10H), 4.48(dt, 1H, J=7.4 Hz), 3.66(d, 1H, J=14.9 Hz), 3.65(d, 1H, J=14.9 Hz), 3.27(q, 1H), 2.92(dd, 1H, J=17.7, 10.7 Hz), 2.85(dd, 1H, J=13.9, 6.4 Hz), 2.77(dd, 1H, J=13.9, 7.7 Hz), 2.65(dd, 1H, J=17.7, 7.8 Hz).

IR(KBr, cm$^{-1}$)3057, 3027, 2921, 1629, 1592, 1563, 1496, 1455, 1444, 1428, 1393, 1380, 719, 706.

[EXAMPLE 33]
(5S,1'S)-3-Phenylmethyl-5-(1'-amino-2'-phenylethyl)-2-isoxazoline oxalate (5S,1'S)-3-Phenylmethyl-5-(1'-amino-2'-phenylethyl)-2-isoxazoline p-toluenesulfonate (250 mg, 0.55 mmol) prepared in a manner similar to that described in Example 1 (B) was suspended in ethyl acetate (25 ml). To the suspension, a 10% aqueous sodium hydroxide (8 ml) was added to neutralize the sulfonate, followed by liquid separation. The organic layer was washed with water and dried over anhydrous magnesium sulfate. After the desiccant was filtered off, the filtrate was concentrated under reduced pressure. The resulting oil containing (5S,1'S)-3-phenylmethyl-5-(1'-amino-2'-phenylethyl)-2-isoxazoline was dissolved in a small amount of ethanol. Oxalic acid dihydrate (74 mg, 0.6 mmol) was added to the solution, and crystals were separated. The resulting crude crystals were recrystallized from methanol/diisopropyl ether to give the desired compound as colorless crystals. Yield: 176 mg (86%).

m.p. 190.0–191.0° C. (decomposed).

$^1$H NMR(500 MHz, CD$_3$OD) δ ppm 7.33–7.18(m, 10H), 4.54(dt, 1H, J=7.6 Hz), 3.66(d, 1H, J=14.9 Hz), 3.65(d, 1H, J=14.9 Hz), 3.45(q, 1H), 2.96(dd, 1H, J=17.7, 10.7 Hz), 2.91(m, 2H, J=14.2, 7.2, 7.1 Hz), 2.62(dd, 1H, J=17.7, 7.5 Hz).

IR(KBr, cm$^{-1}$)3084, 3061, 3030, 2935, 1740, 1702, 1677, 1604, 1533, 1493, 1455, 1444, 892, 857, 696.

$[α]_D^{25}$+99° (c=1.2, CH$_3$OH).

Mass spectrum (FD):m/z 281(M$^+$-C$_2$HO$_4$).

Anal. Calcd. for C$_{20}$H$_{24}$N$_2$O$_5$: C, 64.85;H, 5.99;N, 7.56%. Found: C, 64.64;H, 5.97;N, 7.42%.

[EXAMPLE 34]

(5RS,1'RS)-3-Phenylmethyl-5-(1'-amino-2'-phenylethyl)-2-isoxazoline oxalate (5RS,1'RS)-3-Phenylmethyl-5-(1'-amino-2'-phenylethyl)-2-isoxazoline p-toluenesulfonate (250 mg, 0.55 mmol) prepared in Example 5 was suspended in ethyl acetate (25 ml). To the suspension, a 10% aqueous sodium hydroxide (8 ml) was added to neutralize the sulfonate, followed by liquid separation. The organic layer was washed with water and dried over anhydrous magnesium sulfate. After the desiccant was filtered off, the filtrate was concentrated under reduced pressure. The resulting oil containing (5RS,1'RS)-3-phenylmethyl-5-(1'-amino-2'-phenylethyl)-2-isoxazoline was dissolved in a small amount of ethanol. Oxalic acid dihydrate (70 mg, 0.55 mmol) was added to the solution and crystals were separated. The resulting crude crystals were recrystallized from methanol/diisopropyl ether to give the desired compound as colorless crystals.

Yield: 175 mg (86%).

m.p. 176.0° to 177.5° C. (decomposed).

$^1$H NMR(500 MHz, CD$_3$OD) δ ppm 7.33–7.18(m, 10H), 4.54(dt, 1H, J=7.6 Hz), 3.66(d, 1H, J=14.9 Hz), 3.65(d, 1H, J=14.9 Hz), 3.45(q, 1H), 2.96(dd, 1H, J=17.7, 10.7 Hz), 2.91 (m, 2H, J=14.2, 7.1, 7.2 Hz), 2.62(dd, 1H, J=17.7, 7.5 Hz).

IR(KBr, cm$^{-1}$)3029, 2928, 1720, 1702, 1603, 1528, 1494, 1455, 1215, 895, 857, 719, 704.

[EXAMPLE 35]

(5S,1'S)-3-Phenylmethyl-5-(1'-amino-2'-phenylethyl)-2-isoxazoline (S)-mandelate (5RS,1'RS)-3-Phenylmethyl-5-(1'-amino-2'-phenylethyl)-2-isoxazoline (2.1 g, 7.50 mmol) prepared in a manner similar to that described in Example 23 was dissolved in isopropyl alcohol (5 ml). The solution was added to an isopropyl alcohol solution (15 ml) of (S)-mandelic acid (1.13 g, 7.50 mmol). After the mixture was stirred for 5 minutes while being refluxed, the mixture was allowed to stand at room temperature for 6 hours. Crystals precipitated were filtered under reduced pressure to give (5S-1'S)-3-phenylmethyl-5-(1'-amino-2'-phenylethyl)-2-isoxazoline (S)-mandelate (1.12 g, 2.59 mmol) as colorless crystals. Yield of (5S,1'S)-3-phenylmethyl-5-(1'-amino-2'-phenylethyl)-2-isoxazoline based on the starting material (5RS,1'RS)-3-phenylmethyl-5-(1'-amino-2'-phenylethyl)-2-isoxazoline was 69%. HPLC using CHIRALPAK AS (trade name) revealed that optical purity of the obtained (5S,1'S)-3-phenylmethyl-5-(1'-amino-2'-phenylethyl)-2-isoxazoline (S)-mandelate was not less than 99%.

m.p. 129.5°–130.0° C.

$^1$H NMR(500 MHz, CDCl$_3$) δ ppm 7.43(d, 2H, J=7.5 Hz), 7.33–7.13(m, 11H), 7.04(dd, 2H, J=6.4, 1.6 Hz), 4.97(s, 1H), 4.48(broad s, 4H), 4.38–4.32(m, 1H), 3.62(d, 1H, J=14.9 Hz), 3.52(d, 1H, J=14.9 Hz), 3.02(q, 1H, J=6.1 Hz), 2.72–2.66(m, 2H), 2.54(dd, 1H, J=17.5, 7.6 Hz).

IR(KBr, cm$^{-1}$)3482, 3084, 3060, 3028, 3004, 2934, 1630, 1604, 1561, 1494, 1452, 1438, 1400, 1356, 1191, 1082, 1072, 1058, 854, 750, 732, 700.

$[α]_D^{25}$+128.2° (c=0.99, CH$_3$OH).

Mass spectrum (FD):m/z 281(M$^+$-PhCHOHCOO).

Anal. Calcd. for C$_{26}$H$_{28}$N$_2$O$_4$: C, 72.23;H, 6.53;N, 6.48%. Found: C, 72.27;H, 6.54;N, 6.41%.

[EXAMPLE 36]

(5R,1'R)-3-Phenylmethyl-5-(1'-amino-2'-phenylethyl)-2-isoxazoline (R)-mandelate

The mixture (1.18 g, 4.18 mmol) containing (5R,1'R)-3-phenylmethyl-5-(1'-amino-2'-phenylethyl)-2-isoxazoline as a major component and (5S,1'S)-3-phenylmethyl-5-(1'-amino-2'-phenylethyl)-2-isoxazoline prepared in a manner similar to that of Example 23 from a mother liquor of Example 35, was dissolved in isopropyl alcohol (3 ml). The solution was added to isopropyl alcohol (9 ml) containing (R)-mandelic acid(0.64 g, 4.18 mmol). After the mixture was stirred for 5 minutes while being refluxed, the mixture was allowed to stand at room temperature for 6 hours. Crystals precipitated were filtered under reduced pressure to give (5R,1'R)-3-phenylmethyl-5-(1'-amino-2'-phenylethyl)-2-isoxazoline (R)-mandelate (1.36 g, 3.15 mmol) as colorless crystals. Yield of (5R,1'R)-3-phenylmethyl-5-(1'-amino-2'-phenylethyl)-2-isoxazoline based on the starting material (5RS,1'RS)-3-phenylmethyl-5-(1'-amino-2'-phenylethyl)-2-isoxazoline of Example 35 was 82%. HPLC using CHIRALPAK AS (trade name) revealed that optical purity of the obtained (5R,1'R)-3-phenylmethyl-5-(1'-amino-2'-phenylethyl)-2-isoxazoline (R)-mandelate was 97.9%.

m.p. 129.3°–129.8 ° C.

$^1$H NMR(500 MHz, CDCl$_3$) δ ppm 7.43(d, 2H, J=7.5 Hz), 7.33–7.13(m, 11H), 7.04(dd, 2H, J=6.4, 1.6 Hz), 4.97(s, 1H), 4.48(broad s, 4H), 4.38–4.32(m, 1H), 3.62(d, 1H, J=14.9 Hz), 3.52(d, 1H, J=14.9 Hz), 3.02(q, 1H, J=6.1 Hz), 2.72–2.66(m, 2H), 2.54(dd, 1H, J=17.5, 7.6 Hz).

IR(KBr, cm$^{-1}$)3482, 3084, 3060, 3028, 3004, 2934, 1630, 1604, 1561, 1494, 1452, 1438, 1400, 1356, 1191, 1082, 1072, 1058, 854, 750, 732, 700.

$[α]_D^{25}$–130.8° (c=1.14, CH$_3$OH).

Mass spectrum (FD):m/z 281(M$^+$-PhCHOHCOO).

Anal. Calcd. for C$_{26}$H$_{28}$N$_2$O$_4$: C, 72.23;H, 6.53;N, 6.48%. Found: C, 71.98;H, 6.44;N, 6.46%.

[EXAMPLE 37]

(A) (5RS,1'RS)-3-Phenylmethyl-5-(1'-amino-2'-phenylethyl)-2-isoxazoline (5RS,1'RS)-3-Phenylmethyl-5-(1'-tert-butoxycarbonylamino-2'-phenylethyl)-2-isoxazoline (100 mg) was dissolved in methylene chloride (4 ml) and trifluoroacetic acid (1 ml) were added at room temperature. After the mixture was stirred at room temperature for 20 minutes, a 10% aqueous sodium hydroxide was added for neutralization in an ice-water bath. After being extracted with methylene chloride, the organic layer was dried over anhydrous magnesium sulfate. After the desiccant was filtered off, the filtrate was concentrated under reduced pressure to give the crude desired compound (77 mg) as a yellow liquid. The resulting yellow liquid agreed with the compound obtained in Example 23.

[EXAMPLE 38]
(5RS,1'RS)-3-Phenylmethyl-5-(1'-amino-2'-phenylethyl)-2-isoxazoline (5RS,1'RS)-3-Phenylmethyl-5-(1'-benzyloxycarbonylamino-2'-phenylethyl)-2-isoxazoline (9.6 mg) was dissolved in methanol (2 ml). Conc. hydrochloric acid (0.5 ml) was added to the solution. The mixture was stirred for 8.25 hours while being refluxed. After the mixture was allowed to stand overnight at room temperature, a 10% aqueous sodium hydroxide was added, followed by extraction with methylene chloride. The organic layer was dried over anhydrous magnesium sulfate. After the desiccant was filtered off, the filtrate was concentrated to give an oil (8.1 mg) containing the desired compound. The oil agreed with the compound obtained in Example 23.

[EXAMPLE 39]
(A) (2RS,3RS,5RS)-2-tert-Butoxycarbonylamino-3-hydroxy-5-amino-1,6-diphenylhexane To a methanol solution (2 ml) of (5RS,1'RS)-3-Phenylmethyl-5-(1'-tert-butoxycarbonylamino-2'-phenylethyl)-2-isoxazoline (10.6 mg), a 5% Pd-on-carbon catalyst (10.1 mg, 95% by weight based on substrate) was added. The mixture was stirred for 4 hours in a hydrogen atmosphere at atmospheric pressure. After the catalyst was filtered off under reduced pressure, the filtrate was concentrated under reduced pressure. The resulting foamy residue (9.7 mg) was purified by silica gel thin-layer chromatography (solvent for development, chloroform/methanol =10/1). (2RS,3RS,5RS)-2-tert-butoxycarbonylamino-3-hydroxy-5-amino-1,6-diphenylhexane was obtained as a colorless solid (8.4 mg).

$^1$H NMR(500 MHz, CDCl$_3$) δ ppm 7.29–7.06(m, 10H), 5.08(d, 1H, J=9.5 Hz), 3.77(d, 1H, J=10.1 Hz), 3.65(broad q, 1H), 3.01(m, 1H), 2.86(d, 2H, J=8.0 Hz), 2.77(dd, 1H, J=13.6, 4.6 Hz), 2.40(dd, 1 H, J=13.6, 8.5 Hz), 1.55–1.39(m, 2H) 1.42(s, 9H).

(B) (2RS,3RS,5RS)-2,5-Diamino-1,6-diphenyl-3-hydroxyhexane (2RS,3RS,5RS)-2-tert-Butoxycarbonylamino-3-hydroxy-5-amino-1,6-diphenylhexane obtained in Example 39 (A) was dissolved in methylene chloride (1 ml), and trifluoroacetic acid (0.5 ml) was added at room temperature. After the mixture was stirred at room temperature for 3 hours, a 10% aqueous sodium hydroxide was added. After being extracted with methylene chloride, the mixture was dried over anhydrous sodium sulfate. After the desiccant was filtered off, the filtrate was concentrated under reduced pressure to give the desired compound as a colorless solid (3.2 mg).

$^1$H NMR(500 MHz, CDCl$_3$) δ ppm 7.32–7.13(m, 10H), 3.73(dt, 1H, J=10.5, 3.2 Hz), 3.11(m, 1H), 2.89(dd, 1H, J=13.2, 8.5 Hz), 2.82(m, 2H), 2.57(dd, 1H, J=13.2, 8.8 Hz), 2.51(dd, 1H, J=13.5, 8, 3 Hz), 1.67(dt, 1H, J=14.0, 2.3 Hz), 1.53(dt, 1H, J=14.0, 10.6 Hz).

[EXAMPLE 40]
(2S,3S,5S)-2-tert-Butoxycarbonylamino-3-hydroxy-5-amino-1,6-diphenylhexane (5S,1')-3-Phenylmethyl-5-(1'-tert-butoxycarbonylamino-2'-phenylethyl)-2-isoxazoline (1.0 g, 2.64 mmol) was dissolved in methanol (10 ml). A 3% Pt-on-carbon catalyst (100 mg, 10% by weight based on substrate) was added thereto, and the mixture was stirred in a hydrogen atmosphere at atmospheric pressure for 42 hours. The catalyst was removed by filtration under reduced pressure, and then the filtrate was concentrated under reduced pressure. A foamy residue (0.99 g) containing (2S,3S,5S)-2-tert-butoxycarbonylamino-3-hydroxy-5-amino-1,6-diphenylhexane and (2S,3S,5R)-2-tert-butoxycarbonylamino-3-hydroxy-5-amino-1,6-diphenylhexane was obtained. By HPLC analysis of the residue (absolute calibration curve method) using CHIRALPAK AD (trade name), 0.38 g of (2S,3S,5S)-2-tert-butoxycarbonylamino-3-hydroxy-5-amino-1,6-diphenylhexane (yield: 38%) and 0.07 g of (2S,3S,5R)-2-tert-butoxycarbonylamino-3-hydroxy-5-amino-1,6-diphenylhexane (yield: 7%) were contained.

[EXAMPLE 41]
(2S,3S,5S)-2-tert-Butoxycarbonylamino-3-hydroxy-5-amino-1,6-diphenylhexane oxalate (5S,1'S)-3-Phenylmethyl-5-(1'-tert-butoxycarbonylamino-2'-phenylethyl)-2-isoxazoline (2.0 g, 5.26 mmol) was dissolved in an ammonia/methanol solution (3%, 20 ml). A 3% Pt-on-carbon catalyst (100 mg, 5% by weight based on substrate) was added thereto. The mixture was stirred for 21 hours in a hydrogen atmosphere at atmospheric pressure. The catalyst was removed by filtration under reduced pressure, and then the filtrate was concentrated under reduced pressure. A foamy residue (2.0 g) containing (2S,3S,5S)-2-tert-butoxycarbonylamino-3-hydroxy-5-amino-1,6-diphenylhexane and (2S,3S,5R)-2-tert-butoxycarbonylamino-3-hydroxy-5-amino-1,6-diphenylhexane was obtained. By the HPLC analysis of the residue (absolute calibration curve method) using CHIRALPAK AD (trade name), 1.47 g of (2S,3S,5S)-2-tert-butoxycarbonylamino-3-hydroxy-5-amino-1,6-diphenylhexane (yield: 73%) and 0.28 g of (2S,3S,5R)-2-tert-butoxycarbonylamino-3-hydroxy-5-amino-1,6-diphenylhexane (reaction yield: 14%) were contained. Oxalic acid dihydrate (633 mg, 5.26 mmol) was added to the residue, the mixture was heated to dissolved in aqueous methanol (water content: 20% v/v, 22 ml). When the mixture was dissolved, it was cooled and crystals precipitated were collected by filtration. The crystals were washed with aqueous methanol (water content: 20%) and dried under reduced pressure to give colorless crystals. By HPLC analysis of the crystals, (2S,3S,5S)-2-tert-butoxycarbonylamino-3-hydroxy-5-amino-1,6-diphenylhexane and (2S,3S,5R)-2-tert-butoxycarbonylamino-3-hydroxy-5-amino-1,6-diphenylhexane were contained in the ratio of 97:3. Part of the crystals were further recrystallized with aqueous methanol (water content: 20%) to give the pure desired compound in crystals, which were confirmed, by HPLC, not to contain (2S,3S,5R)-2-tert-butoxycarbonylamino-3-hydroxy-5-amino-1,6-diphenylhexane.

m.p. 194.0°–195.7° C. (decomposed).

$^1$H NMR(500 MHz, (CD$_3$)$_2$SO) δ ppm 7.33–7.13(m, 10H), 6.49(d, 1H, J=9.2 Hz), 3.65(m, 1H), 3.58(m, 1H), 3.47(m, 1H), 2.86(dd, 1H, J=14.0, 6.3 Hz), 2.79(dd, 1H, J=14.0, 7.2 Hz), 2.75(dd, 1H, J=13.5, 4.2 Hz), 2.59(dd, 1H, J=13.5, 10.2 Hz), 1.56(m, 2H), 1.25(s, 9H). In addition, there exists a rotational isomer (ppm 1.12(s)) with respect to the amide bond of tert-butoxycarbonyl group.

$[α]_D^{25}$–31.9° (c=1.33, (CH$_3$)$_2$SO).

Mass spectrum (FD):m/z 385(M$^+$-C$_2$HO$_4$).

Anal. Calcd. for the adduct C$_{25}$H$_{34}$N$_2$O$_7$ 0.3H$_2$O : C, 62.56;H, 7.27;N, 5.84%. Found: C, 62.62;H, 7.14;N, 5.81%.

[EXAMPLE 42]
(2S,3S,5S)-2,5-Diamino-3-hydroxy-1,6-diphenylhexane dihydrochloride Methylene chloride and a 5% aqueous NaOH were added to (2S,3S,5S)-2-tert-butoxycarbonylamino-3-hydroxy-5-amino-1,6-diphenylhexane oxalate (11.01 g, 23.2 mmol)

obtained in a manner similar to that described in Example 41. followed by extraction. The methylene chloride layer was concentrated under reduced pressure to give a residue (8.74 g) containing (2S,3S,5S)-2-tert-butoxycarbonylamino-3-hydroxy-5-amino-1,6-diphenylhexane. 2M HCl (75 ml) was added to the residue. The mixture was stirred for 1.5 hours in an oil bath at 110° C. Ethanol (600 ml) was added, the mixture was concentrated to give a residue (30.75 g). Methanol (60 ml) was added to the residue to dissolve it. Isopropyl ether (300 ml) was added dropwise to the solution at room temperature. Crystals precipitated were filtered off under reduced pressure, followed by drying. The desired compound was obtained as colorless crystals. Yield: 7.72 g (93%).

$^1$H NMR(500 MHz, (CD$_3$)$_2$SO) δ ppm 7.97(broad s, 4H), 7.32–7.16(m, 10H), 3.70(m, 1H), 3.45(m, 1H), 3.18(m, 1H), 2.86(m, 4H), 1.76(m, 1H), 1.60(m, 1H)

[EXAMPLE 43]

(A) (2S,3S,5S)-2-tert-Butoxycarbonylamino-3-hydroxy-5-amino-1,6-diphenylhexane oxalate (5S,1'S)-3-Phenylmethyl-5-(1'-tert-butoxycarbonylamino-2'-phenylethyl)-2-isoxazoline (3.69 g, 7.88 mmol) obtained in a manner similar to that described in Example 6 was dissolved in methanol (40 ml). To the solution, ammonium acetate (1.21 g, 15.8 mmol) and acetic acid (1.0 ml) were added. A 3% Pt-on-carbon catalyst (300 mg, 8.1% by weight based on substrate) was added thereto. The mixture was stirred for 24 hours in a hydrogen atmosphere at atmospheric pressure. The catalyst was removed by filtration under reduced pressure, and the filtrate was concentrated under reduced pressure. The resulting oil (6.56 g) was extracted with methylene chloride (50 ml) and an aqueous 10% NaOH (50 ml). The organic layer was washed with water, then dried over anhydrous magnesium sulfate. The desiccant was filtered off and the filtrate was concentrated under reduced pressure to give a foamy residue (4.0 g) containing (2S,3S,5S)-2-tert-butoxycarbonylamino-3-hydroxy-5-amino-1,6-diphenylhexane and (2S,3S,5R)-2-tert-butoxycarbonylamino-3-hydroxy-5-amino-1,6-diphenylhexane. Analysis by HPLC revealed that the ratio of (2S,3S,5S)-2-tert-butoxycarbonylamino-3-hydroxy-5-amino-1,6-diphenylhexane to (2S,3S,5R)-2-tert-butoxycarbonylamino-3-hydroxy-5-amino-1,6-diphenylhexane was 6:1. To the thus-obtained product, oxalic acid dihydrate (993 mg, 7.88 mmol) was added, and the resulting mixture was heated to dissolve in aqueous methanol (water content: 20 v/v%, 50 ml). When the mixture was dissolved, it was cooled and crystals precipitated were collected by filtration. The crystals were washed with aqueous methanol (water content: 20%, 10 ml×3, 3 ml×3) then dried under reduced pressure. The crude crystals (2.58 g) were confirmed, by HPLC, to contain (2S,3S,5S)-2-tert-butoxycarbonylamino-3-hydroxy-5-amino-1,6-diphenylhexane and (2S,3S,5R)-2-tert-butoxycarbonylamino-3-hydroxy-5-amino-1,6-diphenylhexane in the ratio of 97:3. The crude crystals were recrystallized from aqueous methanol (water ratio: 20 v/v%, 35 ml) in a manner similar to that as described above to give the desired compound as colorless crystals. Yield: 2.06 g (55%). This compound was identical to that obtained in Example 41. (2S,3S,5R)-2-tert-Butoxycarbonylamino-3-hydroxy-5-amino-1,6-diphenylhexane was not detected by HPLC.

(B) (2S,3S,5S)-2-tert-Butoxycarbonylamino-3-hydroxy-5-amino-1,6-diphenylhexane (2S,3S,5S)-2-tert-Butoxycarbonylamino-3-hydroxy-5-amino-1,6-diphenylhexane oxalate (500 mg, 1.05 mmol) obtained in Example 43 (A) was suspended in toluene (5 ml). An aqueous solution (5 ml) of NaOH (200 mg) was added thereto and the mixture was vigorously stirred, then separated. The organic layer was washed with water and dried over anhydrous magnesium sulfate. The desiccant was filtered off, and the filtrate was concentrated to give the desired compound as colorless crystals. Yield: 340 mg (84%).

$^1$H NMR(500 MHz, CDCl$_3$) δ ppm 7.29–7.06(m, 10H), 5.08(d, 1H, J=9.5 Hz), 3.77(d, 1H, J=10.1 Hz), 3.65(broad q, 1H), 3.01(m, 1H), 2.86(d, 2H, J=80 Hz), 2.77(dd, 1H, J=13.6, 4.6 Hz), 2.40(dd, 1H, J=13.6, 8.5 Hz), 1.55–1.39(m, 2H), 1.42(s, 9H).

[EXAMPLE 44]

(2S,3S,5S)-2-tert-Butoxycarbonylamino-3-hydroxy-5-amino-1,6-diphenylhexane oxalate (5S,1'S)-3-Phenylmethyl-5-(1'-tert-butoxycarbonylamino-2'-phenylethyl)-2-isoxazoline (250 mg, 0.66 mmol) prepared in a manner similar to that as described in Example 6 was dissolved in methanol (10 ml). Acetic acid (0.25 ml) was added to the solution. A 3% Pt-on-carbon catalyst (25 mg, 10% by weight based on substrate) was added to the mixture. The mixture was stirred for 27 hours in a hydrogen atmosphere at atmospheric pressure. The catalyst was removed by filtration under reduced pressure, and the filtrate was concentrated under reduced pressure. The resulting oil (390 mg) was dissolved in ethyl acetate (50 ml), washed successively with saturated aqueous sodium bicarbonate and saturated brine, and then dried over anhydrous magnesium sulfate. After the desiccant was filtered off, the filtrate was concentrated under reduced pressure to obtain a foamy residue (260 mg) containing (2S,3S,5S)-2-tert-butoxycarbonylamino-3-hydroxy-5-amino-1,6-diphenylhexane and (2S,3S,5R)-2-tert-butoxycarbonylamino-3-hydroxy-5-amino-1,6-diphenylhexane. Analysis by $^1$H NMR revealed that the ratio of (2S,3S,5S)-2-tert-butoxycarbonylamino-3-hydroxy-5-amino-1,6-diphenylhexane to (2S,3S,5R)-2-tert-butoxycarbonylamino-3-hydroxy-5-amino-1,6-diphenylhexane was 10:1. To the residue, oxalic acid dihydrate (83 mg, 0.66 mmol) was added, and the resulting mixture was dissolved with heat while refluxing. Diisopropyl ether (15 ml) was added, and the mixture was cooled. The crystals precipitated were collected by filtration and were dried under reduced pressure to give the desired compound as colorless crystals. Yield: 216 mg (69%). Analysis by HPLC revealed that the ratio of (2S,3S,5S)-2-tert-butoxycarbonylamino-3-hydroxy-5-amino-1,6-diphenylhexane and (2S,3S,5R)-2-tert-butoxycarbonylamino-3-hydroxy-5-amino-1,6-diphenylhexane was 97:3.

[EXAMPLE 45]

(2S,3S,5S)-2-tert-Butoxycarbonylamino-3-hydroxy-5-amino-1,6-diphenylhexane oxalate (5S,1'S)-3-Phenylmethyl-5-(1'-tert-butoxycarbonylamino-2'-phenylethyl)-2-isoxazoline (1.0 g, 2.62 mmol) prepared in a manner similar to that as described in Example 6 was dissolved in methanol (10 ml). Conc. aqueous ammonia (25%, 2 ml) was added to the solution. A 3% Pt-on-carbon catalyst (20 mg, 2% by weight based on substrate) was added to the mixture. The mixture was stirred for 96 hours in a hydrogen atmosphere at atmospheric pressure. The catalyst was removed by filtration under reduced pressure, and the filtrate was concentrated under reduced pressure. By HPLC analysis of the residue, (2S,3S,5S)-2-tert-butoxycarbonylamino-3-hydroxy-5-amino-1,6- diphenylhexane and (2S,3S,5R)-2-tert-butoxycarbonylamino- 3-hydroxy-5-amino-1,6-diphenylhexane were contained in the ratio of 5:1. To the oil, oxalic acid dihydrate (330 mg, 2.62 mmol) was added, and the resulting mixture was heated to dissolve in aqueous methanol (water content: 20 v/v%, 12 ml). When the mixture was dissolved, it was cooled and crystals precipitated were collected by filtration. Yield: 510 mg (41%). The crystals were confirmed, by HPLC, to contain (2S,3S,5S)-2-tert-butoxycarbonylamino-3-hydroxy-5-amino-1,6-diphenylhexane and (2S,3S,5R)-2-tert-butoxycarbonylamino-3-hydroxy-5-amino-1,6-diphenylhexane in the ratio of 97:3.

[EXAMPLE 46]
(2S,3S,5S)-2-tert-Butoxycarbonylamino-3-hydroxy-5-amino-1,6-diphenylhexane (5S,1'S)-3-Phenylmethyl-5-(1'-tert-butoxycarbonylamino-2'-phenylethyl)-2-isoxazoline (500 mg, 1.31 mmol) prepared in a manner similar to that described in Example 6 was dissolved in an ammonia/methanol solution (3%, 10 ml). A 5% Pd-on-carbon catalyst (50 mg, 10% by weight based on substrate) was added to the solution. The mixture was stirred for 72 hours in a hydrogen atmosphere at atmospheric pressure. The catalyst was removed by filtration under reduced pressure, and the filtrate was concentrated under reduced pressure to give a foamy residue containing (2S,3S,5S)-2-tert-butoxycarbonylamino-3-hydroxy-5-amino-1,6-diphenylhexane and (2S,3S,5R)-2-tert-butoxycarbonylamino-3-hydroxy-5-amino-1,6-diphenylhexane. Analysis by HPLC revealed that the ratio of (2S,3S,5S)-2-tert-butoxycarbonylamino-3-hydroxy-5-amino-1,6-diphenylhexane to (2S,3S,5R)-2-tert-butoxycarbonylamino-3-hydroxy-5-amino-1,6-diphenylhexane was 3:1.

[EXAMPLE 47]
(2RS,3RS,5RS)-2,5-Diamino-1,6-diphenyl-3-hydroxyhexane and (2RS,3RS,5SR)-2,5-diamino-1,6-diphenyl-3-hydroxyhexane A crude form (77 mg) of (5RS,1'RS)-3-phenylmethyl-5-(1'-amino-2'-phenylethyl)-2-isoxazoline obtained in Example 37 was dissolved in diethyl ether (6 ml). Lithium aluminum hydride (55 mg) was added to the solution. The mixture was refluxed with heat for 6 hours and then cooled, after which a 10% aqueous sodium hydroxide was added thereto. The mixture was extracted with diethyl ether and methylene chloride respectively. The organic layer were combined together and concentrated under reduced pressure to give a crude pale yellow oil (77 mg) of a mixture of (2RS,3RS,5RS)-2,5-diamino-1,6-diphenyl-3-hydroxyhexane and (2RS,3RS,5SR)-?,5-diamino-1,6-diphenyl-3-hydroxyhexane. The oil was purified by silica gel thin-layer chromatography (solvent for development, chloroform: methanol:isopropylamine=96:2:2) to give (2RS,3RS,5RS)-2,5-diamino-1,6-diphenyl-3-hydroxyhexane (39 mg) and (2RS,3RS,5SR)-2,5-diamino-1,6-diphenyl-3-hydroxyhexane (27 mg) both as white solids. (2RS,3RS,5RS)-2,5-Diamino-1,6-diphenyl-3-hydroxyhexane:

$^1$H NMR(500 MHz, CDCl$_3$) δ ppm 7.32–7.13(m, 10H), 3.73(dt, 1H, J=10.5, 3.2 Hz), 3.11 (m, 1H), 2.89(dd, 1H, J=13.2, 8.5 Hz), 2, 82(m, 2H), 2.57(dd, 1H, J=13.2, 8.8 Hz), 2.51 (dd, 1H, J=13.5, 8, 3 Hz), 1.67(dt, 1H, J=14.0, 2.3 Hz), 1.53(dt, 1H, J=14.0, 10.6 Hz). (2RS,3RS,5RS)-2,5-Diamino-1,6-diphenyl-3-hydroxyhexane:

$^1$H NMR(500 MHz, CDCl$_3$) δ ppm 7.33–7.13(m, 10H), 3.77(m, 1H), 3.43(m, 1H), 2.85(m, 2H), 2.80(dd, 1H, J=13.4, 5.1 Hz), 2.61 (dd, 1H, J=13.4, 8, 9 Hz), 2.47(dd, 1H, J=14.3, 10.3 Hz), 1.79(ddd, 1H, J=14.1, 9.6, 3.1 Hz), 1.52 (ddd, 1H, J=14.1, 7.8, 2.9 Hz).

[EXAMPLE 48]
(2S,3S,5S)-2-Acetylamino-3-hydroxy-5-amino-1,6-diphenylhexane and (2S,3S,5R)-2-acetylamino-3-hydroxy-5-amino-1,6-diphenylhexane (5S,1'S)-3-Phenylmethyl-5-(1'-acetylamino-2'-phenylethyl)-2-isoxazoline (250 mg, 0.78 mmol) prepared in a manner similar to that described in Example 17 was dissolved in methanol (10 ml), and acetic acid (0.25 ml) was added thereto. A 3% Pt-on-carbon catalyst (25 mg, 10% by weight based on substrate) was added to the mixture. The resulting mixture was stirred for 5 days in a hydrogen atmosphere at atmospheric pressure. The catalyst was removed by filtration under reduced pressure, and the filtrate was concentrated under reduced pressure. The resulting oil was dissolved in ethyl acetate (50 ml). The solution was washed with saturated sodium bicarbonate and then with saturated brine, and dried over anhydrous magnesium sulfate. After the desiccant was filtered off, the filtrate was concentrated under reduced pressure to give an oil (250 mg). The oil was purified by silica gel column chromatography (solvent for elution, chloroform: methanol=7:1) to give the mixture of (2S,3S,5S)-2-acetylamino-3-hydroxy-5-amino-1,6-diphenylhexane and (2S,3S,5R)-2-acetylamino-3-hydroxy-5-amino-1,6-diphenylhexane as a colorless solid. Yield: 150 mg. (2S,3S,5S)-2-Acetylamino-3-hydroxy-5-amino-1,6-diphenylhexane in the mixture:

$^1$H NMR(500 MHz, CDCl$_3$) δ ppm 7.30–7.07(m, 10H), 6.02(d, 1H, J=9.3 Hz), 4.03(m, 1H), 3.79(m, 1H), 3.03(m, 1H), 2.86(d, 2H, J=7.7 Hz), 2.79(dd, 1H, J=13.6, 4.9 Hz), 2.43(dd, 1H, J=13.6, 8.5 Hz), 1.98(s, 3H), 1.54(dt, 1H, J=14.2, 2.0 Hz), 1. 37(dt, 1H, J=14.2, 11.1 Hz).

[EXAMPLE 49]
(2S,3S,5S)-2-N,N-Dibenzylamino-3-hydroxy-5-amino-1,6-diphenylhexane (5S,1'S)-3-Phenylmethyl-5-(1'-N,N-dibenzylamino-2'-phenylethyl)-2-isoxazoline (9.2 g, 20 mmol) obtained in Example 21 was dissolved in diisopropyl ether (92 ml). Lithium aluminum hydride (3.8 g, 100 mmol) was added to the solution under nitrogen. The mixture was stirred at 60° C. for 5 hours and then cooled to room temperature. A 25% aqueous sodium hydroxide (120 g), diisopropyl ether (200 ml), and water (50 ml) were added to the mixture. Solid mass was removed by filtration, and the filtrate was extracted. Then, the organic layer was concentrated under reduced pressure to give an oil (9.2 g). The oil (4.0 g) was separated and purified by silica gel column chromatography (solvent for elution, hexane:ethyl acetate=1:1) to give the desired compound as colorless crystals. Yield: 2.32 g.

$^1$H NMR(500 MHz, CDCl$_3$) δ ppm 7.33–7.09(m, 20H), 4.17(d, 2H, J=13.7 Hz), 3.67(m, 1H), 3.46(d, 2H, J=13.7 Hz), 3.05(dd, 1H, J=13.3, 4.6 Hz), 2.98(m, 1H), 2.94(dd, 1H, J=13.3, 9.1 Hz), 2.70(dd, 1H, J=13.3, 5.0 Hz), 2.62(m, 1H), 2.47(dd, 1H, J=13.3, 7.8 Hz), 1.63(m, 1H), 1.26(m, 1H).

[EXAMPLE 50]
(2S,3S,5S)-2-N,N-Dibenzylamino-3-hydroxy-5-amino-1,6-diphenylhexane (5S,1'S)-3-Phenylmethyl-5-(1'-N,N-dibenzylamino-2'-phenylethyl)-2-isoxazoline (100 mg, 0.217 mmol) obtained in Example 21 was dissolved in an ammonia/ethanol solution (3.4%, 20 ml). A 3% Pt-on-carbon catalyst (100 mg) was added to the solution. The resulting mixture was stirred for 20 hours at atmospheric pressure under hydrogen atmosphere. The catalyst was removed by filtration, followed by washing with diisopropyl ether (5 ml). The filtrate was concentrated under reduced pressure to give a pale pink oil (86 mg), the entirety of which was purified by silica gel thin-layer chromatography (solvent for development, chloroform:methanol:isopropylamine=96:2:2) to give the desired compound (yield: 52 mg) as colorless oil. The thus obtained compound agreed with the compound obtained in Example 49.

Industrial Applicability

The present invention provides novel 2-isoxazoline derivatives represented by formula [1], [2] or [3] or acid addition salts thereof, which are useful intermediates for 2,5-diamino-1,6-diphenyl-3-hydroxyhexane derivatives which in turn serve as intermediates in the synthesis of medicines such as retrovirus protease inhibitors. The invention also provides methods for preparing such derivatives as well as methods for preparing 2,5-diamino-1,6-diphenyl-3-hydroxyhexane derivatives using the 2-isoxazoline derivatives. The methods of the invention are industrially very useful because heavy-metal and special reagents are not used and very low temperature reaction conditions are not required.

We claim:

1. A 2-isoxazoline compound represented by the following formula [1] or an acid addition salt thereof:

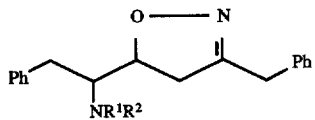

[1]

wherein Ph represents phenyl; and each of $R^1$ and $R^2$ independently represents hydrogen, acyl, alkyloxycarbonyl, arylalkyloxycarbonyl, aryloxycarbonyl, alkylaminocarbonyl, arylalkylaminocarbonyl, arylaminocarbonyl, alkyl, arylalkyl, aryl, alkylsulfonyl, arylalkylsulfonyl, or arylsulfonyl, or $R^1$ and $R^2$ are linked to each other to represent divalent acyl.

2. A mixture of 2-isoxazoline compounds represented by the following formulas [2] and [3] or a mixture of acid addition salts thereof:

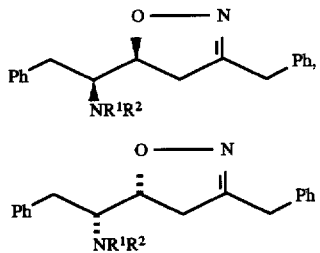

[2]

[3]

wherein Ph represents phenyl; and each of $R^1$ and $R^2$ independently represents hydrogen, acyl, alkyloxycarbonyl, arylalkyloxycarbonyl, aryloxycarbonyl, alkylaminocarbonyl, arylalkylaminocarbonyl, arylaminocarbonyl, alkyl, arylalkyl, aryl, alkylsulfonyl, arylalkylsulfonyl, or arylsulfonyl, or $R^1$ and $R^2$ are linked to each other to represent divalent acyl.

3. A 2-isoxazoline compound represented by the following formula [2] or an acid addition salt thereof:

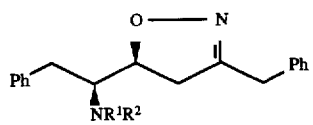

[2]

wherein Ph represents phenyl; and each of $R^1$ and $R^2$ independently represents hydrogen, acyl, alkyloxycarbonyl, arylalkyloxycarbonyl, aryloxycarbonyl, alkylaminocarbonyl, arylalkylaminocarbonyl, arylaminocarbonyl, alkyl, arylalkyl, aryl, alkylsulfonyl, arylalkylsulfonyl, or arylsulfonyl, or $R^1$ and $R^2$ are linked to each other to represent divalent acyl.

4. A 2-isoxazoline compound or an acid addition salt thereof as defined in claim 1, wherein $R^1$ is hydrogen and $R^2$ is hydrogen, acyl, alkyloxycarbonyl, arylalkyloxycarbonyl, or aryloxycarbonyl, or $R^1$ and $R^2$ are linked to each other to represent divalent acyl.

5. A 2-isoxazoline compound or an acid addition salt thereof as defined in claim 2, wherein $R^1$ is hydrogen and $R^2$ is hydrogen, acyl, alkyloxycarbonyl, arylalkyloxycarbonyl, or aryloxycarbonyl, or $R^1$ and $R^2$ are linked to each other to represent divalent acyl.

6. A 2-isoxazoline compound or an acid addition salt thereof as defined in claim 3, wherein $R^1$ is hydrogen and $R^2$ is hydrogen, acyl, alkyloxycarbonyl, arylalkyloxycarbonyl, or aryloxycarbonyl, or $R^1$ and $R^2$ are linked to each other to represent divalent acyl.

7. An acid addition salt of the 2-isoxazoline compound as defined in claim 1, wherein $R^1$ and $R^2$ are both hydrogen, and the acid is inorganic acid, carboxylic acid, or sulfonic acid.

8. A mixture of acid addition salts of 2-isoxazoline compounds as defined in claim 2, wherein $R^1$ and $R^2$ are both hydrogen, and the acid is inorganic acid, carboxylic acid, or sulfonic acid.

9. An acid addition salt of the 2-isoxazoline compound as defined in claim 3, wherein $R^1$ and $R^2$ are both hydrogen, and the acid is inorganic acid, carboxylic acid, or sulfonic acid.

10. A 2-isoxazoline compound selected from the group consisting of (5RS,1'RS)-3-phenylmethyl-5-(1'-amino-2'-phenylethyl)-2-isoxazoline, (5RS,1'RS)-3-phenylmethyl-5-(1'-formylamino-2'-phenylethyl)-2-isoxazoline, (5RS,1'RS)-3-phenylmethyl-5-(1'-acetylamino-2'-phenylethyl)-2-isoxazoline, (5RS,1'RS)-3-phenylmethyl-5-(1'-benzoylamino-2'-phenylethyl)-2-isoxazoline, (5RS,1'RS)-3-phenylmethyl-5-(1'-tert-butoxycarbonylamino-2'-phenylethyl)-2-isoxazoline,(5RS,1'RS)-3-phenylmethyl-5-(1'-benzyloxycarbonylamino-2'-phenylethyl)-2-isoxazoline, (5RS,1'RS)-3-phenylmethyl-5-(1'-methoxycarbonylamino-2'-phenylethyl)-2-isoxazoline, (5RS,1'RS)-3-phenylmethyl-5-(1'-phthalimido-2'-phenylethyl)-2-isoxazoline, and (5RS,1'RS)-3-phenylmethyl-5-(1'-N,N-dibenzylamino-2'-phenylethyl)-2-isoxazoline.

11. An acid addition salt of 2-isoxazoline compound selected from the group consisting of (5RS,1'RS)-3-phenylmethyl-5-(1'-amino-2'-phenylethyl )-2-isoxazoline hydrochloride, (5RS,1'RS)-3-phenylmethyl-5-(1'-amino-2'-phenylethyl)-2-isoxazoline p-toluenesulfonate, (5RS,1'RS)-3-phenylmethyl-5-(1'-amino-2'-phenylethyl)-2-isoxazoline benzenesulfonate, (5RS,1'RS)-3-phenylmethyl-5-(1'-amino-2'-phenylethyl)-2-isoxazoline methanesulfonate, (5RS,1'RS)-3-phenylmethyl-5-(1'-amino-2'-phenylethyl)-2-isoxazoline oxalate, and (5RS,1'RS)-3-phenylmethyl-5-(1'-amino-2'-phenylethyl)-2-isoxazoline benzoate.

12. A 2-isoxazoline compound selected from the group consisting of (5S,1'S)-3-phenylmethyl-5-(1'-amino-2'- phenylethyl)-2-isoxazoline, (5S,1'S)-3-phenylmethyl-5-(1'-formylamino-2'-phenylethyl)-2-isoxazoline, (5S,1'S)-3-phenylmethyl-5-(1'-acetylamino-2'-phenylethyl)-2-isoxazoline, (5S,1'S)-3-phenylmethyl-5-(1'-benzoylamino-2'-phenylethyl)-2-isoxazoline, (5S,1'S)-3-phenylmethyl-5-(1'-tert-butoxycarbonylamino-2'-phenylethyl)-2-isoxazoline, (5S,1'S)-3-phenylmethyl-5-(1'-benzyloxycarbonylamino-2'-phenylethyl)-2-isoxazoline, (5S,1'S)-3-phenylmethyl-5-(1'-methoxycarbonylamino-2'-phenylethyl)-2-isoxazoline, (5S,1'S)-3-phenylmethyl-5-(1'-phthalimido-2'-phenylethyl)-2-isoxazoline, and (5S,1'S)-3-phenylmethyl-5-(1'-N,N-dibonzylamino-2'-phenylethyl)-2-isoxazoline.

13. An acid addition salt of 2-isoxazoline compound selected from the group consisting of (5S,1'S)-3-phenylmethyl-5-(1'-amino-2'-phenylethyl)-2-isoxazoline hydrochloride, (5S,1'S)-3-phenylmethyl-5-(1'-amino-2'-phenylethyl)-2-isoxazoline p-toluenesulfonate, (5S,1'S)-3-phenylmethyl-5-(1'-amino-2'-phenylethyl)-2-isoxazoline benzenesulfonate, (5S,1'S)-3-phenylmethyl-5-(1'-amino-2'-phenylethyl)-2-isoxazoline methanesulfonate, (5S,1'S)-3-phenylmethyl-5-(1'-amino-2'-phenylethyl)-2-isoxazoline oxalate, (5S,1'S)-3-phenylmethyl-5-(1'-amino-2'-phenylethyl)-2-isoxazoline benzoate, and (5S,1'S)-3-phenylmethyl-5-(1'-amino-2'-phenylethyl)-2-isoxazoline (S)-mandelate.

14. A method for preparing a 2-isoxazoline compound represented by formula [1] or an acid addition salt thereof, which comprises performing any one of the procedures of substitution of $R^1$ and/or $R^2$, neutralization, acid-addition, or combinations of these procedures using another 2-isoxazoline compound represented by formula [1] or an acid addition salt thereof:

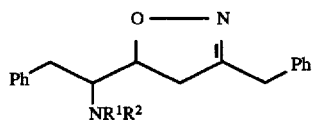

wherein Ph represents phenyl; and each of $R^1$ and $R^2$ independently represents hydrogen, acyl, alkyloxycarbonyl, arylalkyloxycarbonyl, aryloxycarbonyl, alkylaminocarbonyl, arylalkylaminocarbonyl, arylaminocarbonyl, alkyl, arylalkyl, aryl, alkylsulfonyl, arylalkylsulfonyl, or arylsulfonyl, or $R^1$ and $R^2$ are linked to each other to represent divalent acyl.

15. A method for preparing a mixture of 2-isoxazoline compounds represented by formulas [2] and [3] or a mixture of acid addition salts thereof, which comprises performing any one of the procedures of substitution of $R^1$ and/or $R^2$, neutralization, acid-addition, or combinations of these procedures using another mixture of 2-isoxazoline compounds represented by formulas [2] and [3] or a mixture of acid addition salts thereof:

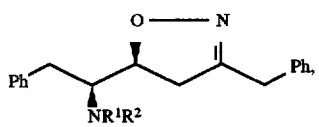

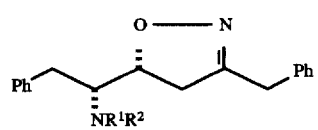

wherein Ph represents phenyl; and each of $R^1$ and $R^2$ independently represents hydrogen, acyl, alkyloxycarbonyl, arylalkyloxycarbonyl, aryloxycarbonyl, alkylaminocarbonyl, arylalkylaminocarbonyl, arylaminocarbonyl, alkyl, arylalkyl, aryl, alkylsulfonyl, arylalkylsulfonyl, or arylsulfonyl, or $R^1$ and $R^2$ are linked to each other to represent divalent acyl.

16. A method for preparing a 2-isoxazoline compound represented by formula [2] or an acid addition salt thereof, which comprises performing any one of the procedures of substitution of $R^1$ and/or $R^2$, neutralization, acid-addition, or combinations of these procedures using another 2-isoxazoline compound represented by formula [2] or an acid addition salt thereof:

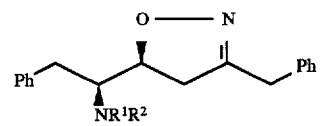

wherein Ph represents phenyl; and each of $R^1$ and $R^1$ independently represents hydrogen, acyl, alkyloxycarbonyl, arylalkyloxycarbonyl, aryloxycarbonyl, alkylaminocarbonyl, arylalkylaminocarbonyl, arylaminocarbonyl, alkyl, arylalkyl, aryl, alkylsulfonyl, arylalkylsulfonyl, or arylsulfonyl, or $R^1$ and $R^2$ are linked to each other to represent divalent acyl.

17. A method for preparing a 2-isoxazoline compound represented by formula [1], comprising reacting a compound represented by formula [4] with phenylacetonitrile oxide:

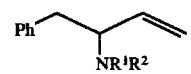

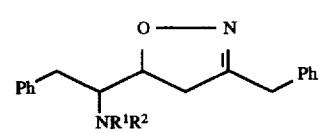

wherein Ph represents phenyl; and each of $R^1$ and $R^1$ independently represents hydrogen, acyl, alkyloxycarbonyl, arylalkyloxycarbonyl, aryloxycarbonyl, alkylaminocarbonyl, arylalkylaminocarbonyl, arylaminocarbonyl, alkyl, arylalkyl, aryl, alkylsulfonyl, arylalkylsulfonyl, or arylsulfonyl, or $R^1$ and $R^2$ are linked to each other to represent divalent acyl.

18. A method for preparing a 2-isoxazoline compound represented by formula [2] and/or formula [3], comprising reacting a compound represented by formula [4] with phenylacetonitrile oxide:

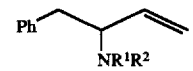

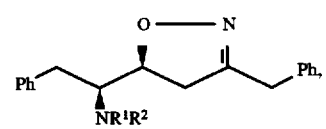

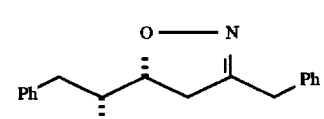

wherein Ph represents phenyl; and each of $R^1$ and $R^2$ independently represents hydrogen, acyl, alkyloxycarbonyl, arylalkyloxycarbonyl, aryloxycarbonyl, alkylaminocarbonyl, arylalkylaminocarbonyl, arylaminocarbonyl, alkyl, arylalkyl, aryl, alkylsulfonyl, arylalkylsulfonyl, or arylsulfonyl, or $R^1$ and $R^2$ are linked to each other to represent divalent acyl.

19. A method for preparing a 2-isoxazoline compound represented by formula [2], comprising reacting a compound represented by formula [5] with phenylacetonitrile oxide:

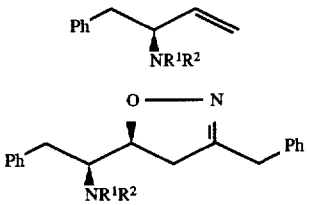

wherein Ph represents phenyl; and each of $R^1$ and $R^2$ independently represents hydrogen, acyl, alkyloxycarbonyl, arylalkyloxycarbonyl, aryloxycarbonyl, alkylaminocarbonyl, arylalkylaminocarbonyl, arylaminocarbonyl, alkyl, arylalkyl, aryl, alkylsulfonyl, arylalkylsulfonyl, or arylsulfonyl, or $R^1$ and $R^2$ are linked to each other to represent divalent acyl.

20. A method for preparing a 2-isoxazoline compound as defined in claim 17, wherein $R^1$ is hydrogen and $R^2$ is acyl, alkyloxycarbonyl, arylalkyloxycarbonyl, aryloxycarbonyl, alkylaminocarbonyl, arylalkylaminocarbonyl, arylaminocarbonyl, alkylsulfonyl, arylalkylsulfonyl, or arylsulfonyl; or $R^1$ and $R^2$ are linked to each other to represent divalent acyl; or each of $R^1$ and $R^2$ independently represents arylalkyl.

21. A method for preparing a 2-isoxazoline compound as defined in claim 18, wherein $R^1$ is hydrogen and $R^2$ is acyl, alkyloxycarbonyl, arylalkyloxycarbonyl, aryloxycarbonyl, alkylaminocarbonyl, arylalkylaminocarbonyl, arylaminocarbonyl, alkylsulfonyl, arylalkylsulfonyl, or arylsulfonyl; or $R^1$ and $R^2$ are linked to each other to represent divalent acyl; or each of $R^1$ and $R^2$ independently represents arylalkyl.

22. A method for preparing a 2-isoxazoline compound as defined in claim 19, wherein $R^1$ is hydrogen and $R^2$ is acyl, alkyloxycarbonyl, arylalkyloxycarbonyl, aryloxycarbonyl, alkylaminocarbonyl, arylalkylaminocarbonyl, arylaminocarbonyl, alkylsulfonyl, arylalkylsulfonyl, or arylsulfonyl; or $R^1$ and $R^2$ are linked to each other to represent divalent acyl; or each of $R^1$ and $R^2$ independently represents arylalkyl.

23. A method for preparing a 2-isoxazoline compound as defined in claim 20, wherein $R^1$ is hydrogen and $R^2$ is formyl, acetyl, methoxycarbonyl, tert-butoxycarbonyl, or benzyloxycarbonyl; or $R^1$ and $R^2$ are linked to each other to represent phthaloyl; or each of $R^1$ and $R^2$ independently represents benzyl.

24. A method for preparing a 2-isoxazoline compound as defined in claim 21, wherein $R^1$ is hydrogen and $R^2$ is formyl, acetyl, methoxycarbonyl, tert-butoxycarbonyl, or benzyloxycarbonyl; or $R^1$ and $R^2$ are linked to each other to represent phthaloyl; or each of $R^1$ and $R^2$ independently represents benzyl.

25. A method for preparing a 2-isoxazoline compound as defined in claim 22, wherein $R^1$ is hydrogen and $R^2$ is formyl, acetyl, methoxycarbonyl, tert-butoxycarbonyl, or benzyloxycarbonyl; or $R^1$ and $R^2$ are linked to each other to represent phthaloyl; or each of $R^1$ and $R^2$ independently represents benzyl.

26. A method for purifying an acid addition salt of (5RS,1'RS)-3-phenylmethyl-5-(1'-amino-2'-phenylethyl)-2-isoxazoline, comprising obtaining an acid addition salt of (5RS,1'RS)-3-phenylmethyl-5-(1-amino-2'-phenylethyl)-2-isoxazoline from a mixture, at an arbitrary ratio, of (5RS,1'RS)-3-phenylmethyl-5-(1'-amino-2'-phenylethyl)-2-isoxazoline and (5RS,1'SR)-3-phenylmethyl-5-(1-amino-2'-phenylethyl)-2-isoxazoline or from an acid addition salt of the mixture.

27. A method for purifying an acid addition salt of (5RS,1'RS)-3-phenylmethyl-5-(1'-amino-2'-phenylethyl)-2-isoxazoline as defined in claim 26, wherein the acid addition salt is a salt of inorganic acid, carboxylic acid, or sulfonic acid.

28. A method for purifying an acid addition salt of (5RS,1'RS)-3-phenylmethyl-5-(1'-amino-2'-phenylethyl)-2-isoxazoline as defined in claim 27, wherein the acid addition salt is hydrochloride or p-toluenesulfonate.

29. A method for purifying an acid addition salt of (5S,1'S)-3-phenylmethyl-5-(1'-amino-2'-phenylethyl)-2-isoxazoline, comprising obtaining an acid addition salt of (5S,1'S)-3-phenylmethyl-5-(1'-amino-2'-phenylethyl)-2-isoxazoline from a mixture, at an arbitrary ratio, of (5S,1'S)-3-phenylmethyl-5-(1-amino-2'-phenylethyl)-2-isoxazoline and (5R,1'S)-3-phenylmethyl-5-(1'-amino-2'-phenylethyl)-2-isoxazoline or from an acid addition salt of the mixture.

30. A method for purifying an acid addition salt of (5S,1'S)-3-phenylmethyl-5-(1'-amino-2'-phenylethyl)-2-isoxazoline as defined in claim 29, wherein the acid addition salt is a salt of inorganic acid, carboxylic acid, or sulfonic acid.

31. A method for purifying an acid addition salt of (5S,1'S)-3-phenylmethyl-5-(1'-amino-2'-phenylethyl)-2-isoxazoline as defined in claim 30, wherein the acid addition salt is hydrochloride or p-toluenesulfonate.

* * * * *